US008592208B2

(12) United States Patent (10) Patent No.: US 8,592,208 B2
Shroff (45) Date of Patent: Nov. 26, 2013

(54) METHODS OF EXPANDING HUMAN EMBRYONIC STEM CELLS

(71) Applicant: Geeta Shroff, New Delhi (IN)

(72) Inventor: Geeta Shroff, New Delhi (IN)

(*) Notice: Subject to any disclaimer, the term of this patent is extended or adjusted under 35 U.S.C. 154(b) by 0 days.

(21) Appl. No.: 13/735,281

(22) Filed: Jan. 7, 2013

(65) Prior Publication Data

US 2013/0122588 A1 May 16, 2013

Related U.S. Application Data

(62) Division of application No. 12/224,839, filed as application No. PCT/IB2007/002292 on Mar. 6, 2007.

(60) Provisional application No. 60/844,350, filed on Sep. 14, 2006.

(30) Foreign Application Priority Data

Mar. 7, 2006 (IN) .............................. 582/DEL/2006
Jun. 26, 2006 (IN) ............................ 1500/DEL/2006

(51) Int. Cl.
*C12N 5/00* (2006.01)

(52) U.S. Cl.
USPC .............................. 435/366; 435/325; 435/375

(58) Field of Classification Search
None
See application file for complete search history.

(56) References Cited

U.S. PATENT DOCUMENTS

| | | |
|---|---|---|
| 5,061,620 A | 10/1991 | Tsukamoto et al. |
| 5,166,065 A | 11/1992 | Williams et al. |
| 5,256,560 A | 10/1993 | Lawman et al. |
| 5,411,883 A | 5/1995 | Boss et al. |
| 5,453,357 A | 9/1995 | Hogan |
| 5,453,457 A | 9/1995 | Meltzer et al. |
| 5,486,359 A | 1/1996 | Caplan et al. |
| 5,541,103 A | 7/1996 | Kanz et al. |
| 5,589,376 A | 12/1996 | Anderson et al. |
| 5,622,853 A | 4/1997 | Terstappen et al. |
| 5,677,136 A | 10/1997 | Simmons et al. |
| 5,681,559 A | 10/1997 | DiGiusto et al. |
| 5,690,926 A | 11/1997 | Hogan |
| 5,744,347 A | 4/1998 | Wagner et al. |
| 5,750,397 A | 5/1998 | Tsukamoto et al. |
| 5,753,505 A | 5/1998 | Luskin |
| 5,807,686 A | 9/1998 | Wagner et al. |
| 5,814,511 A | 9/1998 | Chang et al. |
| 5,821,108 A | 10/1998 | Akashi et al. |
| 5,827,735 A | 10/1998 | Young et al. |
| 5,840,580 A | 11/1998 | Terstappen et al. |
| 5,843,780 A | 12/1998 | Thomson |
| 5,851,832 A | 12/1998 | Weiss et al. |
| 5,858,782 A | 1/1999 | Long et al. |
| 5,874,301 A | 2/1999 | Keller et al. |
| 5,876,956 A | 3/1999 | Jones et al. |
| 5,908,782 A | 6/1999 | Marshak et al. |
| 5,914,268 A | 6/1999 | Keller et al. |
| 5,955,357 A | 9/1999 | Bender et al. |
| 5,968,829 A | 10/1999 | Carpenter |
| 5,972,627 A | 10/1999 | Galy |
| 5,997,871 A | 12/1999 | Gallo et al. |
| 6,028,064 A | 2/2000 | Rodriguez et al. |
| 6,043,235 A | 3/2000 | Cook et al. |
| 6,090,622 A | 7/2000 | Gearhart et al. |
| 6,117,675 A | 9/2000 | van der Kooy et al. |
| 6,129,911 A | 10/2000 | Faris |
| 6,200,806 B1 | 3/2001 | Thomson |
| 6,245,757 B1 | 6/2001 | Chopp et al. |
| 6,251,669 B1 | 6/2001 | Luskin |
| 6,319,911 B1 | 11/2001 | Rodriguez |
| 6,387,367 B1 | 5/2002 | Davis-Sproul et al. |
| 6,410,320 B1 | 6/2002 | Humes |
| 6,416,999 B1 | 7/2002 | Li et al. |
| 6,436,704 B1 | 8/2002 | Roberts et al. |
| 6,458,588 B1 | 10/2002 | Arnaout et al. |
| 6,465,247 B1 | 10/2002 | Weissman et al. |
| 6,469,139 B1 | 10/2002 | Roitt et al. |
| 6,485,971 B1 | 11/2002 | Kaur et al. |
| 6,517,872 B1 | 2/2003 | Yayon et al. |
| 6,537,807 B1 | 3/2003 | Smith et al. |
| 6,562,619 B1 | 5/2003 | Gearhart et al. |

(Continued)

FOREIGN PATENT DOCUMENTS

| | | |
|---|---|---|
| UA | 59678 A | 9/2003 |
| UA | 64826 C2 | 3/2004 |

(Continued)

OTHER PUBLICATIONS

Amit, M. et al., "Feeder Layer- and Serum-Free Culture of Human Embryonic Stem Cells," *Biol. Reprod.* 70:837-845, Society for the Study of Reproduction, Inc. (2004).

(Continued)

*Primary Examiner* — Blaine Lankford
(74) *Attorney, Agent, or Firm* — Sterne, Kessler, Goldstein & Fox P.L.L.C.

(57) ABSTRACT

The present invention relates to a pharmaceutical composition comprising of preparations of human embryonic stem (hES) cells and their derivatives and methods for their transplantation into the human body, wherein transplantation results in the clinical reversal of symptoms, cure, stabilization or arrest of degeneration of a wide variety of presently incurable and terminal medical conditions, diseases and disorders. The invention further relates to novel processes of preparing novel stem cell lines which are free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media. This invention further relates to the isolation, culture, maintenance, expansion, differentiation, storage, and preservation of such stem cells.

11 Claims, No Drawings

(56) References Cited

U.S. PATENT DOCUMENTS

| | | | |
|---|---|---|---|
| 6,562,857 | B2 | 5/2003 | Collins et al. |
| 6,583,109 | B1 | 6/2003 | Gallo et al. |
| 6,585,982 | B1 | 7/2003 | Grøndahl et al. |
| 6,635,445 | B1 | 10/2003 | Igarashi et al. |
| 6,642,048 | B2 | 11/2003 | Xu et al. |
| 6,734,015 | B1 | 5/2004 | Rao et al. |
| 6,753,153 | B2 | 6/2004 | Sarvetnick et al. |
| 6,761,883 | B2 | 7/2004 | Weissman et al. |
| 6,767,737 | B1 | 7/2004 | Wilson et al. |
| 6,777,231 | B1 | 8/2004 | Katz et al. |
| 6,787,353 | B1 | 9/2004 | Rao et al. |
| 6,800,480 | B1 | 10/2004 | Bodnar et al. |
| 6,812,027 | B2 | 11/2004 | Goldman et al. |
| 6,835,567 | B1 | 12/2004 | Sah et al. |
| 6,852,532 | B2 | 2/2005 | Mayer-Proschel et al. |
| 6,852,533 | B1 | 2/2005 | Rafii et al. |
| 6,872,389 | B1 | 3/2005 | Faris |
| 6,890,724 | B2 | 5/2005 | Anderson et al. |
| 6,908,763 | B1 | 6/2005 | Akashi et al. |
| 6,908,764 | B2 | 6/2005 | Czichos et al. |
| 6,913,925 | B1 | 7/2005 | Sah et al. |
| 6,921,632 | B2 | 7/2005 | Lim et al. |
| 6,936,281 | B2 | 8/2005 | Seshi |
| 6,969,608 | B1 | 11/2005 | Miller et al. |
| 7,029,913 | B2 | 4/2006 | Thomson |
| 7,037,702 | B2 | 5/2006 | Luche et al. |
| 7,071,205 | B2 | 7/2006 | Zhi et al. |
| 7,081,457 | B2 | 7/2006 | Zhang et al. |
| 7,084,151 | B2 | 8/2006 | Zhi et al. |
| 7,091,234 | B2 | 8/2006 | Fensome et al. |
| 7,427,415 | B2 | 9/2008 | Scharp et al. |
| 2002/0019046 | A1 | 2/2002 | Carpenter et al. |
| 2002/0076747 | A1 | 6/2002 | Price et al. |
| 2003/0017587 | A1 | 1/2003 | Rader et al. |
| 2004/0071665 | A1 | 4/2004 | Xiao et al. |
| 2004/0107453 | A1 | 6/2004 | Furcht et al. |
| 2004/0241144 | A1 | 12/2004 | Kaps et al. |
| 2005/0124003 | A1 | 6/2005 | Atala et al. |
| 2006/0073587 | A1 | 4/2006 | Stice et al. |
| 2009/0123433 | A1 | 5/2009 | Shroff |
| 2013/0122486 | A1 | 5/2013 | Shroff |

FOREIGN PATENT DOCUMENTS

| | | |
|---|---|---|
| UA | 71388 A | 11/2004 |
| WO | WO 01/19379 A2 | 3/2001 |
| WO | WO 01/19966 A2 | 3/2001 |
| WO | WO 01/80865 A2 | 11/2001 |
| WO | WO 01/85917 A2 | 11/2001 |
| WO | WO 02/18549 A1 | 3/2002 |
| WO | WO 02/079457 A1 | 10/2002 |
| WO | WO 03/026584 A2 | 4/2003 |
| WO | WO 03/083070 A2 | 10/2003 |
| WO | WO 03/105908 A2 | 12/2003 |
| WO | WO 2004/007696 A2 | 1/2004 |
| WO | WO 2004/010959 A2 | 2/2004 |
| WO | WO 2004/044158 A2 | 5/2004 |
| WO | WO 2004/081172 A2 | 9/2004 |
| WO | WO 2005/021720 A2 | 3/2005 |
| WO | WO 2005/052138 A1 | 6/2005 |
| WO | WO 2005/065354 A2 | 7/2005 |
| WO | WO 2005/080551 A2 | 9/2005 |
| WO | WO 2005/099758 A2 | 10/2005 |

OTHER PUBLICATIONS

De Sousa, P.A. et al., "The road to providing human embryo stem cells for therapeutic use: the UK experience," *Reproduction (Cambridge)* 132:681-689, BioScientifica Ltd. (2006).

Ezashi, T. et al., "Low $O_2$ tensions and the prevention on differentiation of hES cells," *Proc. Natl. Acad. Sci. U.S.A. 102:* 4783-4788, National Academy of Sciences (Mar. 29, 2005).

Gerami-Naini, B. et al., "Trophoblast Differentiation in Embryoid Bodies Derived from Human Embryonic Stem Cells," *Endocrinology 145*:1517-1524, Endocrine Society (2004).

Gerecht-Nir, S. and Itskovitz-Eldor, J., "The promise of human embryonic stem cells," *Best Pract. Res. Clin. Obstet. Gynaecol. 18*:843-852, Bailliére Tindall Ltd. (2004).

Gruen, L. and Grabel, L., "Concise Review: Scientific and Ethical Roadblocks to Human Embryonic Stem Cell Therapy," *Stem Cells 24*:2162-2169, AlphaMed Press (Oct. 2006), published online Jun. 2006.

Harper, J.M. et al., "Axonal growth of embryonic stem cell-derived motoneurons in vitro and in motoneuron-injured adult rats," *Proc. Natl. Acad. Sci. U.S.A. 101*:7123-7128, National Academy of Sciences (2004).

Hong, S.H. et al., "Expression of Estrogen Receptor-α and -β, Glucocorticoid Receptor, and Progesterone Receptor Genes in Human Embryonic Stem Cells and Embryoid Bodies," *Mol. Cells 18*:320-325, Korean Society for Molecular Biology (2004).

Hori, J. et al., "Neural Progenitor Cells Lack Immunogenicity and Resist Destriction as Allografts," *Stem Cells 21*:405-416, AlphaMed Press (2003).

Kerr, D.A. et al., "Human Embryonic Germ Cell Derivatives Facilitate Motor Recovery of Rats with Diffuse Motor Neuron Injury," *J. Neurosci. 23*:5131-5140, Society for Neuroscience (2003).

Klimanskaya. I. et al., "Human embryonic stem cells derived without feeder cells," *Lancet 365*:1636-1641, Lancet Publishing Group (May 2005), published online Mar. 8, 2005.

Mannello, F. and Tonti, G.A., "Concise Review: No Breakthroughs for Human Mesenchymal and Embryonic Stem Cell Culture: Conditioned Medium, Feeder Layer, or Feeder-Free; Medium with Fetal Calf Serum, Human Serum, or Enriched Plasma; Serum-Free, Serum Replacement Nonconditioned Medium, or Ad Hoc Formula? All That Glitters Is Not Gold!," *Stem Cells 25*;1603-1609, AlphaMed Press (Mar. 2007).

McDonald, J.W. et al., "Transplanted embryonic stem cells survice, differentiate and promote recovery in injured rat spinal cord," *Nat. Med. 5*:1410-1412, Nature Publishing Company (1999).

Mudur, G.S., "Big Wonder Cells Mess—Medical research guidelines in India leave doctors free to do what they wish," Internet Citation, [Online], XP002466330, retrieved from the internet at URL:http://www.telegraphindia.com/1051120/asp/opinion/story_5496940.asp> on Nov. 20, 2005.

Reubinoff, B.E. et al., "Neural progenitors from human embryonic stem cells," *Nat. Biotechnol. 19*:1134-1140, Nature America Publishing (2001).

Richards, M. et al., "An Efficient and Safe Xeno-Free Cryopreservation Method for the Storage of Human Embryonic Stem Cells," *Stem Cells 22*:779-789, AlphaMed Press (2004).

Roy, N.S. et al., "Telomerase immortalization of neuronally restricted progenitor cells derived from the human fetal spinal cord," *Nat. Biotechnol. 22*:297-305, Nature Publishing Group (2004).

Schuldiner, M. et al., "Effects of eight growth factors on the differentiation of cells derived from human embryonic stem cells," *Proc. Natl. Acad. Sci. U.S.A. 97*:11307-11312, National Academy of Sciences (2000).

Shi, Q.J. et al., "Novel Role of Human Chorionic Gonadotropin in Differentiation of Human Cytotrophoblasts," *Endocrinology 132*:1387-1395, Endocrine Society (1993).

Skottman, H. and Hovatta, O., "Culture conditions for human embryonic stem cells," *Reproduction 132*:691-698, Bioscientifica Ltd. (Nov. 2006).

Stojkovic, P. et al., "Human-Serum Matrix Supports Undifferentiated Growth of Human Embryonic Stem Cells," *Stem Cells 23*:895-902, AlphaMed Press (Aug. 2005), published online May 11, 2005.

"The Stem Cell 'Miracles'," Internet Citation, [Online], XP-002466331, 5 pages, retrieved from the internet at URL:http://sci.rutgers.edu/forum/showthread.php?t-57401> on May 23, 2006.

Wang, W.-H. and Sun, X.-F., "Human embryonic stem cell lines are contaminated: what should we do?," *Hum. Reprod. 20*:2987-2989, Oxford University Press (Jul. 2005).

Zhang, S.-C. et al., "In vitro differentiation of transplantable neural precursors from human embryonic stem cells," *Nat. Biotechnol. 19*:1129-1133, Nature Publishing Group (2001).

Nikolsky, N.N., et al., "Human Embryonic Stem Cells: Problems and Perspectives," *Citologiâ 49*(7):529-537, Nauka, Russia (2007).

(56) References Cited

OTHER PUBLICATIONS

English Language Abstract of UA 59678 A, published Sep. 15, 2003.

Unverified English Language Translation of UA 71388 A, published Nov. 15, 2004.

Clinical Study Report: Retrospective Study of Human Embryonic Stem Cell (hESC) Therapy in Patients with Spinal Cord Injury (SCI), prepared by Nutech Mediworld, New Delhi, India, dated Nov. 19, 2010.

Co-pending Application, U.S. Appl. No. 13/735,294, inventor Shroff, G., filed Jan. 7, 2013 (Not Yet Published).

Ha, S.Y., et al., "Cryopreservation of human embryonic stem cells without the use of a programmable freezer," *Human Reproduction* 20:1779-1785, Oxford University Press, United Kingdom (2005).

Keirstead, H.S., et al., "Human Embryonic Stem Cell-Derived Oligodendrocyte Progenitor Cell Transplants Remyelinate and Restore Locomotion after Spinal Cord Injury," *The Journal of Neuroscience* 25:4694-4705, Society for Neuroscience, United States (2005).

Mallon, B.S., et al., "Toward xeno-free culture of human embryonic stem cells," *The International Journal of Biochemistry & Cell Biology* 38:1063-1075, Elsevier Ltd., United Kingdom (2006).

Martin, G.P., et al., "The Solubilization of Progesterone by Mixed Bile Salt-Phospholipid Sols," *Chemistry and Physics of Lipids 22*: 227-238, Elsevier/North-Holland Scientific Publishers Ltd., Netherlands (1978).

Nandi, I., et al., "Synergistic Effect of PEG-400 and Cyclodextrin to Enhance Solubility of Progesterone," *AAPS PharmSciTech* 4: 1-5, United States (2003).

Roskams, A.J. & Tetzlaft, W., "Directing stem cells and progenitor cells on the stage of spinal cord injury," *Experimental Neurology* 193:267-272, Elsevier Inc., United Kingdom (2005).

MEDLINE/ NLM, NLM7205230, Abstract of Song, S.Z., et al., "Progestin permeation through polymer membrane V: Progesterone release from monolithic hydrogel devices," *Journal of Pharmaceutical Sciences* 70:216-291, Wiley Liss, Inc., United States (1981).

Trouson, A., "The Production and Directed Differentiation of Human Embryonic Stem Cells," *Endocrine Reviews* 27:208-219, The Endocrine Society, United States (2006).

Adolphe, C. and Wainwright, B., "Pathways to improving skin regeneration," *Exp. Rev. Mol. Med.* 7(20):1-14, Cambridge University Press, England (2005).

Bensidhoum, P.M., et al., "Potentiel thérapeutique des cellules souches mésenchymateuses humaines dans les lésions cutanées radioinduites," *Journal de la Société de Biologie 199*(4):337-341, La Société, France (2005).

Caballero, S., et al., "The many possible roles of stem cells in age-related macular degeneration," *Graefe's Arch. Clin. Exp. Ophthalmol.* 242:85-90, Springer-Verlag, Germany (2004).

Chen, Q., et al., "Surface instillation of stem cell culture in repair of severe skin trauma in guinea pigs," *Chinese Journal of Clinical Rehabilitation* 9(26):228-229, Elsevier B.V., Netherlands (2007) (Abstract Only).

Ho, A.D., et al., "Stem cells and ageing: The potential of stem cells to overcome age-related deteriorations of the body in regenerative medicine," *EMBO Reports* 6:535-538, European Molecular Biology Organization, England (2005).

Li, Y., et al., "Expansion of Human Embryonic Stem Cells in Defined Serum-Free Medium Devoid of Animal-Derived Products," *Biotechnol. Bioeng.* 91(6):688-698, Wiley Periodicals, Inc., United States (2005).

Shi, C., et al., "Stem cells and their application in skin-cell therapy," *TRENDS in Biotechnology* 24(1):48-52, Elsevier Ltd., England (2006).

Smith, L.E.H., "Bone marrow-derived stem cells preserve cone vision in retinitis pigmentosa," *The Journal of Clinical Investigation 114*(6):755-757, American Society for Clinical Investigation, United States (2004).

Yan, G-H., et al., "Experimental study on bone marrow-derived mesenchymal stem cells seeded on HAM facilitating the healing of wound combined radiation injury," *Chinese Journal of Clinical Rehabilitation* 6(14):2072-2073, Elsevier B.V., Netherlands (2007) (Abstract Only).

Office Action mailed Jul. 31, 2013, in U.S. Appl. No. 13/735,294, to Geeta Shroff, filed Jan. 7, 2013.

METHODS OF EXPANDING HUMAN EMBRYONIC STEM CELLS

BACKGROUND OF THE INVENTION

1. Field of the Invention

This present invention relates to pharmaceutical compositions comprising human embryonic stem (hES) cells or their derivatives, said stem cells being free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media, for use in the treatment of presently incurable, terminal and medical diseases, conditions or disorders. More particularly, the invention relates to methods of treatment of clinical disorders and terminal or presently incurable conditions using hES cells via a transplantation protocol. The invention further relates to novel processes of preparing novel stem cell lines which are free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media. This invention further relates to the isolation, culture, maintenance, expansion, differentiation, storage, and preservation of such stem cells.

2. Background Art

A large number of human medical disorders, conditions and diseases are either presently incurable through existing drug therapies, surgery or transplantation methods or they are terminal.

Stem cells have the capacity to divide to generate "daughter" cells that retain the properties of the stem cell, or to produce daughters that begin to differentiate into a more specialized cell type, or to produce one daughter cell of each type. Stem cells are thus central to normal human growth and development, and by their intrinsic characteristics are also potential sources of new cells for the regeneration of diseased or damaged tissue. Stem cells are present at all stages of development, and in many, (possibly most) tissues of the adult. Stem cells from different tissues, and from different stages of development, vary in terms of the number and types of cells to which they normally give rise. The major classes of stem cells according to this classification are embryonic stem cells, somatic stem cells and embryonic germ cells.

At the earliest stages after fertilization (up to the eight cell stage), all cells of the embryo are totipotent (i.e., they have the capacity to develop into every type of cell needed for full development, including extra-embryonic tissues such as the placenta and the umbilical cord). After about two to five days the blastocyst stage is reached. Within this ball of 50-100 cells lies the inner cell mass, which will develop into the embryo proper. The inner cell mass comprises about a quarter of all cells at this stage of development and a unique class of stem cells; the embryonic stem cells. Embryonic stem cells have the innate capacity or potential to differentiate into each of the 200 or so cell types of the body and are described as pluripotent. The capacity of hES cells to contribute to all tissue types in development has not yet been fully established, but they can be grown over long periods of time in culture and expanded in number without changing their cellular genotypes or phenotypes, and maintain their pluripotent state under these conditions.

Beyond the blastocyst stage, stem cells comprise a decreasing proportion of cells in the embryo, fetus and adult body. Many if not most tissues in the fetus and adult contain stem cells, which, in their normal location, have the potential to differentiate into a limited number of specific cell types in order to regenerate the tissue in which they normally reside. These stem cells (somatic stem cells) are multipotent and may have a more restricted potential than embryonic stem cells in that they normally give rise to some but not all of the cell types of the human body. The main sources of somatic stem cells are the fetus and adult bone marrow and cord blood.

Embryonic stem cells serve as an excellent in vitro system for studying cellular differentiation events, drug screening, and as a primary source of specialized differentiated cells for future regenerative therapeutic applications.

The embryonic stem cells, being pluripotent, have the developmental potential to give rise to any differentiated cell type. Thus, a disease that results from the failure or deregulation, either genetic or acquired, of specific cell types is potentially treatable by transplantation of hES cells or their derivatives by replacement of the defective cells and regeneration of the affected organ or tissue and also by stimulating the dormant and the dying tissue.

The transplantation of hES cells or their derivatives into the human body has been suggested to have the potential as a means for addressing unmet medical needs.

It has widely been considered that the transplantation of hES cells will revolutionize the treatment of a wide variety of diseases, conditions and disorders but, to date, studies have been restricted to preclinical studies in mice and primates. It is questionable whether the results observed in animal models are truly representative of the events that would occur upon transplantation of such cells into the human. Furthermore, without clinical usage of the concept, the pharmaceutical compositions, protocols, routes of administration and dosages for administration of the stem cells remain undefined and untested. Furthermore, although human stem cells derived from sources other than an embryo or xenotransplantation of cells, tissues and organs from other species have been used in the clinic; these attempts have been largely unsuccessful or present a variety of debilitating side effects.

The present invention provides for the transplantation of a pharmaceutical composition comprising hES cells and/or their derivatives into humans suffering from a variety of presently incurable or terminal conditions, diseases or disorders.

U.S. Pat. No. 5,453,457 discloses a composition comprising non-murine mammalian pluripotent cells derived from a primordial germ cell and including basic fibroblast growth factor, membrane associated steel factor, soluble steel factor and leukaemia inhibitory factor.

U.S. Pat. No. 6,800,480 claims a composition comprising undifferentiated hES cells proliferating on an extra-cellular matrix.

US Patent Application No. 2003/0017587 discloses in vitro expansion of undifferentiated embryonic stem cells obtained from an aborted fetus or fresh or frozen cleavage stage blastocysts using a culture medium that does not require feeder cells. Once isolated, the embryonic stem cells are introduced into a cell culture medium supplemented with growth factors, fetal bovine serum, neuronal growth factor, leukaemia inhibitory factor, fibroblast growth factor, membrane associated steel factor, soluble steel factor or conditioned media which are not desirable in view of potential side effects upon transplantation into a patient. Also, the said patent application is silent on the protocol to be used for the treatment of genetic or clinical disorders except that the patient requires one dose of each type of cell.

US Patent Application No. 2004/0071665 provides for a therapeutic method employing mammalian stem cells for treatment of cardiopathology. The example provides for embryonic stem cells differentiated to form a cardiomyogenic cluster, cultured on feeder cells and then injected at three sites of the heart of a mouse having myocardial infarction.

US Patent Application No. 2004/0107453 discloses a method for obtaining, maintaining and differentiating adult stem cells and their use in therapeutic treatment.

US Patent Application No. 2005/0124003 discloses a method for obtaining, maintaining and differentiating fetal stem cells and their use in therapeutic treatment.

In particular, and of particular relevance to the present invention, transplantation of embryonic stem cells in mouse models of spinal cord injury (SCI) have clearly demonstrated their future potential as a first line of treatment of acute SCI (McDonald et al., (1999) Nature Med. 5:1410; Kerr et al., (2003) J. Neurosci. 23:5131; Roy et al., (2004) Nature Biotechnology, 22:297; Hori et al., (2003) Stem Cells, 21:405; Harper, (2004) Proc. Natl. Acad. Sci. 101:7123). Despite demonstrated efficacy in animal models, skepticism regarding graft versus host rejection problems, the potential need for lifetime administration of immunosuppressors and tumour and teratoma formation have delayed authorizations to reproduce preclinical safety and efficacy in experimental human trials. A further problem facing the design of clinical studies and of particular relevance to the present invention is that, as yet, there are no established protocols or schedules of administration, there are no studies of what would be a therapeutically effective dose, or active pharmaceutical composition, or what cell types or cell combinations should be used.

It is therefore an object of the present invention to develop pharmaceutical compositions which comprise hES cells and their derivatives which are free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media suspended in a biocompatible solution, carrier or matrix, thus suitable for human use.

Yet another object of the present invention is to develop a protocol for the treatment of presently incurable or terminal disorders.

Still a further object of the present invention is to develop a protocol for the treatment of SCI (Spinal Cord Injury).

The compositions of the present invention are simple to prepare, safe, cost effective, efficient, easily transportable, scalable, have a good shelf life, and are free from side effects such as antibody-antigen reactions, aberrant innervations, tumorigenicity, teratoma formation or graft host rejection. Also, the present invention requires only one embryo and hence the continuous supply of human embryos is not required. Also, the protocol for treatment according to the present invention does not require the use of immunosuppressors, and is not dependent upon HLA typing, is not dependent upon race, gender or age of the treated subject for the effective treatment of the diseases, conditions or disorders, is without regression and is without the need for prior training in the art of administration. Treatment of subjects with the pharmaceutical compositions according to the practice of the present invention is therefore possible at any suitably equipped clinical facility worldwide.

In order to transplant human embryonic stem cells into humans for therapeutic purposes it is important that such cells are free from contamination such as bacteria, viruses, prions or viroids. The adoption of standard operational laboratory practices such as good manufacturing and good clinical practices reduce the risk of such contaminations to an acceptable level.

Risks to the patient exist, however, through existing cell culture methodologies.

A major risk is that components of the cell culture medium, retained in the pharmaceutical product for administration to human subjects are administered and therefore represent a risk to the patient through as yet unanticipated side effects that could not have been anticipated through "safety" studies in animal testing.

Elimination of such risk is therefore desirable.

The characteristics of an embryonic stem cell culture source for administration to human subjects has been identified as having the following design: it is capable of proliferation for an extended period of time without differentiation, maintains a karyotype in which all of the characteristics of the donor are retained faithfully during culture, maintains the potential to differentiate into derivatives of the endoderm, mesoderm and ectoderm throughout the culture, will not differentiate when cultured in the absence of exogenous factors, will not give rise to teratomas, will not be immunogenic, will not form aberrant connections and ectopic tissue, will act on the damaged tissue and not divide continuously in vivo but as they are programmed to do in a natural life cycle. There should be no contaminant present in the culture methodology and the cell line disclosed in the invention.

The major thrust of research until now has been to develop culture conditions that meet these requirements, but to date, no such conditions have been forthcoming or validated through clinical trials. In particular, the research to date has been focused on elimination of the requirement for mouse feeder cells as a matrix for the growth and de-differentiation of a human embryonic stem cell culture. The partial remedy of providing unknown growth factors through the removal of feeder cells and the supplementation of "conditioned media" has also revealed an unacceptable risk in the ideal culture medium. Human embryonic stem cells cultured in the presence of feeder conditioned media still retain an inherent risk of contamination and therefore an unacceptable risk during transplantation into humans.

An additional factor in the design of culture conditions of human embryonic stem cells destined for administration to humans is the question of residual exogenous supplements in the media which may be present in the pharmaceutical composition administered but that are essential during the phase of cellular expansion.

These include basic fibroblast growth factor, leukemia inhibitory factor, membrane associated steel factor, soluble steel factor, serum, albumins or albumin supplements, amino acid supplements, vitamin supplements, transferrins or transferrin supplements, antioxidants, insulin or insulin substitutes, collagen precursors or collagen precursor substitutes, trace elements, residues of "conditioned media", animal products, feeder cells, growth factors, supplementary mineral combinations, amino acid supplements, and vitamin supplements.

Residues of such additional supplements are viewed as unnecessary risks to the safety of patients during the transplantation of human embryonic stem cells into such subjects. In addition, the supplementation of such factors into the culture medium adds to the risk of contamination from the environment and adds to the future cost of stem cell therapy and therefore limits its applicability in a wide range of medical diseases, conditions or disorders.

A number of approaches have been adopted to reduce these risks including: U.S. Pat. and Application Nos. 5,843,780; 5,690,926; 6,642,048; 6,800,480; 5,166,065; 6,200,806; 5,453,357; 6,090,622; 6,562,619; 6,921,632, 2006/0073587 and 2002/076747.

However, none of these approaches offer a system for the production of a pharmaceutical product containing human embryonic stem cells and their derivatives which is free of potentially contaminating factors that could affect the efficacy and safety of human embryonic stem cells and their derivatives upon administration to humans.

It is therefore another objective of the invention to develop a simplified cell culture system for the expansion of hES cells and their derivatives in a substantially undifferentiated state in order to produce a pharmaceutical product that is ready to use in a wide variety of medical disorders.

More particularly, it is an objective of the invention to provide a culture technique which produces a stem cell line free from animal products, feeder cells, growth factors, leukaemia inhibitory factor, supplementary mineral combinations, amino acid supplements, vitamin supplements, fibroblast growth factor, membrane associated steel factor, soluble steel factor and conditioned media.

SUMMARY OF THE INVENTION

The present invention provides pharmaceutical compositions comprising hES cells and/or their derivatives, and for the use of hES cells and their derivatives in treating a wide variety of conditions, diseases and disorders wherein the stem cells are introduced into the human body by a variety of routes of administration, topical applications or intralesional insertion.

The present invention further provides a method for treating a subject suffering from a terminal or presently incurable disease, disorder or condition comprising a schedule of administration of a therapeutically effective amount of hES cells or their derivatives via intramuscular, intravenous, caudal, intravitreous, intrastriatal, intraparenchymal, intrathecal, epidural, retrobulbar, subcutaneous, intracardiac, intracystic, intra-articular or intrathecal injection, epidural catheter infusion, sub arachnoid block catheter infusion, intravenous infusion, via nebulizer, via spray, via intravaginal routes, via local eye and ear drops, and a schedule for administration of the hES cells and their derivatives topically or intralesionally.

It is preferable to use hES cells or their derivatives which are free of animal products, feeder cells, growth factors, leukaemia inhibitory factor, supplementary mineral combinations, vitamin supplements, amino acid supplements, fibroblast growth factor, membrane associated steel factor, soluble steel factor and conditioned media, to avoid any chances of contamination and possibilities of negative side-effects. The hES cells and their derivatives can be obtained through any known and approved cell culture methodology, which is feeder cell free, and free from contamination from any source and safe for human transplantation. hES derivatives include further differentiated cells from the human body.

The present invention further provides pharmaceutical compositions for the treatment of terminal or presently incurable diseases, disorders, or conditions comprising a therapeutically effective amount of hES cells and/or their derivatives, wherein said hES cells or their derivatives are free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media, suspended in a pharmaceutically acceptable biocompatible solution or any other carrier vehicle.

The present invention also includes hES cells and/or their derivatives free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media, entrapped in a biocompatible material or matrix. The biocompatible material or matrix may be selected from biopolymers, including polypeptides or proteins, polysaccharides, including fibronectin, various types of collagen, laminin, keratin, fibrin, fibrinogen, hyaluronic acid, heparin sulfate, chondroitin sulfate, agarose or gelatin.

The compositions of the present invention may be in a ready-to-use drug form in which the stem cells have adequate viability, i.e., they have a viability high enough to be useful in one or more methods of the present invention. In one embodiment, the stem cells have a viability of greater than about 40%, e.g., greater than about 50%, 60%, 70%, or 80%. The compositions may further include an antimicrobial agent, antibacterial agent, hormonal product or other pharmaceutical agent.

In order to prepare the compositions, about 750,000 to about 160 million hES cells and/or one or more of their derivatives such as hematopoietic stem cell progenitors, neuronal stem cell progenitors, mesenchymal stem cell progenitors, insulin producing stem cell progenitors, hepatocyte stem cell progenitors, cardiac stem cell progenitors, epithelial stem cell progenitors or mixtures thereof are suspended in about 0.25 ml to about 100 ml of a carrier vehicle. In one embodiment, about 750,000 to about 80 million hES cells are suspended in about 0.25 ml to about 10 ml of the carrier vehicle. Enrichment for specific differentiated stem cell progenitor types in a population is a priority, although a proportion of undifferentiated stem cells will remain in the composition. In one embodiment, the portion of undifferentiated stem cells will be no more than about 80% of the total population of cells. In another embodiment, the portion of undifferentiated stem cells will be no more than about 40% of the total population of cells.

Terminal diseases and other disorders or conditions that may be treated or ameliorated according to the present invention include, without limitation, cancer, liver and kidney disorders, nervous system disorders, skin disorders, autoimmune disorders, genetic disorders, eye disorders, musculoskeletal disorders, fertility and reproductive disorders and cardiovascular disorders and without limitation include Acute Myeloid Leukaemia, Adenocarcinoma, Arthritis, Astrocytoma, Auditory Nerve Atrophy, Autism, Auto Immune Disorders, Alzheimer's disease, Ankylosing Spondylitis, Becker's Muscular Dystrophy, Brain Damage, Burns, Cerebrovascular Insult, Cerebral Palsy, Coma, Corneal Ulcers, Corneal Graft Rejection, Cortico-Basal Degeneration of the Nervous System, Coronary Artery Disease, Diabetes, Dementia, Downs Syndrome, Duchenne's Muscular Dystrophy, End-Stage Renal Disease, Erb's Palsy, Fascio Scapular Muscular Dystrophy, Fertility Disorders, Friederichs's Ataxia, Heart Failure, Hepatocellular Carcinoma, Hereditary Spino Motor Neuron Disease, Huntington's Chorea, Krabbe's Disease, Limb Girdle Dystrophy, Liver Cirrhosis, Macular Degeneration, Mental Retardation, Multiple Sclerosis, Motor Neuron Disease, Myocardial Infarction, Nephrotic Syndrome, Niemann Pick Disease, Non-Healing Ulceration of the Skin, Olivo-Ponto Cerebellar Atrophy, Optic Nerve Atrophy, Parkinson's Disease, Post Electric Shock Encephalopathy, Post-Rabies Vaccine Encephalopathy, Pressure Sores, Progressive Supranuclear Palsy, Psoriasis, Pthysis Bulbi, Restrictive Cardiomyopathy, Retinitis Pigmentosa, Right Bundle Branch Block, Sarcoidosis, Sinus Bradycardia, Spinal Muscular Dystrophy, Spino Cerebellar Ataxia, Steven Johnson's Syndrome, Systemic Lupus Erythematosus, Thrombocytopenia, Thalassemia, Ulcerative Colitis, Vegetative State, Cystic Fibrosis, Interstitial Lung Disease, Azoospermia, Primary Ovarian Failure, Aphthous Ulcers, Hormone Imbalance, Osteo-Arthritis, Horner's Syndrome and Osteogenic Imperfecta, along with Channelopathy and Hypogammaglobulinemia.

More specifically, the present invention provides a method of treatment of SCI of a subject comprising:
a) administering about 750,000 to about 80 million hES cells and/or their derivatives via sub-cutaneous injection;
b) repeating step (a) after a pre-determined period and thereafter administering hES cells and/or their derivatives via intramuscular injection;
c) administering a therapeutically effective amount of hES cells and/or their derivatives, wherein said cells comprise neuronal stem cell progenitors and hematopoietic stem cell progenitors, via intravenous injection or infusion;
d) administering a therapeutically effective amount of hES cells and/or their derivatives, wherein said cells comprise neuronal stem cell progenitors, via epidural injection and repeating said dose after a pre-determined period depending upon the condition of the subject as assessed by clinical and/or neurological examination;
e) administering a therapeutically effective amount of hES cells and/or their derivatives, wherein said cells comprise neuronal stem cell progenitors, via caudal injection;
f) administering a therapeutically effective amount of hES cells and/or their derivatives, wherein said cells comprise neuronal stem cell progenitors, via intrathecal injection or sub arachnoid block catheter;
g) administering a therapeutically effective amount of hES cells and/or their derivatives, wherein said cells comprise neuronal stem cell progenitors, via epidural injection or epidural catheter;
h) administering a therapeutically effective amount of hES cells and/or their derivatives via deep spinal injection on either side of the spine; and
i) administering a therapeutically effective amount of hES cells and/or their derivatives via intravenous infusion;
wherein steps (a) and (b) are carried out first and the remaining steps may be carried out in any order. In one embodiment, step (f) is repeated followed by step (g), at least once, until the subject exhibits clinical signs of recovery from said SCI.

The invention also provides for a method for treating a subject with a disease, disorder or condition comprising administering a therapeutically effective amount of hES cells and/or their derivatives cultured in media free of animal products, feeder cells, conditioned media, growth factors, leukaemia inhibiting factor, fibroblast growth factor, membrane associated steel factor or soluble steel factor, via intramuscular injection or intravenous injection or epidural injection or epidural catheter or retrobulbar injection or subcutaneous injection or intracardiac injection or intracystic injection or intrathecal injection or by topical application or intralesional application. In one embodiment, the disease, disorder or condition is a terminal or currently incurable disease, disorder or condition.

The invention also provides for a method for treatment of developmental, degenerative, familial and traumatic nervous system disorders and cerebrovascular attack comprising administration of about 750,000 to about 160 million hES cells and/or their derivatives, wherein said cells comprise neuronal stem cell progenitors and hematopoietic stem cell progenitors alone or in combination, via intravenous injection, subcutaneous injection, intramuscular injection, intrathecal injection, epidural catheter infusion and sub arachnoid block catheter infusion.

The invention also provides for a method for treatment of skin disorders comprising administration of about 750,000 to about 160 million hES cells and/or their derivatives, wherein said cells comprise hematopoietic stem cell progenitors, via subcutaneous or intravenous injection.

The invention also provides for a method of treatment of bed sores comprising administration of about 750,000 to about 160 million hES cells and/or their derivatives via local or topical application and via intramuscular injection.

The invention also provides for a method for treatment of auto immune disorders comprising administration of about 750,000 to about 160 million hES cells and/or their derivatives, wherein said cells comprise hematopoietic stem cell progenitors, via intramuscular injection, or intravenous injection, or subcutaneous injection, or intra-articular injection or intravenous infusion or combinations thereof.

The invention also provides for a method for treatment of genetic disorders comprising administration of about 750,000 to about 160 million hES cells and/or their derivatives, wherein said cells comprise neuronal stem cell progenitors and hematopoietic stem cell progenitors alone or in combination, via intravenous injection, subcutaneous injection, intramuscular injection, intrathecal injection, epidural catheter infusion or sub arachnoid block catheter infusion or combinations thereof.

The invention also provides for a method for treatment of gangrene comprising administration of about 750,000 to about 160 million hES cells and/or their derivatives via intravenous injection, intramuscular injection, or local application at the junction of viable and dead tissue or combinations thereof.

The invention also provides for a method for treatment of conditions associated with ageing comprising administration of about 750,000 to about 160 million hES cells and/or their derivatives via intravenous injection, subcutaneous injection, intramuscular injection, or local application in suspension or mixed in a biocompatible carrier such as gel, ointment, matrix, paste or aerosol spray.

The invention also provides for a method for treatment of Diabetes Mellitus comprising administration of about 750,000 to about 160 million hES cells and/or their derivatives, wherein said cells comprise insulin producing progenitor cells, via intravenous or intramuscular injection or combinations thereof.

The invention also provides for a method for treating Cardiovascular Disorders comprising administration of about 750,000 to about 160 million hES cells and/or their derivatives, wherein said cells comprise hematopoietic stem cell progenitors, via intravenous injection, subcutaneous injection, intramuscular injection, intracardiac injection, angiography or direct injection during surgery.

The invention also provides for a method for treatment of Liver and Kidney Disorders comprising administration of about 750,000 to about 160 million hES cells and/or their derivatives, wherein said cells comprise hematopoietic stem cell progenitors, albumin producing stem cell progenitors and bilirubin producing stem cell progenitors, via intravenous injection, subcutaneous injection, intramuscular injection, intravenous infusion, or local injection.

The invention also provides for a method for the treatment of Fertility and Reproductive Disorders comprising administration of about 750,000 to about 160 million hES cells and/or their derivatives, wherein said cells comprise hematopoietic stem cell progenitors, via local intramuscular injection, intratesticular injection or through subcutaneous skin injection near the epididymis.

The invention also provides for a method for the treatment of Musculoskeletal Disorders comprising administration of about 750,000 to about 160 million hES cells and/or their derivatives, wherein said cells comprise neuronal stem cell progenitors and hematopoietic stem cell progenitors alone or in combination, via intravenous injection, subcutaneous injection, intramuscular injection or intravenous catheter infusion.

The invention also provides for a method for the treatment of Eye Disorders comprising administration of about 750,000 to about 160 million hES cells and/or their derivatives, wherein said cells comprise neuronal stem cell progenitors, hematopoietic stem cell progenitors and mesenchymal stem cell progenitors alone or in combination, via local intravenous injection, subcutaneous injection, intramuscular injection, retrobulbar injection, intravitreous injection or topical application. In one embodiment, about 750,000 to about 160 million hES cells and/or their derivatives comprising neuronal stem cell progenitors are administered via retrobulbar injection. In another embodiment, about 750,000 to about 160 million hES cells and/or their derivatives comprising neuronal stem cell progenitors are administered via intravitreous injection. In another embodiment, about 750,000 to about 160 million hES cells and/or their derivatives comprising mesenchymal stem cell progenitors are applied to contact lenses for placement on the eye for the treatment of corneal abrasion (e.g., the contact lens is cultured with the hES cells and/or their derivatives to coat the contact lens with cells and the lens is then placed on the eye for about 24 hours).

The invention also provides a method for treatment of Lung Disorders comprising the administration of 750,000 to 160 million hES cells and/or their derivatives wherein said cells comprise hematopoietic stem cell progenitors alone or in combination with neuronal stem cell progenitors via intramuscular injection, intravenous injection, spray, or nebulizer. In one embodiment 750,000 to 160 million hematopoietic stem cell progenitors are administered via nebulizer in which 2 ml of normal saline is added. In another embodiment 750,000 to 160 million hematopoietic stem cell progenitors are administered via spray (puff).

The invention also provides a method for the treatment of Hormone Disorders comprising the administration of 750,000 to 160 million hES cells and/or their derivatives wherein said cells comprise hematopoietic and neuronal stem cells via intramuscular and intravenous routes.

The invention also provides a method for the treatment of Aphthous Ulcers and other ulcers comprising the administration of 750,000 to 160 million hES cells and/or their derivatives wherein said cells comprise hematopoietic and neuronal stem cells in combination or alone via intramuscular and intravenous routes.

The invention also provides a method for the treatment of Osteo-arthritis of the knee and hip joint comprising the administration of 750,000 to 160 million hES cells and/or their derivatives via intramuscular, intravenous or intra-articular injection. In one embodiment 750,000 to 160 million hematopoietic stem cell progenitors are administered intra-articularly.

The present invention provides a cell culture methodology that is applicable to the culture of hES cells and their derivatives that can be used for transplantation in humans without any side effects such as teratoma formation, tumor formation, antigenicity problems or graft-versus-host rejection.

The design of the culture methodology is specifically for the production of hES cells and their derivatives of sufficient viability and of appropriate characteristics for therapeutically optimal activity after transplantation in humans.

In a preferred embodiment, the cell culture methodology is used for the growth, expansion, differentiation and storage of hES cells. In addition, the invention relates to ready to inject compositions comprising hES cells and/or their derivatives that are stored in conditions of storage that are suitable for direct transplantation on thawing.

In contrast to existing cell culture methodologies for the maintenance of hES cells in a substantially undifferentiated state, the culture medium does not contain supplements such as basic fibroblast growth factor, leukemia inhibitory factor, membrane associated steel factor, soluble steel factor, serum, albumins or albumin supplements, amino acid supplements, vitamin supplements, transferrins or transferrin supplements, antioxidants, insulin or insulin substitutes, collagen precursors or collagen precursor substitutes, trace elements, residues of "conditioned media", animal products, feeder cells, growth factors, supplementary mineral combinations, amino acid supplements, and vitamin supplements.

In further contrast to other cell culture methodologies for the expansion of hES cells, the practice of the present invention does not lead to the formation of embryoid bodies, thereby avoiding the need for surgical dissection. It is worth noting at this point that the product of the invention being a totally human product, xenotransplantation (e.g., animal testing) may not be necessary. The instance of the first in vitro fertilization (IVF) gestation is a corollary example.

Unlike other cell culture methodologies, the cell culture techniques of the present invention allow for nearly unlimited expansion of hES cells without significant differentiation. A major advantage of the present invention is that a single embryo is sufficient to provide therapeutically effective amounts of hES cells and/or their derivatives to treat multitudes of patients. Thus, there is no need for repeated procurement of human embryos, and many of the ethical questions associated with the use of human embryos may be avoided.

A further advantage of the methods of the present invention is that the hES cells and their derivatives are universally acceptable products in immunological terms, so no cross-matching of patients and cells is required and no immunosuppression is needed.

One aspect of the invention relates to methods for isolating hES cells, comprising:
(a) collecting a 2 to 7 day old embryo in minimal essential medium,
(b) isolating hES cells from the embryo by mechanical means.

One aspect of the invention relates to a method of expanding human embryonic stem cells free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media, comprising the steps of:
(a) introducing human embryonic stem cells in a cell medium consisting of minimal essential medium, a progestin and a β-human chorionic gonadotropin (βhCG) agonist; and
(b) incubating the stem cells at a temperature of about 34° C. to about 38° C. in an environment of about 3.5% to about 6% carbon dioxide for about 12 hours to about 48 hours.

Another aspect of the invention relates to methods of growing hES cells such that they are at a stage prior to the partially differentiated stage and are free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media, comprising the steps of:
(a) introducing hES cells in a cell culture medium consisting of minimal essential medium; and
(b) incubating the stem cells at a temperature of about 34° C. to about 38° C. in an environment of about 3.5% to about 6% carbon dioxide for about 12 hours to about 48 hours.

Another aspect of the invention relates to a process of preparing a ready to use human embryonic stem cell preparation for human transplantation comprising:
(a) obtaining human embryonic stem cells free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media,
(b) centrifuging said stem cells to obtain a pellet, and
(c) suspending the pellet in a biocompatible solution.

Another aspect of the invention relates to a method of storing a human embryonic stem cell in a viable condition comprising
(a) taking stem cells prepared by the methods of the present invention,
(b) adding a cryopreservation agent, and
(c) freezing the cells at −4 to −80° C.

The purpose of growing hES cells according to the practice of the present invention in the absence of such supplements is to reduce the risk of introducing bacterial, fungal, viral or other contaminations into the culture. This reduces the risk of infection and variability in the characteristics of the cells.

A further purpose of the present invention is to provide simple, cost effective, scaleable methods for the production and expansion of hES cells and their derivatives in a form that is free from any contaminating residues and is safe for use in humans.

The purpose of this invention is therefore to provide pharmaceutical products in which the risk of administration of all co-contamination is reduced, and in which residual contamination of supplementary factors is eliminated.

A further purpose of the present invention is to provide a cell culture methodology that reduces the risk of chromosomal aberrations or genetic instability.

A further purpose of the present invention is to provide a cell culture methodology that reduces the risk of teratoma formation in patients in which said culture is transplanted.

A further purpose of the present invention is to provide a cell culture methodology that reduces the risk of tumour formation in patients in which said culture is transplanted.

A further purpose of the present invention is to provide a cell culture methodology that reduces the risk of antigenicity problems or graft versus host rejection problems in patients in which said culture is transplanted.

The present invention specifically provides compositions comprising hES cells and their derivatives and a biocompatible medium that are in a form that is in compliance with international regulatory standards of safety and quality, and therefore in a form that is ready for injection into human patients for therapeutic purposes.

The present invention also provides a product of manufacture comprising a suspension of hES cells and/or their derivatives suspended in a biocompatible solution and contained in a container for storage, transport or transplantation directly into a human.

The present invention also provides a method for the expansion of hES cells and their derivatives.

The present invention also provides a method for the expansion of hES cells and their derivatives and inhibition of their differentiation.

The present invention also provides a method for the growth of hES cells and their derivatives that renders them therapeutically effective upon transplantation into a human that is suffering from a disease, condition or disorder.

DETAILED DESCRIPTION OF THE INVENTION

Definitions

In the description and examples that follow, a number of terms are used herein. In order to provide a clear and consistent understanding of the specification and claims, including the scope to be given such terms, the following definitions are provided.

It may be noted that the terms used to generally describe the present invention are used in a manner in keeping with their common meaning as understood by one of ordinary skill in the art.

"Embryonic stem cell" refers to pluripotent cells of humans (i.e., hES cells). In one embodiment, the hES cells are isolated from a pre-blastocyst stage embryo. In another embodiment, the hES cells are prepared by dedifferentiation of at least partially differentiated cells (e.g., multipotent cells) and are totipotent in practice. Methods of preparing hES cells are well known and taught, for example, in U.S. Pat. Nos. 5,843,780, 6,200,806, 7,029,913, 5,453,357, 5,690,926, 6,642,048, 6,800,480, 5,166,065, 6,090,622, 6,562,619, 6,921,632, and 5,914,268, U.S. Published Application No. 2005/0176707 and International Application No. WO2001085917.

"Fetal stem cells" refers to the stem cells derived from the fetal tissue, i.e., tissues of a developing human after implantation of the embryo in the uterus.

"Multipotent" refers to stem cells that can produce only cells of a closely related family of cells.

"Pluripotent" refers to stem cells that are the descendants of totipotent cells and can grow into any cell type except for totipotent stem cells.

"Totipotent" refers to stem cells that are produced from the fusion of an egg and sperm cell. Cells produced by the first few divisions of the fertilized egg cell are also totipotent. These cells can grow into any type of cell without exception.

"Therapeutically effective amount" is used in the specification to describe concentrations or amounts of components such as embryonic stem cells, neuroprogenitor cells, neuronal cells, hematopoietic stem cell progenitors, cardiac stem cell progenitors, or any other derivative of stem cells, or other agents and mixtures thereof which are effective for producing an intended result within the context of practicing one or more aspects of the present invention.

The terms "transplanting" and "transplantation" are used throughout the specification synonymously to describe the process by which embryonic stem cells and/or their derivatives according to the present invention are delivered to the site within the human body where the cells are intended to exhibit a favorable effect in connection with the treatment or amelioration of a disease, disorder or condition described herein including, without limitation, for repairing damage to a subject's central nervous system, treating a neurodegenerative disease or treating the effects of nerve damage caused by stroke, cardiovascular disease, a heart attack or physical injury or trauma or genetic damage or environmental insult to the brain and/or spinal cord or other organs, caused by, for example, an accident or other activity, liver damage, autoimmune disorder, sexual or reproductive dysfunction, degeneration of various parts of the eye, kidney damage, etc.

"Biocompatible solution" is used in the specification to refer to solutions in which the hES cells and/or their derivatives are suspended for use in the protocol for transplantation or for any other subsequent uses. Such biocompatible solutions include saline and may further comprise other ingredients such as preservatives, antimicrobials, and the like and other pharmaceutical agents.

"Biocompatible carrier" is used in the specification to refer to solid carriers, solutions and mixtures in which the hES cells and/or their derivatives are suspended for use in the protocol for topical treatment, transplantation or for any other subsequent uses. Such biocompatible carriers include gels, ointments, pastes, and aerosol sprays.

"Biocompatible container" is used in the specification to refer to containers (e.g., cell culture or storage containers) in which the hES cells and/or their derivatives are placed and which do not prevent the cells from being used in transplantation, i.e., do not contaminate the cells with compounds which cannot be administered to subjects. Examples of biocompatible container materials include without limitation glass, stainless steel, and polystyrene.

A "progestin" is any natural or synthetic hormone having progesterone-like activity, i.e., having at least 25% of the activity of progesterone in one of any known assay for biological activity. Examples include without limitation progesterone, dydrogesterone, medroxyprogesterone, norethisterone, levonorgestrel, norgesterel, gestodene, and drospirenone. Examples of other progestins are disclosed in U.S. Pat. Nos. 7,091,234, 7,084,151, 7,081,457, 7,071,205, 6,562,857, 6,319,911, 6,245,757, 6,043,235, and 6,028,064.

"β-human chorionic gonadotrophin (βhCG) agonists" are defined as any naturally occurring or synthetic βhCG or fragment or derivative thereof having at least 25% of the activity of natural βhCG in one of any known assay for biological activity. Examples of βhCG agonists include without limitation βhCG and those disclosed in U.S. Pat. Nos. 6,635,445, 6,585,982, 6,583,109, 6,469,139, and 5,997,871.

"Minimal essential medium" is used in the specification to refer to a cell culture medium comprising amino acids, salts, glucose and vitamins. Examples include RPMI, DMEM, EMEM, and GMEM.

"Nebulization" means the administration of a drug or substance into the lungs via the nebulizer.

Intra-articular means administration into the intra-articular space.

Retrobulbar means administration into the retrobulbar space.

Intravenous infusion means administration into the vein by using an iv fluid comprising the product or drug.

"Epidural" injection or catheter infusion means administration into the region outside the dura mater of the meninges.

"Intrathecal" injection or catheter infusion means administration into the innermost layer of the meninges, that is, the arachnoid matter into the cerebro spinal fluid, which is in continuum with the brain.

"Caudal" injection means administration through the sacral membrane, which is approximately three centimeters above the tip of the coccyx which is in continuum with the epidural space.

"Deep Spinal Injection" means injection into the erector spinal muscles on either side of the spine.

"Intramuscular" injection means administration in between the muscle sheets.

"Intravenous" injection means administration inside a vein.

"Acute SCI" means up to three months after the date of the SCI.

"Sub Acute SCI" means from three months after the date of SCI to up to nine months after the date of the injury.

"Chronic SCI" more than nine months after the date of the SCI.

"Derivatives" of hES cells include multipotent stem cells, pluripotent stem cells, adult stem cells and tissue specific stem cells and do not include fully differentiated cells. Examples of tissue specific stem cells may be found in the following table.

| Cell Type | Pat. No. |
| --- | --- |
| Adipose-derived stem cell | 6,777,231 |
| Breast epithelial stem cells | 5,814,511 |
| Endothelial stem cells | 6,852,533 |
| Dorsal root ganglion progenitor cells | 6,835,567 |
| Hematopoietic progenitor cells CD34$^-$, CD7$^+$, Lin$^-$, Lin$^-$, CD45RA$^+$, | 6,537,807 |
| Hematopoietic stem cells Thy-1$^+$ | 5,061,620 |
| Hematopoietic stem cells Thy-1$^+$, CD34$^+$ | 5,750,397 |
| Hematopoietic stem cells CD34$^+$, CD38$^-$, HLA-DR$^+$ | 5,840,580 |
| Hematopoietic lymphoid and dendritic cells CD34$^+$, CD45RA$^+$, CD10$^+$; Hematopoietic dendritic cells CD34$^+$, CD45RA$^+$, CD10$^+$, | 5,972,627 |
| Hematopoietic stem cells c-kit$^-$, Thy-1$^-$ | 5,876,956 |
| Hematopoietic stem cells CD34$^+$ | 5,681,559 |
| Hematopoietic stem cells HCC-1$^+$ | 5,677,136 |
| Hematopoietic progenitor cells CD34$^+$, galactose-specific lectin$^+$ | 5,858,782 |
| Hematopoietic stem cells (quiescent) CD34$^+$ | 5,807,686 |
| Keratinocyte stem cells | 6,485,971 |
| Liver stem cells | 6,129,911 |
| Do not express OC2 | 6,872,389 |
| Lymphohematopoietic progenitor stem cells My10$^-$ | 5,256,560 |
| Lymphoid progenitor cells | 6,908,763 |
| Mesencephalon neural progenitor cells | 6,913,925 |
| Mesenchymal stem cells CD45$^+$ | 6,387,367 |
| Mesenchymal stem cells | 5,486,359 |
| Mesenchymal stem cells | 5,827,735 |
| Mesenchymal stem cells | 5,908,782 |
| Mesenchymal stem cells | 6,936,281 |
| Mesenchymal stem cells | 6,908,764 |
| Mullerian duct-derived pluripotent epithelial cells | 6,416,999 |
| Myeloid progenitor cells c-kit$^{hi}$, IL-7Rα$^-$ | 6,465,247 |
| Myeloid progenitor cells Thy-1$^-$, IL-7Rα$^-$ | 6,761,883 |
| Neural progenitor cells | 5,753,505 |
| Neural stem cells | 5,851,832 |
| Neuronal progenitor cells | 6,251,669 |
| Neuronal stem cells | 6,969,608 |
| Neuronal progenitor cells that do not express a Hu protein | 6,852,532 |
| Lineage-restricted neuronal precursor cells E-NCAM$^+$ | 6,734,015 |
| Neuroepithelial stem cells | 7,037,702 |
| Central nervous system neural stem cells | 5,968,829 |
| Neuronal progenitor cells | 6,812,027 |
| Neural progenitor cells | 6,913,925 |
| Central nervous system neuron-restricted precursor cells | 6,787,353 |
| Ventral mesencephalon neuron progenitor cells | 5,411,883 |
| Neural crest stem cells | 5,589,376 |

-continued

| Cell Type | Pat. No. |
|---|---|
| Neural crest multipotent cells containing RET protein | 6,890,724 |
| Neutrophil precursor cells | 5,955,357 |
| Pancreatic progenitor cells | 6,436,704 |
| Pancreatic islet progenitor cells Express ErbB2 | 6,753,153 |
| Pluripotent cells | 5,914,268 |
| Pluripotent cells transformed with a HOX11 gene | 5,874,301 |
| Peripheral blood progenitor cells | 5,541,103 |
| Renal stem cells | 6,410,320 |
| Renal stem cells | 6,458,588 |
| Retinal stem cells | 6,117,675 |
| Skeletal progenitor cells | 6,517,872 |
| Stem cells $FGFR^+$, not ES cells | 6,767,737 |
| Stem cells which give rise to blood cells $CD34^-$, $MHC-I^-$, $MHC-II^-$ | 5,744,347 |
| T lineage progenitor cells $CD8^{int}$, $CD4^{int}$, c-kit$^{hi}$, high bcl-2; $CD8^{lo}$, $CD4^{lo}$, c-kit$^{hi}$, high bcl-2 | 5,821,108 |
| T lymphocyte precursor cells $CD34^+$, $CD7^+$, Leu $8^+$ | 5,622,853 |

This present invention relates to pharmaceutical compositions comprising hES cells and/or their derivatives, said stem cells being free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media, for use in the clinical treatment of presently incurable or terminal diseases, conditions or disorders. In another embodiment, the invention relates to a method of treatment of presently incurable or terminal conditions using hES cells and/or their derivatives via a transplantation protocol.

The phrase "free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media" does not exclude the trace amounts of progestin and βhCG agonist that may be present in the pharmaceutical composition as a result of the culturing methods of the present invention. The term "animal products" refers to any non-human product.

In another embodiment, the process of this invention provides a simple, safe, broadly applicable, reproducible and efficient method for transplantation of a pharmaceutical composition comprising hES cells and/or their derivatives in a ready to use form and being free of feeder cells and any other contamination. These cells may be derived from any culture methodology and transplanted into the human body irrespective of the patient's genetic background, age, race and gender and without antibody-antigen reaction or graft-host rejection, without the formation of teratomas or tumors, or other debilitating side effects, without the result of aberrant innervations and without the need for administration of immunosuppressors for the treatment of a variety of diseases, conditions and disorders.

In contrast to other known methods, the hES cells used in the preparation of the pharmaceutical compositions of the present invention are grown in a culture medium which is free of animal products, feeder cells, growth factors, leukaemia inhibitory factor, supplementary mineral combinations, amino acid supplements, vitamin supplements, fibroblast growth factor, membrane associated steel factor, soluble steel factor and conditioned media, and therefore do not have any sort of contamination which may interfere with the safety or efficacy of the intended clinical use.

According to the practice of the invention, hES cells and/or their derivatives are introduced into the human body by intramuscular, intravenous, caudal, intravitreous, intrastriatal, intraparenchymal, intrathecal, epidural, retrobulbar, subcutaneous, oral, intracardiac, intracystic, intra-articular or intrathecal injection or epidural catheter, sub arachnoid block catheter, intravenous infusion, via nebulizer, via spray, via intravaginal routes, and/or via local eye and ear drops. In another embodiment, the hES cells and/or their derivatives are administered topically or intralesionally.

Each route of administration uses a particular volume for injection and therefore a specific range of cells from the stock solutions of hES cells and/or their derivatives as indicated in Table 1. Where cell types are indicated (e.g., in the injection schedule tables below), the indicated cell type is the type that is predominantly present in the cell population.

TABLE 1

| Route of administration | Volume | Cell number |
|---|---|---|
| intramuscular | 0.25 ml | 750,000-1.5 million |
| intravenous | 0.25 ml | 750,000-1.5 million |
| subcutaneous | 0.25 ml | 750,000-1.5 million |
| caudal | 2 ml | 6-16 million |
| epidural | 2 ml | 6-16 million |
| intrathecal | 2 ml | 6-16 million |
| intra-articular | 2 ml | 6-16 million |
| retrobulbar | 2 ml | 6-16 million |
| epidural catheter | 4-5 ml | 12-40 million |
| intravenous infusion | 0.75 ml | 2.25-4.5 million |
| nebulizer | 2 ml | 6-16 million |
| intravaginal | 2 ml | 6-16 million |

In between the laboratory and the ultimate point of use, whether it be a clinic or elsewhere, the pharmaceutical compositions must be kept in cold storage. In one embodiment, the pharmaceutical compositions are stored at about +4 to about −160° C. In another embodiment, the pharmaceutical compositions are stored at about −15 to about −72° C., e.g., about −20 to about −40° C.

In one embodiment, the hES cells used in the present invention are isolated from a spare embryo, discarded from a natural in vitro fertilization cycle and donated through informed consent. In an alternate embodiment, pluripotent fetal stem cells, such as those described in U.S. Published Application No. 2005/0124003 isolated from chorionic villus, amniotic fluid and/or placenta, are used in the present invention.

This invention provides a method for treatment of a variety of diseases, conditions and disorders including but not limited to cancer, stroke, genetic disorders, liver disorders, nervous system disorders, vascular disorders, skin diseases and disorders, autoimmune disorders, eye disorders, kidney disorders, cardiac disorders, musculoskeletal disorders, reproductive and fertility disorders, and arthritis using hES cells and/or their derivatives.

Non-limiting examples of cancers which may be treated according to the present invention include spinal cord tumor, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, cervical cancer, metastatic lesions, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

In one embodiment, the hES cells are not treated with a differentiating agent since, being embryonic, the cells are programmed, and once administered to the subject, the cells migrate to the site of the lesion. At that site, the cells differentiate in response to in vivo differentiation signals. At the site of the lesion, the hES cells and their derivatives do not proliferate indefinitely, thereby necessitating a schedule of repeated injections. The fact that the hES cells and their derivatives do not proliferate indefinitely eliminates the possibility of tumorigenicity and teratoma formation.

After treatment with hES cells and/or their derivatives according to the practice of the present invention, the patient should take rest and adopt a strict regimen of abstinence from the intake of any substance such as alcohol or tobacco that may impair cellular function and impede the regeneration processes triggered by migration of the hES cells and their derivatives to the site of the lesion. The patient should also avoid taking any medications that are known to be harmful during pregnancy, as the medications may have adverse effects on the transplanted cells.

Use of hES Cells and their Derivatives in the Treatment of SCI

At present there are no effective cures for the treatment of SCI including Acute Spinal Cord Damage, Subacute Spinal Cord Damage or Chronic Spinal Cord Damage, which frequently results in paraplegia, tetraplegia and quadriplegia. The transplantation of hES cells for the treatment of SCI presents a unique opportunity to address an unmet medical need and dramatically improve the lives of the millions of people worldwide who suffer the consequences of SCI. Regaining lost functions of the central and autonomic nervous systems through the transplantation of hES cells and their derivatives in a substantially progenitor state will allow recovery of parasympathetic, sympathetic, motor, autonomic and sensory pathways through the replacement of lost cell function, regeneration of lost neural cells, removal of physical barriers such as scar tissue, blocking of inhibitory signaling pathways and the release of neurotrophic factors from the transplanted hES cell progenitors.

Amongst the benefits of restoration of neurological function through the transplantation of hES cells according to the practice of the present invention are: an improvement in motor and sensory function, the general quality of life, reduction in the support system generally provided by relatives, decrease in dependency upon other pharmaceutical compositions, and other medical devices and aids, improvement in the mental and psychological status and also in economic independence. There is a reduction in costs of medical equipment and disability aids and medication dependence through a recovery of the parasympathetic, sympathetic, sensory, and motor functions. There is an enhancement in self-sufficiency, improvement in social status, marital status and ability to exercise reproductive rights, with only a limited number of clinic visits per annum for treatment. Treatment by the administration of hES cells and their derivatives according to the present invention does not lead to problems of antigenicity, tumour formation, teratoma formation or aberrant neural connections.

Also, administration of hES cells and their derivatives especially for SCI subjects results in the cure of bed sores, reduction in their need for hypertensives or anti-depressants, restoration of bladder sensation and control, restoration of bowel sensation and sensation of pain and touch; restoration of lost reflexes; reduction in symptoms of cold sweats; reduction in the sensation of giddiness; normalization of blood pressure and normalization of breathing with full diaphragmatic involvement.

A procedure for the administration of hES cells to patients suffering Sub-acute Spinal Cord Damage, or Chronic Spinal Cord Damage and for whom natural recovery mechanisms have failed is given in detail below. A different procedure for the treatment of Acute SCI as a first line of treatment within three months of the injury according to the practice of the present invention is also provided in detail below.

The therapeutically effective dosage, the schedule of administration and route of administration of hES cells to be administered primarily depends upon three factors; namely type of disorder, clinical status of the patient and the severity of the symptoms present During the practice of the present invention it has been found that therapeutically effective dosages and schedules are not dependent upon age, gender, body weight or race. The protocol for each patient is individually established based on an ongoing process of evaluation of the patient.

In one embodiment of the practice of the present invention, a pharmaceutical composition containing hES cells and/or their derivatives is administered to a subject that is suffering from a presently incurable disorder or terminal condition or other clinical disorder as referred to above through a series of injections in order to treat the disorder.

Various embodiments for the treatment of clinical disorders and terminal conditions according to the present invention will now be described with reference to the following examples.

Treatment, Dosage, Schedule, Routes of Administration, Evaluation and Follow Up of Patients Suffering from SCI In one embodiment, hES cells and/or their derivatives are administered to a subject that has suffered from a SCI for more than three months (Sub Acute and Chronic SCI) through a series of injections in order to treat the disorder. In another embodiment, the hES derivatives are hematopoietic progenitor stem cells. In another embodiment, the hES derivatives are neuronal progenitor stem cells.

Test Dose

In one embodiment, about 750,000 to about 80 million hES cells and/or their derivatives, wherein said cells comprise hematopoietic progenitor stem cells and neuronal progenitor stem cells, diluted in sterile normal saline to a final volume of about 0.25 to about 1.0 ml are tested for contamination and viability and for count using standard protocols and thereafter are administered by subcutaneous injection as a test dose in the forearm. Observations are made to check for anaphylactic shock, pain or inflammation at the site of the injection, generalized itching, flushing or fever after five minutes, ten minutes, fifteen minutes, thirty minutes, one hour and twenty four hours. In one embodiment, the proportion of hES cells to hematopoietic progenitor stem cells and neuronal progenitor stem cells ranges from about 4:1 to about 1:4. In another embodiment, the proportion is about 1:1.

Priming Dose

The protocol entails the administration of a subcutaneous, intramuscular and/or intravenous priming injection of a pharmaceutical composition containing about 750,000 to about 80 million hES cells and/or their derivatives, wherein said cells comprise hematopoietic progenitor stem cells and neuronal progenitor stem cells, resuspended in a volume of about 0.25 ml to about 1.0 ml of sterile normal saline. The priming injection is administered through an injection of a pharmaceutical composition containing the same number of hES cells and their derivatives daily for one week to 10 days.

Epidural Injection and Epidural Catheter

About 750,000 to 80 million hES cells and/or their derivatives, wherein said cells comprise neuronal progenitor stem cells, suspended in a volume of 2 ml of sterile normal saline and further diluted to 5 ml to 40 ml of sterile normal saline is administered by epidural injection or epidural catheter above or below the site of the lesion twice daily over a period of three consecutive days, seven to ten days after the first priming injection. Administration by epidural injection/epidural catheter is repeated above or below the site of the lesion according to the clinical progress in the improvement of symptoms presented by the patient and the opinion of the physician. It has also been observed that if the patient is made to lie on his/her back after the epidural injection, sensory improvement is substantial and if he/she is made to lie in the face-down position, the motor improvement is substantial. In both cases, the patient has to have the legs kept in an elevated position.

Intrathecal

About 750,000 to 11 million hES cells and/or their derivatives, wherein said cells comprise neuronal stem cell progenitors, suspended in 2 ml of sterile normal saline and further diluted by 2 ml of sterile normal saline to a total volume of 4 ml are administered by intrathecal injection above or below the site of lesion at periods of two, five, eight, twelve, seventeen and twenty two months after the start of the priming injections.

In one embodiment, the SCI treatment is continued by administering cells by epidural injection via catheter above or below the site of the lesion, e.g., fifteen days after the injury. In one embodiment, a suspension of about 750,000 to 80 million hES cells and/or their derivatives, wherein said cells comprise neuronal stem cell progenitors, in a volume of 2 ml of sterile normal saline and then further diluted into 15 ml to 40 ml of sterile normal saline is injected. This treatment may be repeated one and a half months later.

Deep Spinal Injection

According to the observed progress in symptom reversal, additional booster injections of the pharmaceutical composition may be administered comprising about 750,000 to about 80 million hES cells and/or their derivatives, wherein said cells comprise both hematopoietic stem cells and neuronal progenitor stem cells, suspended in a volume of 0.25 ml to 1.0 ml of sterile normal saline. In one embodiment, the pharmaceutical composition is administered by deep spinal injection at the back of the spine weekly or every other week. This treatment will strengthen the back muscles and enhance physical rehabilitation once the patient has regained mobility.

Caudal Injection

According to the practice of the present invention, a pharmaceutical composition of about 750,000 to about 80 million hES cells and/or their derivatives, wherein said cells comprise neuronal stem cell progenitors, resuspended in 2 ml of saline and diluted into 10 ml alone or in combination with up to 20 ml of DEPOMEDROL (methylprednisolone acetate) are administered by caudal injection. This treatment will strengthen the muscles of the lumbar region and allow for regaining of sensory and motor power in the lumbar and sacral areas.

In addition to ongoing transplantation of hES cells, the recovery of the patient is aided by daily physiotherapy and a re-education in their use of lost motor function and instruction on maintaining a healthy lifestyle that promotes cellular function and cellular regeneration processes.

Local Administration

In addition to the direct treatment of SCI using hES cells and/or their derivatives according to practice of the present invention, bed sores arising as a result of long term immobilization of the patient may be treated rapidly and effectively through the topical application of a pharmaceutical composition containing hES cells and/or their derivatives.

Treatment of bed sores may be achieved by topical application of a pharmaceutical composition containing about 750,000 to about 160 million hES cells and/or their derivatives, wherein said cells comprise hematopoietic progenitor cells. Loading or priming doses are given by intravenous and intramuscular injection to allow for internal healing as well as to promote neo-vascularisation. Alternatively, the hES cells and their derivatives are resuspended in 2 ml saline, diluted with 2 to 4 ml of saline and applied intralesionally.

Intravenous Infusion

According to the practice of the present invention, a pharmaceutical composition comprising 750,000 to 80 million hES cells and/or their derivatives, wherein said cells comprise hematopoietic and neuronal progenitor cells, are resuspended in 100 ml of normal saline and administered by the intravenous route. This treatment insures a continuous flow of stem cells into the body and can be especially useful if the other direct routes are not accessible due to any reason, e.g., a bed sore at the site, patient too debilitated, etc.

Protocol for Treatment of Acute SCI

Rapid intervention in the treatment of Acute SCI greatly enhances the chances of survival of the patient. Furthermore, rapid intervention in the treatment of any incurable disease, condition or disorder through practice of the present invention increases the chances of recovery. In a further embodiment of the present invention, patients suffering from Acute SCI for less than three months after spinal injury can also be treated successfully as described in detail below. A pharmaceutical composition of hES cells and/or their derivatives along with an effective physiotherapy, rehabilitation and re-education program according to the practice of the present invention is an effective first line of treatment for Acute SCI.

Treatment of Acute SCI comprises all of the steps used for treatment of Sub Acute and Chronic SCI plus two additional steps. During the initial intervention for the SCI immediately after the injury occurs (e.g., surgery), hES cells and/or their derivatives are administered directly to the site of the injury. Follow-up treatment comprises two intrathecal injections and one epidural injection within three months of the injury.

Clinical Evaluation and Observations

For patients that have lost motor function in their legs for an extended period of time, while being treated according to the present invention, programs for their re-education in walking and other physical therapy should be implemented as motor function returns to their legs. As a first step in such programs, the use of walking frames and calipers has proven effective in re-education. An additional program of muscularisation of the arms and upper body should be implemented in order for the patient to be able to support their body weight unaided in the walking. The re-education programs may be reduced as the treatment continues and the condition of the patient improves.

In addition to the reduction in the need for medical device support and physical therapy, because of improvements in the sympathetic and parasympathetic symptoms of the patient, through treatment according to the practice of the present invention, there is a reduction in the requirement for medications, including blood pressure fluctuation medication, depression medication, bed-sore medication, medication and medical devices for bowel and bladder complications, anti-spasticity medications and pumps.

In addition to a reduction in the need for medications for the treatment of symptoms directly or indirectly associated with the SCI, it is observed that diabetics with SCI and treated according to the present invention show a reduction in the need for their anti-diabetic medications.

Clinical evaluation of the progression in improvement of the symptoms presented by the patient suffering from SCI and treated according to the present invention is monitored regularly during the course of the treatment and after remission. A number of physiological, sympathetic, parasympathetic, motor, autonomic and psychological parameters are assessed in order to evaluate the efficacy of the technique in reversing the symptoms of SCI and these are described in detail below.

An examination of the referring clinician's records, including symptom description, site of lesion categorization, symptom progression, clinical intervention, treatments and general history of the injury is made. Based on this examination and a thorough examination of the patient, including a Magnetic Resonance Imaging (MRI), Electromyography (EMG), Nerve Conduction Velocity (NCV) scan and other neurological examinations and investigations including a neurological examination to assess the extent of the damage and to obtain a record of the lesion prior to treatment, methodologies for the semi-quantitative description of improvement after transplantation according to the practices of the present invention are made and are described in detail below.

Sympathetic parameters and neurological well being including the mental state of the patient, whether depressed or otherwise, behavioral characteristics, cranial nerve function and general demeanor as part of a psychological evaluation are noted.

An evaluation of signs and symptoms linked to the neurological damage at the site of the lesion and functioning of the autonomic nervous system is made. This includes a neurological examination, testing the ability to sense deep pressure, sense of touch, sensation, balance, ability to sense pain, ability to sense change in temperature, involuntary movements, presence of cold sweats, giddiness, blood pressure, breathing difficulty, abnormal posture whilst lying down and ability to sit unaided.

An evaluation of bladder and bowel function is made. This includes bladder control, bladder stream and sensation of fullness in the bladder, bowel control, time for evacuation of the bowel and sensation in the bowel.

An evaluation of the motor function of the upper body is made in order to assess the extent of damage to the central nervous system. This includes shoulder movement, wrist and finger movement, tendon reflexes, and strength of limb movement, muscular atrophy and hand grasp.

An evaluation of the motor function of the lower body is made in order to assess the extent of damage to the central nervous system. This includes hip movement, knee movement, toe movement, tendon reflexes, and strength of the limb, muscular atrophy and plantar response. A detailed neurological examination is also conducted at regular intervals during the treatment in order to monitor the progress of limb innervation.

To aid recovery of the patient during the course of clinic visits, standard physical therapy techniques are used in order to tone the patient as motor function returns, so that they may recover use of their limbs and joints and become more mobile.

Proof of neural regeneration is demonstrated by restoration of neurological function and neurological evaluation. Examples for the treatment protocol for SCI have been provided as case studies in the present application.

Treatment of Developmental Disorders of the Nervous System hES cells and/or their derivatives according to the practice of the present invention are administered in an amount of about 750,000 to about 160 million cells for the treatment of developmental disorders such as Autism and Mental Retardation. In another embodiment, about 750,000 to about 80 million cells are administered via intramuscular or intravenous routes after a test dose. The intrathecal route can also be used. In a further embodiment, intracranial transplantation can also be used. The hES cells and/or their derivatives are predominantly neuronal progenitor cells. In another embodiment, hematopoietic and neuronal progenitor cells are administered via intramuscular or intravenous routes. This treatment continues over a period of a year beginning with daily injections via intramuscular or intravenous routes for a period of 3 months. Then the same injections continue once a week for the next 3-6 months and then once a fortnight for the next 3 months and then once a month according to the physician's observations. The intrathecal injection is included in the protocol only 6-8 months after the start of the treatment and then also only if the patient is showing no response to the intramuscular and intravenous injections. In another embodiment of the present invention, 750,000 to 80 million hES cells and/or their derivatives are resuspended in 100 ml of normal saline and administered via intravenous infusion

EXAMPLE 1

A patient diagnosed with Autism with flapping tremors, hyperactive state, no social skills, no eye contact, pin rolling movements, inability to follow instructions, not willing to learn, showed improvement after the administration of a pharmaceutical composition comprising hES cells and their derivatives including neuronal stem cell progenitors and hematopoietic stem cell progenitors.

The schedule of injections for this patient is shown in Table 2. For this table and all of the ensuing tables regarding injection schedules, the cell type indicator "neuronal" refers to a cell population of hES cells that have been partially differentiated in a medium (e.g., DMEM) that promotes differentiation to neural progenitor stem cells. The cell population comprises hES cells and stem cells that are predominantly neuronal progenitor stem cells. The indicator "non-neuronal" refers to a cell population of hES cells that have been partially differentiated in a medium (e.g., RPMI) that promotes differentiation to progenitor stem cells other than neuronal progenitor stem cells. The cell population comprises hES cells and various stem cells that are predominantly not neuronal progenitor stem cells.

TABLE 2

| Date | Route of administration | Cell types |
|---|---|---|
| 3/13 | test dose | non-neuronal |
| 3/14 | im | neuronal |
| 3/16 | im | neuronal |
| 3/17 | im | neuronal |

TABLE 2-continued

| Date | Route of administration | Cell types |
|---|---|---|
| 3/18 | im | neuronal |
| 3/20 | im | neuronal |
| 3/21 | im | neuronal |
| 3/22 | im | neuronal |
| 3/23 | im | non-neuronal |
| 3/24 | im | neuronal |
| 3/27 | im | neuronal |
| 3/28 | im | non-neuronal |
| 3/29 | im | non-neuronal |
| 3/30 | im | non-neuronal |
| 3/31 | im | neuronal |
| 4/3 | im | neuronal |
| 4/4 | im | neuronal |
| 4/5 | im | neuronal |
| 4/6 | im | neuronal |
| 4/7 | im | neuronal |
| 4/11 | im | neuronal |
| 4/12 | im | neuronal |
| 4/13 | im | neuronal |
| 4/14 | im | neuronal |
| 4/17 | iv | neuronal |
| 4/19 | im | neuronal |
| 4/21 | iv | neuronal |
| 4/24 | im | neuronal |
| 4/25 | im | neuronal |
| 4/28 | iv | neuronal |
| 5/1 | iv | neuronal |
| 5/3 | iv | neuronal |
| 5/5 | im | neuronal |
| 5/8 | iv | neuronal |
| 5/10 | im | neuronal |
| 5/12 | im | neuronal |
| 5/15 | iv | neuronal |
| 5/17 | im | neuronal |
| 5/29 | im | neuronal |
| 5/31 | iv | neuronal |
| 6/2 | iv | non-neuronal |
| 6/5 | im | neuronal |
| 6/7 | iv | neuronal |
| 6/9 | iv | non-neuronal |
| 6/12 | iv | neuronal |
| 6/14 | iv infusion | neuronal |
| 6/16 | im | neuronal |
| 6/19 | im | non-neuronal |
| 6/21 | im | neuronal |
| 6/23 | iv | neuronal |
| 7/3 | iv | neuronal |
| 7/5 | iv infusion | neuronal |
| 7/7 | im | non-neuronal |
| 7/10 | im | non-neuronal |
| 7/12 | im | neuronal |
| 7/14 | im | neuronal |
| 7/17 | iv infusion × 2 | neuronal |
| 7/18 | im | non-neuronal |
| 7/20 | im | non-neuronal |
| 7/24 | im | non-neuronal |
| 7/28 | im | non-neuronal |
| 7/31 | im | non-neuronal |
| 8/2 | im | non-neuronal |
| 8/4 | im | non-neuronal |
| 8/7 | im | non-neuronal |
| 8/10 | im | non-neuronal |
| 8/11 | im | non-neuronal |
| 8/14 | im | non-neuronal |
| 8/18 | im | non-neuronal |
| 8/21 | im | neuronal |
| 8/23 | im | non-neuronal |
| 8/28 | im | non-neuronal |
| 8/30 | im | non-neuronal |
| 9/1 | im | non-neuronal |
| 9/4 | im | non-neuronal |

Treatment of Degenerative Nervous System Disorders hES cells and/or their derivatives, wherein said cells comprise neuronal stem cell progenitors and hematopoietic stem cell progenitors according to the practice of the present invention, are administered in an amount of about 750,000 to about 160 million cells for the treatment of Degenerative Nervous System Disorders including but not limited to Cortico-Basal Degeneration, Olivo Ponto Cerebellar Atrophy, Alzheimer's Disease, Parkinson's Disease, Multiple Sclerosis, Dementia, Auditory Nerve Atrophy and Motor Neuron Disease. In another embodiment, about 750,000 to about 80 million cells are administered.

While administration protocols may be varied to suit the particular patient, a typical protocol for the treatment of degenerative nervous system disorders in children comprises daily intramuscular and intravenous injections in the first month, injections three times a week during months 2-4, weekly injections in months 5 and 6 and weekly booster shots in months 9-12. For adults, a typical protocol involves daily intramuscular and intravenous injections along with administration by epidural catheter, lumbar puncture, intrathecal, or caudal routes. This is followed by two intravenous infusions with a minimum gap of at least 7 days. Finally, booster injections are administered once a month for 6 months and then once every 2 months for at least 6 months. Treatment may be continued for longer periods and may even be life long as the diseases are progressive.

In the case of progressive and degenerative disorders, stemming or stabilizing the disease progression through rapid intervention according to the practice of the present invention permits an increased self dependence of the patient. It is only after the stabilizing effect that some improvements can be seen.

EXAMPLE 2

A patient suffered from a two-year history of repetitive progressive multiple sclerosis taking SOLUMEDROL (methylprednisolone) daily was unable to walk, had no bladder or bowel control, and suffered frequently from respiratory disorders.

Pursuant to the treatment according to the present invention, the subject's condition improved, the patient was able to walk and there was a restoration of bladder and bowel control and the use of SOLUMEDROL was reduced. The MRI has shown a 50% improvement.

The schedule of injections for this patient is shown in Table 3.

TABLE 3

| Date | Route of administration | Cell types |
|---|---|---|
| 7/15 | test dose | neuronal |
| 7/25 | im | neuronal |
| 7/26 | im | neuronal |
| 7/27 | im | non-neuronal |
| 7/28 | im | neuronal |
| 7/29 | im | neuronal |
| 8/1 | im | neuronal |
| 8/2 | im | neuronal |
| 8/3 | im | neuronal |
| 8/4 | im × 2 | neuronal |
| 8/5 | im × 2 | neuronal |
| 8/9 | im × 2 | neuronal |
| 8/10 | im × 2 | neuronal |
| 8/11 | im | neuronal |
| 8/12 | im × 2 | neuronal |
| 8/16 | iv im | neuronal |
| 8/22 | im × 4 | hES |
| 8/24 | iv im | neuronal |
| 9/2 | iv | neuronal |
| 9/8 | im | neuronal |
| 9/15 | im | neuronal and non-neuronal mixture |

TABLE 3-continued

| Date | Route of administration | Cell types |
|------|------------------------|------------|
| 9/19 | iv | neuronal |
| 9/22 | im | neuronal |
| 9/26 | im | neuronal and non-neuronal mixture |
| 9/29 | im | neuronal and non-neuronal mixture |
| 10/3 | im | neuronal and non-neuronal mixture |
| 10/6 | im | non-neuronal |
| 10/13 | iv | neuronal and non-neuronal mixture |
| 10/17 | im | neuronal and non-neuronal mixture |
| 10/20 | iv | neuronal |
| 10/24 | iv | neuronal and non-neuronal mixture |
| 10/31 | iv | neuronal and non-neuronal mixture |
| 11/3 | iv | neuronal and non-neuronal mixture |
|  | im |  |
| 11/7 | im | non-neuronal |
| 11/21 | iv | non-neuronal |
| 11/24 | im | non-neuronal |
| 1/19 | im × 2 | non-neuronal |
|  |  | neuronal |
| 1/25 | im × 2 | neuronal |
| 2/2 | im | non-neuronal |
|  | iv | neuronal |
| 2/15 | im × 2 | neuronal |
|  | iv | non-neuronal |
| 2/23 | im × 2 | neuronal |
|  | iv | non-neuronal |
| 3/2 | im × 2 | neuronal |
|  | iv | non-neuronal |
| 3/8 | im × 2 | non-neuronal |
|  | iv |  |
| 3/16 | im × 2 | neuronal |
|  | iv | non-neuronal |
| 5/2 | im × 2 | non-neuronal |
| 5/12 | im × 2 | neuronal |
|  | iv | non-neuronal |
| 6/8 | im × 2 | neuronal |
|  | iv | non-neuronal |
| 6/16 | im × 2 | neuronal |
|  | iv | non-neuronal |
| 7/3 | im | neuronal |
| 7/4 | im | neuronal |
| 7/5 | im | neuronal |
| 7/6 | im | neuronal |
| 7/7 | im | neuronal |
| 7/18 | im × 2 | neuronal |
|  | iv | non-neuronal |
| 7/22 | im × 2 | neuronal |
|  | iv | non-neuronal |
| 7/24 | im × 2 | neuronal |
|  | iv | non-neuronal |
| 8/1 | im × 2 | non-neuronal |
|  | iv |  |
| 8/4 | im × 2 | non-neuronal |
|  | iv |  |
| 8/7 | im × 2 | non-neuronal |
|  | iv |  |
| 8/24 | im × 2 | non-neuronal |
|  | iv |  |
| 8/28 | im × 2 | non-neuronal |
|  | iv |  |
| 9/2 | im × 2 | non-neuronal |
|  | iv |  |
| 9/6 | im × 2 | non-neuronal |
|  | iv |  |
| 9/9 | im × 2 | non-neuronal |
|  | iv |  |

EXAMPLE 3

A 60 year old man presented with ALS (motor neuron disease) two years ago with fast deterioration in his arms and hands. There was continuous twitching and fasciculations in his arms, hands and tongue. He could not supinate and pronate his left arm, or lift it above his head. His right arm could be lifted up with a jerk and he had skeletal hands. 1½ years after treatment, his hands have recovered from the skeletal frame with regeneration of hypothenar and thenar muscles of both hands. Supination and pronation is possible with both arms. He found the same difficulty in swallowing, which has not worsened since. There is no deterioration with his legs, breathing and speech.

The schedule of injections for this patient is shown in Table 4.

TABLE 4

| Date | Route of administration | Cell types |
|------|------------------------|------------|
| 8/2 | im | neuronal (test dose) |
| 8/4 | im | neuronal |
|  |  | non neuronal |
| 8/5 | im | neuronal |
| 8/8 | im | neuronal |
| 8/9 | im | neuronal |
| 8/10 | im | neuronal |
| 8/11 | im | neuronal |
| 8/12 | im | neuronal |
| 8/16 | im | neuronal |
| 8/17 | im | hES |
| 8/22 | im | neuronal |
| 8/23 | im | neuronal |
| 8/24 | im × 3 | non-neuronal |
| 8/25 | im × 3 | non-neuronal |
| 8/26 | im | neuronal |
| 8/29 | im | neuronal |
| 8/31 | im | neuronal |
|  | iv |  |
| 9/2 | im | neuronal |
| 9/5 | im | neuronal |
|  | iv |  |
| 9/7 | im | neuronal |
| 9/9 | im | neuronal |
|  | iv | mixed |
| 9/12 | im | neuronal |
|  | iv | non neuronal |
| 9/13 | im | neuronal |
|  | iv | non neuronal |
| 9/16 | im | mixed |
| 9/19 | im | neuronal |
|  | iv | mixed |
| 9/22 | iv | neuronal |
| 9/23 | im | neuronal |
|  | iv | non neuronal |
| 9/26 | im | mixed |
| 9/27 | im | mixed |
| 9/28 | im | neuronal |
|  | iv | non neuronal |
| 9/30 | im | mixed |
|  | iv | non neuronal |
| 10/3 | iv | mixed |
| 10/7 | im | non neuronal |
| 10/10 | iv | neuronal |
| 10/12 | iv | mixed |
| 10/17 | im | neuronal |
|  | iv | mixed |
| 10/20 | epidural | neuronal |
| 10/21 | iv | neuronal |
| 10/24 | iv | mixed |
| 10/27 | iv | neuronal |
| 10/28 | iv | mixed |
| 10/31 | iv | mixed |
| 11/2 | iv | mixed |
| 11/3 | epidural | neuronal |
| 11/4 | iv | mixed |
| 11/7 | im | non neuronal |
| 11/9 | im | non neuronal |
| 11/11 | im | neuronal |
| 11/14 | im | neuronal |
| 11/17 | im | non neuronal |
| 11/21 | im | non neuronal |
| 11/23 | im | non neuronal |
| 12/13 | im | non neuronal |
| 12/19 | im | neuronal |
| 12/21 | im | neuronal |
| 12/23 | im | neuronal |

TABLE 4-continued

| Date | Route of administration | Cell types |
|---|---|---|
| 12/29 | im | neuronal |
| 1/3 | im | neuronal |
| 1/9 | im | neuronal |
| 1/12 | im | neuronal |
| 1/13 | iv | non neuronal |
| 1/16 | iv | neuronal |
| 1/19 | im | neuronal |
|  | iv | non neuronal |
| 1/23 | epidural | neuronal |
| 1/27 | im | neuronal |
|  | iv | non neuronal |
| 1/29 | im | neuronal |
|  | iv | non neuronal |
| 2/1 | iv | neuronal |
| 2/3 | im | neuronal |
|  | iv | non neuronal |
| 2/6 | im | neuronal |
|  | iv | non neuronal |
| 2/8 | iv | non neuronal |
| 2/10 | iv | non neuronal |
| 2/13 | iv | non neuronal |
| 2/15 | iv | non neuronal |
| 2/17 | im | neuronal |
|  | iv | non neuronal |
| 2/20 | im | neuronal |
|  | iv | non neuronal |
| 2/22 | im | neuronal |
|  | iv | non neuronal |
| 2/24 | im | neuronal |
|  | iv | non neuronal |
| 2/27 | iv | neuronal |
|  | oral spray | non neuronal |
| 3/1 | im | neuronal |
|  | iv | non neuronal |
| 3/6 | iv | non neuronal |
| 3/8 | epidural | neuronal |
| 3/9 | epidural | neuronal |
| 3/10 | epidural | neuronal |
| 3/11 | iv | neuronal |
| 3/22 | im | non neuronal |
| 3/24 | im | non neuronal |
| 3/27 | iv | non neuronal |
| 3/29 | im | non neuronal |
|  | iv |  |
| 3/31 | im | neuronal |
|  | oral spray | non neuronal |
| 4/3 | im | neuronal |
|  | iv | non neuronal |
| 4/5 | im | neuronal |
|  | iv | non neuronal |
| 4/7 | im | neuronal |
|  | iv | non neuronal |
| 4/10 | im | neuronal |
|  | iv | non neuronal |
| 4/12 | im | neuronal |
|  | iv | non neuronal |
| 4/19 | epidural | neuronal |
| 4/24 | iv | neuronal |
| 4/26 | iv | non neuronal |
| 4/28 | im | neuronal |
|  | iv | non neuronal |
| 5/2 | im | non neuronal |
| 5/3 | im | neuronal |
| 5/5 | im | neuronal |
|  | iv | non neuronal |
| 5/8 | iv | non neuronal |
| 5/11 | intravenous infusion | neuronal |
| 5/12 | im | non neuronal |
| 5/14 | im | neuronal |
|  | iv | non neuronal |
| 5/15 | im | neuronal |
|  | iv | non neuronal |
| 5/16 | im | neuronal |
|  | iv | non neuronal |
| 5/17 | im | neuronal |
|  | iv | non neuronal |
| 5/19 | im | neuronal |
|  | iv | non neuronal |
| 5/22 | im | neuronal |
|  | iv | non neuronal |
| 5/24 | im | neuronal |
|  | iv | non neuronal |
| 5/26 | im | neuronal |
|  | iv | non neuronal |
| 5/29 | im | neuronal |
|  | iv | non neuronal |
| 6/1 | im | neuronal |
|  | iv | non neuronal |
| 6/2 | im | neuronal |
|  | iv | non neuronal |
| 6/5 | epidural catheter | neuronal |
| 6/6 | epidural catheter | neuronal |
| 6/7 | epidural catheter | neuronal |
| 6/12 | im | neuronal |
|  |  | non neuronal |
| 6/14 | im | neuronal |
|  | iv | non neuronal |
| 6/16 | intravenous infusion | neuronal |
| 6/21 | im | neuronal |
| 6/24 | im | neuronal |
| 7/3 | iv | neuronal |
| 7/5 | iv | neuronal |
| 7/7 | iv | neuronal |
| 7/10 | iv | neuronal |
| 7/12 | iv | neuronal |
| 7/14 | iv | neuronal |
| 7/17 | iv | non neuronal |
| 7/20 | iv | non neuronal |
| 7/24 | iv | non neuronal |
| 7/25 | epidural (intrathecal) | non neuronal |
| 7/31 | iv | neuronal |
| 8/2 | iv | neuronal |
| 8/3 | iv | non neuronal |
| 8/8 | iv | non neuronal |
| 8/11 | iv | non neuronal |
| 8/16 | iv | neuronal |
| 8/23 | iv | neuronal |
| 8/28 | iv | non neuronal |
| 8/29 | iv | non neuronal |
| 9/5 | iv | non neuronal |
| 9/6 | iv | non neuronal |
| 9/8 | iv | non neuronal |
| 9/13 | iv | non neuronal |
| 9/15 | im | non neuronal |
|  | iv |  |
| 9/18 | im | non neuronal |
|  | iv |  |
| 9/19 | intravenous infusion | neuronal |
| 9/20 | intravenous infusion | non neuronal |
| 9/22 | im | non neuronal |
|  | iv |  |
| 9/25 | im | non neuronal |
|  | iv |  |
| 9/27 | im | non neuronal |
|  | iv |  |
| 9/29 | im | non neuronal |
|  | iv |  |
| 10/2 | im | non neuronal |
|  | iv |  |
| 10/4 | im | non neuronal |
|  | iv |  |
| 10/9 | im | non neuronal |
|  | iv |  |
| 10/13 | im | non neuronal |
|  | iv |  |
| 10/16 | im | non neuronal |
|  | iv |  |
| 10/18 | im | non neuronal |
|  | iv |  |
| 10/20 | im | non neuronal |
|  | iv |  |
| 10/23 | im | non neuronal |
|  | iv |  |
| 10/25 | iv infusion | mixed |
| 10/27 | iv infusion | non neuronal |
| 11/1 | im | non neuronal |

TABLE 4-continued

| Date | Route of administration | Cell types |
|---|---|---|
| | iv | |
| 11/6 | im | non neuronal |
| | iv | |
| 11/8 | im | non neuronal |
| | iv | |
| 11/10 | intrathecal | neuronal |
| 11/13 | im | non neuronal |
| | iv | |
| 11/15 | im | non neuronal |
| | iv | |
| 11/17 | im | neuronal |
| | iv | non neuronal |
| 11/20 | im | non neuronal |
| | iv | |
| 11/22 | im | non neuronal |
| | iv | |
| 11/24 | iv | neuronal |
| 11/27 | im | mixed |
| | iv | |
| 12/1 | im | mixed |
| | iv | |
| 12/4 | iv infusion | mixed |
| 12/6 | im | non neuronal |
| | iv | |
| 12/8 | iv | neuronal |
| 12/11 | im | non neuronal |
| | iv | |
| 12/14 | iv infusion | non neuronal |
| 12/15 | iv infusion | non neuronal |
| 12/18 | im | non neuronal |
| | iv | |
| 12/20 | iv | neuronal |
| 12/27 | im | neuronal |
| | iv | |
| 12/29 | im | neuronal |
| | iv | |
| 1/4 | im | non neuronal |
| | iv | |
| 1/8 | iv infusion | mixed |
| 1/9 | iv infusion | mixed |
| 1/10 | iv infusion | mixed |
| 1/12 | im | non neuronal |
| | iv | |
| 1/16 | im | non neuronal |
| | iv | |
| 1/19 | im | non neuronal |
| | iv | |
| 1/22 | im | mixed |
| | iv | |

EXAMPLE 4

Patient was diagnosed to be suffering from Parkinson's disease. Patient did not respond to the standard treatment and his condition became worse as time progressed. He had a typical shuffling gait. Unilateral tremors were present in the right arm and he was physiologically very much depressed. He couldn't open his eyes. Since treatment began, the patient has shown improvement gradually and after one year of hES cell treatment the patient is markedly improved. The gait is normal, the tremors in the hand are minimal and psychologically he is upbeat. He opens his eyes fully. He can sign and write now, which was impossible at the start of the treatment. He is less dependent on others now.

The schedule of injections for this patient is shown in Table 5.

TABLE 5

| Date | Route of administration | Cell types |
|---|---|---|
| 1/30 | im | neuronal (test dose) |
| | iv | |
| 1/31 | im | neuronal |
| 2/1 | iv | neuronal |
| 2/2 | iv | non neuronal |
| | im | neuronal |
| 2/3 | iv | neuronal |
| | im | |
| 2/4 | iv | neuronal |
| | im | |
| 2/5 | iv | neuronal |
| | im | |
| 2/6 | iv | non neuronal |
| | im | neuronal |
| 2/8 | iv | non neuronal |
| | im | neuronal |
| 2/9 | iv | non neuronal |
| | im | neuronal |
| 2/10 | iv | non neuronal |
| | im | neuronal |
| 2/11 | iv | non neuronal |
| | im | |
| 2/12 | iv | neuronal |
| | im | non neuronal |
| 2/13 | iv | neuronal |
| | im | non neuronal |
| 2/14 | iv | neuronal |
| 2/15 | iv | neuronal |
| | im | non neuronal |
| 2/16 | iv | neuronal |
| | im | non neuronal |
| 2/17 | iv | neuronal |
| | im | non neuronal |
| 2/18 | iv | neuronal |
| | im | non neuronal |
| 2/19 | iv | neuronal |
| | im | non neuronal |
| 2/20 | iv | neuronal |
| | im | non neuronal |
| 2/21 | iv | neuronal |
| | im | non neuronal |
| 2/23 | iv | neuronal |
| | im | non neuronal |
| 2/25 | iv | neuronal |
| | im | non neuronal |
| 2/26 | iv | neuronal |
| | im | non neuronal |
| 2/27 | iv | neuronal |
| | im | non neuronal |
| 2/28 | iv | neuronal |
| 3/1 | iv | neuronal |
| | im | non neuronal |
| 3/2 | iv | neuronal |
| | im | non neuronal |
| 3/3 | iv | neuronal |
| 3/4 | im | neuronal |
| 3/5 | iv | neuronal |
| 3/7 | im | neuronal |
| 3/9 | iv | non neuronal |
| 3/10 | iv | neuronal |
| | im | non neuronal |
| 3/11 | iv | neuronal |
| | im | non neuronal |
| 3/12 | iv | neuronal |
| | im | non neuronal |
| 3/13 | iv | neuronal |
| | im | non neuronal |
| 3/28 | iv | neuronal |
| 3/29 | iv im | neuronal |
| | iv im | non neuronal |
| 3/30 | iv im | neuronal |
| | im | non neuronal |
| 3/31 | iv | neuronal |
| | im | non neuronal |

TABLE 5-continued

| Date | Route of administration | Cell types |
|---|---|---|
| 4/1 | iv | neuronal |
|  | im | non neuronal |
| 4/2 | iv | neuronal |
|  | im | non neuronal |
| 4/3 | iv | neuronal |
|  | im | non neuronal |
| 4/4 | iv im | neuronal |
|  | im | non neuronal |
| 4/5 | iv | neuronal |
|  | im | non neuronal |
| 4/6 | iv | neuronal |
|  | im | non neuronal |
| 4/7 | iv im | neuronal |
|  | im | non neuronal |
| 4/8 | iv | neuronal |
|  | im | non neuronal |
| 4/9 | iv | neuronal |
|  | im | non neuronal |
| 4/10 | iv | neuronal |
|  | im | non neuronal |
| 4/11 | iv | neuronal |
|  | im | non neuronal |
| 4/12 | iv | neuronal |
|  | im | non neuronal |
| 4/13 | iv | neuronal |
|  | im | non neuronal |
| 4/14 | iv | neuronal |
|  | im | non neuronal |
| 4/15 | iv | neuronal |
|  | im | non neuronal |
| 4/16 | iv | neuronal |
|  | im | non neuronal |
| 5/20 | iv | neuronal |
|  | im | non neuronal |
| 5/21 | infusion | non neuronal |
| 7/10 | iv | neuronal |
|  | im | non neuronal |
| 7/11 | iv | neuronal |
|  | im | non neuronal |
| 7/12 | iv | neuronal |
|  | im | non neuronal |
| 7/13 | iv | neuronal |
|  | im | non neuronal |
| 7/14 | iv | neuronal |
|  | im | non neuronal |
| 7/15 | iv infusion | non neuronal |
| 7/16 | iv infusion | non neuronal |
| 7/17 | iv | neuronal |
|  | im | non neuronal |
| 7/18 | iv | neuronal |
|  | im | non neuronal |
| 7/19 | iv | neuronal |
|  | im | non neuronal |
| 7/20 | iv | neuronal |
|  | im | non neuronal |
| 7/21 | iv | neuronal |
|  | im | non neuronal |
| 7/22 | iv infusion | neuronal |
| 7/23 | iv infusion | neuronal |
| 7/24 | iv infusion | non neuronal |
| 7/25 | iv | neuronal |
|  | im | non neuronal |
| 7/26 | iv | neuronal |
|  | im | non neuronal |
| 7/27 | iv | neuronal |
|  | im | non neuronal |
| 7/28 | iv | neuronal |
|  | im | non neuronal |
| 7/29 | iv infusion | neuronal |
| 7/30 | im | neuronal |
|  |  | non neuronal |
| 9/9 | im | non neuronal |
|  | iv |  |
| 9/12 | im | non neuronal |
|  | iv |  |
| 9/13 | iv | non neuronal |
|  | im |  |
| 9/14 | im | non neuronal |
|  | iv |  |
| 9/15 | im | non neuronal |
|  | iv |  |
| 9/16 | im | non neuronal |
|  | iv |  |
| 9/17 | iv infusion | neuronal |
| 9/18 | iv infusion | neuronal |
| 9/19 | iv | neuronal |
| 9/20 | im | non neuronal |
|  | iv |  |
| 9/21 | im | non neuronal |
|  | iv |  |
| 9/22 | im | non neuronal |
|  | iv |  |
| 9/23 | iv infusion | non neuronal |
| 9/24 | iv infusion | non neuronal |
| 9/25 | iv | non neuronal |
|  | im |  |
| 9/26 | iv | non neuronal |
|  | im |  |
| 9/27 | iv | non neuronal |
|  | im |  |
| 9/28 | iv | non neuronal |
|  | im |  |
| 9/29 | iv | neuronal |
|  | iv infusion |  |
| 9/30 | iv | non neuronal |
|  | im |  |
| 11/9 | iv | non neuronal |
|  | im |  |
| 11/10 | iv | non neuronal |
|  | im |  |
| 11/11 | iv | non neuronal |
|  | im |  |
| 11/12 | iv | non neuronal |
|  | im |  |
| 11/14 | iv infusion | mixed |
| 11/16 | iv | non neuronal |
|  | im |  |
| 11/17 | iv | non neuronal |
|  | im |  |
| 11/18 | iv infusion | neuronal |
| 11/19 | iv infusion | neuronal |
| 11/20 | iv | non neuronal |
|  | im |  |
| 11/21 | iv | non neuronal |
|  | im |  |
| 11/22 | iv | non neuronal |
|  | im |  |
| 11/23 | iv | non neuronal |
|  | im |  |
| 11/24 | iv infusion | neuronal |
| 11/25 | iv infusion | neuronal |
| 11/26 | im | mixed |
|  | iv |  |
| 11/29 | iv | non neuronal |
|  | im |  |
| 1/9 | iv | non neuronal |
|  | im |  |
| 1/10 | iv | non neuronal |
|  | im |  |
| 1/11 | iv | non neuronal |
|  | im |  |
| 1/12 | iv | non neuronal |
|  | im |  |
| 1/13 | iv infusion | mixed |
| 1/14 | iv infusion | mixed |
| 1/15 | iv | non neuronal |
|  | im |  |
| 1/16 | iv | non neuronal |
|  | im |  |
| 1/17 | iv | non neuronal |
|  | im |  |
| 1/18 | iv | non neuronal |
| 1/19 | iv | non neuronal |
| 1/20 | iv infusion | non neuronal |
| 1/21 | iv infusion | mixed |

TABLE 5-continued

| Date | Route of administration | Cell types |
|---|---|---|
| 1/22 | im | mixed |
|  | iv |  |
| 1/23 | im | mixed |
|  | iv |  |
| 1/24 | iv | neuronal |
|  | im |  |
| 1/25 | iv | neuronal |
|  | im |  |
| 1/26 | iv | neuronal |
|  | im |  |
| 1/27 | iv infusion | mixed |
| 1/28 | iv infusion | mixed |
| 1/29 | iv | neuronal |
|  | im |  |
| 1/30 | iv | neuronal |
|  | im |  |

Treatment of Cerebral Palsy hES cells and/or their derivatives, wherein said cells comprise neuronal stem cell progenitors and hematopoietic stem cell progenitors according to the practice of the present invention, are administered in an amount of about 750,000 to about 160 million cells for the treatment of Cerebral Palsy. The protocol and the dosage are the same as that for the treatment of neurodegenerative disorders.

EXAMPLE 5

A 48 years old male diagnosed at AIIMS as CP at birth had slurred speech, shuffling gait, difficulty in swallowing, and left sided hemiparesis. The charting of muscle tone, reflex, and power was done to confirm the same.

Six months after treatment he has clearer speech, no difficulty in swallowing, is able to use the left side of his body and his gait has improved. He is able to shave with his left hand and also use his left hand to pick up cups, etc. His balancing is better and he is able to go on long walks.

The schedule of injections for this patient is shown in Table 6.

TABLE 6

| Date | Route of administration | Cell types |
|---|---|---|
| 3/8 | test dose | non-neuronal |
| 3/10 | iv | neuronal |
|  | im |  |
| 3/17 | iv | neuronal |
|  | im |  |
| 4/8 | iv | neuronal |
|  | im × 2 |  |
| 4/9 | iv × 3 | neuronal |
|  | im × 3 | non-neuronal |
| 4/10 | iv × 3 | neuronal |
|  | im × 3 | non-neuronal |
| 5/10 | iv | neuronal |
|  | im | non-neuronal |
| 5/11 | im × 2 | neuronal |
|  | iv |  |
| 5/12 | iv infusion × 2 | neuronal |
| 5/13 | iv infusion | non-neuronal |
| 5/14 | iv infusion | neuronal |
|  | iv | non-neuronal |
|  | im |  |
| 5/15 | iv infusion | non-neuronal |
| 7/19 | iv | neuronal |
|  | im | non-neuronal |
| 7/20 | iv infusion | non-neuronal |
| 7/21 | iv infusion × 2 | non-neuronal |
| 7/22 | iv | neuronal |
|  | im | non-neuronal |

TABLE 6-continued

| Date | Route of administration | Cell types |
|---|---|---|
| 7/24 | iv | neuronal |
|  | im | non-neuronal |
| 7/25 | deep spinal | neuronal |
| 7/26 | iv | neuronal |
|  | im | non-neuronal |
| 7/27 | iv | neuronal |
|  | im | non-neuronal |
| 7/28 | iv | non-neuronal |
|  | im |  |
| 7/31 | iv | neuronal |
|  | im | non-neuronal |
| 8/1 | iv | non-neuronal |
|  | im |  |
| 8/2 | iv | non-neuronal |
|  | im |  |
| 8/3 | iv | non-neuronal |
|  | im |  |
| 8/4 | iv infusion × 2 | non-neuronal |
| 8/5 | iv infusion | non-neuronal |
| 8/7 | iv | non-neuronal |
|  | im |  |
| 8/8 | iv | non-neuronal |
|  | im |  |
| 8/9 | iv | non-neuronal |
|  | im |  |
| 8/10 | iv | non-neuronal |
|  | im |  |
| 8/11 | iv | non-neuronal |
|  | im |  |
| 8/12 | iv | non-neuronal |
|  | im |  |
| 8/14 | deep spinal | neuronal |
| 8/16 | iv infusion | neuronal |
| 8/17 | iv infusion | neuronal |
| 8/18 | iv | neuronal |
|  | im |  |
| 8/19 | deep spinal | neuronal |
| 8/20 | iv | non-neuronal |
|  | im |  |
| 8/21 | iv | non-neuronal |
|  | im |  |
| 8/22 | iv | non-neuronal |
|  | im |  |
| 8/24 | iv infusion | non-neuronal |
| 8/25 | iv infusion | non-neuronal |
| 8/26 | iv | non-neuronal |
|  | im |  |

EXAMPLE 6

A 3 year old baby girl was brought into the clinic with CP and looked and behaved like a month old baby with no neck control, weak cry, no response and inability to suck through the bottle. She was absolutely floppy.

After a year and a half of treatment she has grown and looks like a 2 year old baby. She has neck control, recognizes her parents, crawls on the bed, eats normal food, smiles on recognition, and sits with support, and has taken a few steps with her mother holding her. Her gait is a scissor gait and she has also started calling out to her parents.

The schedule of injections for this patient is shown in Table 7.

TABLE 7

| Date | Route of administration | Cell types |
|---|---|---|
| 8/4 | im | neuronal (test dose) |
| 8/5 | im | neuronal |
| 8/8 | im | neuronal |
| 8/9 | im | neuronal |
| 8/10 | im | neuronal |

TABLE 7-continued

| Date | Route of administration | Cell types |
|---|---|---|
| 8/11 | im | neuronal |
| 8/12 | im | neuronal |
| 8/16 | im | neuronal |
| 8/17 | im | neuronal |
| 8/18 | im | neuronal |
| 8/19 | im | non neuronal |
| 8/22 | im | mixed |
| 8/23 | im | mixed |
| 8/25 | im | mixed |
| 8/26 | im | neuronal |
| 8/29 | im | neuronal |
| 8/30 | im | neuronal |
| 8/31 | im | neuronal |
| 9/1 | im | neuronal |
| 9/2 | im | neuronal |
| 9/5 | im | non neuronal |
| 9/6 | im | neuronal |
| 9/7 | im | neuronal |
| 9/8 | im | neuronal |
| 9/12 | im | mixed |
| 9/14 | im | non neuronal |
| 9/16 | im | mixed |
| 9/19 | im | neuronal |
| 9/23 | im | neuronal |
| 9/26 | im | mixed |
| 9/28 | im | mixed |
| 9/30 | im | mixed |
| 10/3 | im | mixed |
| 10/5 | im | neuronal |
| 10/10 | im | non neuronal |
| 10/17 | im | mixed |
| 10/19 | im | non neuronal |
| 10/21 | im | neuronal |
| 10/24 | im | mixed |
| 10/28 | im | mixed |
| 10/31 | im | mixed |
| 11/4 | im | mixed |
| 11/7 | im | non neuronal |
| 11/9 | im | non neuronal |
| 11/11 | im | neuronal |
| 11/14 | im | neuronal |
| 11/15 | im | non neuronal |
| 11/16 | im | non neuronal |
| 11/18 | im | non neuronal |
| 11/22 | im | non neuronal |
| 11/23 | im | non neuronal |
| 11/25 | m | non neuronal |
| 11/28 | im | mixed |
| 11/29 | im | mixed |
| 12/2 | im | mixed |
| 12/7 | im | non neuronal |
| 12/9 | m | non neuronal |
| 12/12 | im | non neuronal |
| 12/14 | m | neuronal |
| 12/16 | im | neuronal |
| 12/19 | im | non neuronal |
| 12/21 | m | neuronal |
| 12/23 | im | neuronal |
| 12/26 | m | non neuronal |
| 12/30 | im | neuronal |
| 1/5 | im | neuronal |
| 1/11 | im | neuronal |
| 1/13 | im | neuronal |
| 1/16 | im | neuronal |
| 1/18 | im | neuronal |
| 1/23 | im | neuronal |
| 1/25 | im | neuronal |
| 1/27 | m | neuronal |
| 1/30 | im | neuronal |
| 2/1 | im | neuronal |
| 2/3 | im | neuronal |
| 2/6 | im | neuronal |
| 2/8 | im | neuronal |
| 2/10 | im | neuronal |
| 2/13 | im | neuronal |
| 2/15 | im | neuronal |
| 2/17 | im | non neuronal |
| 22 Feb. 2006 | im | neuronal |
| 2/24 | im | neuronal |
| 2/27 | im | neuronal |
| 3/1 | m | neuronal |
| 3/3 | im | neuronal |
| 3/6 | im | non neuronal |
| 3/8 | im | non neuronal |
| 3/22 | im | non neuronal |
| 3/24 | im | neuronal |
| 3/27 | im | non neuronal |
| 3/29 | im | neuronal |
| 3/31 | im | neuronal |
| 4/7 | im | neuronal |
| 4/10 | im | neuronal |
| 4/12 | im | neuronal |
| 4/14 | im | neuronal |
| 4/17 | im | neuronal |
| 4/19 | im | neuronal |
| 4/21 | im | neuronal |
| 4/24 | im | neuronal |
| 4/26 | im | neuronal |
| 5/1 | im | neuronal |
| 5/8 | im | non neuronal |
| 5/18 | im | neuronal |
| 5/22 | im | neuronal |
| 5/26 | im | neuronal |
| 5/29 | im | neuronal |
| 5/31 | im | neuronal |
| 6/2 | im | neuronal |
| 6/5 | im | neuronal |
| 6/12 | im | neuronal |
| 6/16 | im | neuronal |
| 6/19 | im | neuronal |
| 6/21 | im | neuronal |
| 6/28 | im | neuronal |
| 6/30 | im | neuronal |
| 7/4 | im | neuronal |
| 7/7 | im | neuronal |
| 7/17 | im | neuronal |
| 7/19 | m | neuronal |
| 7/21 | im | neuronal |
| 7/24 | im | neuronal |
| 7/26 | im | neuronal |
| 7/31 | im | non neuronal |
| 8/2 | im | non neuronal |
| 8/4 | im | non neuronal |
| 8/7 | im | non neuronal |
| 8/9 | im | non neuronal |
| 8/11 | im | non neuronal |
| 8/14 | im | non neuronal |
| 8/16 | im | non neuronal |
| 8/18 | im | non neuronal |
| 8/21 | im | non neuronal |
| 8/23 | im | non neuronal |
| 8/25 | im | non neuronal |
| 8/28 | im | non neuronal |
| 8/30 | im | non neuronal |
| 9/1 | im | non neuronal |
| 9/4 | im | non neuronal |
| 9/11 | im | non neuronal |
| 9/13 | im | non neuronal |
| 9/15 | im | non neuronal |
| 9/20 | im | non neuronal |
| 9/25 | im | non neuronal |
| 9/27 | im | non neuronal |
| 10/3 | im | non neuronal |
| 10/4 | im | non neuronal |
| 10/13 | im | non neuronal |
| 10/16 | im | non neuronal |
| 10/18 | im | non neuronal |
| 10/19 | im | non neuronal |
| 10/23 | im | non neuronal |
| 10/25 | im | non neuronal |
| 10/27 | im | non neuronal |
| 10/30 | im | non neuronal |
| 10/31 | im | non neuronal |
| 11/3 | im | non neuronal |
| 11/6 | im | non neuronal |
| 11/8 | im | non neuronal |

TABLE 7-continued

| Date | Route of administration | Cell types |
|---|---|---|
| 11/10 | im | non neuronal |
| 11/13 | im | non neuronal |
| 11/15 | im | non neuronal |
| 11/17 | im | non neuronal |
| 11/20 | im | non neuronal |
| 11/22 | im | non neuronal |
| 11/24 | im | non neuronal |
| 11/27 | im | non neuronal |
| 11/29 | im | non neuronal |
| 12/1 | im | non neuronal |
| 12/8 | im | non neuronal |
| 12/11 | im | non neuronal |
| 12/15 | im | non neuronal |
| 12/26 | im | neuronal |
| 12/27 | im | neuronal |
| 1/3 | im | non neuronal |
| 1/7 | im | non neuronal |
| 1/15 | im | neuronal |
| 1/24 | im | neuronal |
| 1/25 | im | neuronal |
| 1/29 | im | neuronal |

EXAMPLE 8

An 8 year old child was diagnosed with cerebral palsy and with severe mental retardation and was unable to walk on her own. She could not identify objects and had a very low attention span. There was a lot of drooling and she kept her mouth open.

Following treatment, she is not drooling, her attention span has improved and she is looking more alert. She is walking with minimal support.

The schedule of injections for this patient is shown in Table 8.

TABLE 8

| Date | Route of administration | Cell types |
|---|---|---|
| 10/9 | im | non neuronal (test dose) |
| 10/10 | im | non neuronal |
| 10/11 | im | non neuronal × 2 |
| 10/12 | im | non neuronal |
| 10/13 | im | non neuronal |
| 12/5 | im | non neuronal |
| 12/6 | im / iv | non neuronal |
| 12/7 | im × 3 | non neuronal |
| 12/8 | im / iv | non neuronal |
| 12/9 | im / iv | non neuronal |
| 12/10 | im × 3 | non neuronal |
| 12/11 | im / iv | non neuronal |
| 12/12 | im × 3 | non neuronal |
| 12/13 | im / iv | non neuronal |
| 12/14 | im | non neuronal |
| 12/15 | im / iv | non neuronal |
| 12/16 | im × 3 | non neuronal |
| 12/17 | im / iv | non neuronal |
| 12/18 | im | non neuronal |
| 12/19 | im / iv | non neuronal |
| 12/20 | im × 3 | non neuronal |
| 12/21 | im / iv | non neuronal |
| 12/22 | im / iv | non neuronal |

TABLE 8-continued

| Date | Route of administration | Cell types |
|---|---|---|
| 12/23 | im / iv | non neuronal |
| 12/24 | im / iv | non neuronal / neuronal |
| 12/25 | im / iv | neuronal |
| 12/26 | im / iv | neuronal / mixed |
| 12/27 | im × 3 | neuronal |
| 12/28 | im / iv | neuronal |
| 12/29 | im × 3 | neuronal |
| 12/30 | im / iv | neuronal |
| 12/31 | im × 3 | neuronal |
| 1/1 | im / iv | mixed |
| 1/9 | iv infusion | mixed |
| 1/10 | iv infusion | mixed |
| 1/11 | im / iv | non neuronal |
| 1/12 | im / iv | non neuronal |
| 1/13 | im / iv | non neuronal |
| 1/14 | im / iv | non neuronal |
| 1/15 | im × 3 | non neuronal |
| 1/16 | im / iv | non neuronal |
| 1/17 | im × 3 | non neuronal |
| 1/18 | im | non neuronal |
| 1/19 | im | non neuronal |
| 1/20 | im | non neuronal |
| 1/21 | im | mixed |
| 1/22 | im | mixed |
| 1/23 | im | mixed |
| 1/24 | im | neuronal |
| 1/25 | im | neuronal |
| 1/26 | im | mixed |
| 1/27 | im | mixed |
| 1/28 | im / iv | neuronal |
| 1/29 | im / iv | neuronal |
| 1/30 | im / iv | neuronal |
| 1/31 | im | non neuronal |
| 1/2 | iv | non neuronal |
| 2/2 | im | non neuronal |

Treatment of Nervous System Trauma hES cells and/or their derivatives, wherein said cells comprise neuronal stem cell progenitors and hematopoietic stem cell progenitors according to the practice of the present invention, are administered in an amount of about 750,000 to about 160 million cells for the treatment of Nervous System Trauma, including but not limited to Brain Damage, Coma and Vegetative State. In another embodiment, about 750,000 to about 80 million cells are administered.

While administration protocols may be varied to suit the particular patient, a typical protocol for the treatment of nervous system trauma comprises daily intramuscular and intravenous injections for the first 2 months along with intrathecal and epidural injections.

Treatment of Cerebro-Vascular Accident or Stroke hES cells and/or their derivatives, wherein said cells comprise neuronal stem cell progenitors and hematopoietic stem cell progenitors according to the practice of the present invention, are administered in an amount of about 750,000 to about 160 million cells for treating cerebro-vascular accident or stroke. In another embodiment, about 750,000 to about 80 million cells are administered.

While administration protocols may be varied to suit the particular patient, a typical protocol for the treatment of cerebro-vascular accident comprises daily intramuscular and intravenous injections for two weeks and intravenous infusion for 3 days thereafter during the first month, intravenous infusion for 2 days every 15 days during months 2 and 3, intravenous infusion for 2 days and an intrathecal injection during month 5, and intravenous infusion for 4 days followed by intramuscular injection for 4 days during months 8, 10, and 12.

EXAMPLE 9

A patient diagnosed with Cerebro-Vascular Accident or Stroke suffered from right-sided hemiparesis with drooling, difficulty in swallowing, and inability to talk or walk. In addition, the patient had cancer of the colon. After the treatment according to the present invention, the patient showed signs of improvement as the speech and motor activities improved, the spine straightened, and hemiparesis was cured.

The schedule of injections for this patient is shown in Table 9.

TABLE 9

| Date | Route of administration | Cell types |
| --- | --- | --- |
| 8/17 | test dose | non-neuronal |
| 8/22 | im | hES |
| 8/23 | im × 2 | neuronal hES |
| 8/24 | im × 2 | hES |
| 8/25 | im | hES |
| 8/26 | im × 2 | neuronal |
| 8/29 | im | neuronal |
| 8/30 | iv | neuronal |
| 8/31 | im | neuronal |
| 9/2 | im × 2 | neuronal |
| 9/5 | iv | non-neuronal |
| 9/6 | iv | neuronal |
| 9/7 | im | neuronal |
| 9/8 | iv | neuronal |
| 9/9 | iv | neuronal |
| 9/12 | im | neuronal and non-neuronal mixture |
| 9/13 | iv | neuronal |
| 9/14 | im | non-neuronal |
| 9/19 | iv | neuronal |
| 9/22 | iv | neuronal |
| 9/26 | im | neuronal and non-neuronal mixture |
| 9/29 | iv | neuronal |
| 10/3 | im | neuronal and non-neuronal mixture |
| 10/6 | im | non-neuronal |
| 10/10 | iv | neuronal |
| 10/13 | iv | neuronal |
| 10/17 | iv | neuronal and non-neuronal mixture |
| 10/20 | iv | non-neuronal |
| 10/24 | iv | neuronal and non-neuronal mixture |
| 10/27 | iv | neuronal |
| 10/31 | iv | neuronal and non-neuronal mixture |
| 11/3 | iv | neuronal and non-neuronal mixture |
| 11/7 | im | non-neuronal |
| 11/10 | iv | non-neuronal |
| 11/14 | im | neuronal |
| 11/17 | im | non-neuronal |
| 11/21 | im | non-neuronal |
| 11/24 | im | non-neuronal |
| 12/4 | iv | neuronal and non-neuronal mixture |
| 12/12 | iv | non-neuronal |
| 12/19 | iv | neuronal |
| 12/26 | iv | non-neuronal |
| 1/4 | iv | neuronal |
| 1/11 | iv infusion | neuronal |
| 8/18 | iv im | neuronal |
| 8/21 | iv im | non-neuronal |
| 8/22 | iv im | non-neuronal |
| 8/24 | im iv | non-neuronal |
| 9/1 | iv infusion | non-neuronal |
| 9/2 | iv infusion | non-neuronal |

EXAMPLE 9

An 82 year old man suffered from a cerebral stroke 5 years ago and presented with right sided hemiparesis, with facial asymmetry and slurred speech. He walked with a stick and a huge limp and was not able eat with his right hand due to difficulty in co-ordination. He could not sit or get up on his own and dragged his feet on walking. There was drooling of saliva and he also could not swallow well.

Two months after treatment he is able to walk without support, sits and stands on his own, eats with his right hand, has no slurring speech and no facial asymmetry. He is able to get up from a chair. He is bending the affected knee on walking while maintaining balance.

The schedule of injections for this patient is shown in Table 10.

TABLE 10

| Date | Route of administration | Cell types |
| --- | --- | --- |
| 11/4 | im | non neuronal (test dose) |
| 11/6 | im | non neuronal |
| 11/7 | im | neuronal |
| 11/8 | im | non neuronal |
| 11/9 | im | neuronal |
| 11/10 | im | neuronal |
| 11/11 | im | non neuronal |
| 11/13 | im | non neuronal |
| 11/14 | im | non neuronal |
| 11/15 | iv im | neuronal |
| 11/16 | iv im | neuronal |
| 11/18 | iv im | non neuronal |
| 11/22 | iv infusion | neuronal |
| 11/23 | iv infusion | neuronal |
| 11/24 | im | neuronal |
| 11/27 | im | neuronal |
| 11/28 | im | non neuronal |
| 11/29 | im | neuronal |
| 11/30 | im | neuronal |
| 12/2 | im | non neuronal |
| 12/4 | im | non neuronal |
| 12/5 | iv infusion | neuronal |
| 12/6 | iv infusion im | mixed |
| 12/7 | im | mixed |
| 12/8 | im | mixed |
| 12/9 | im | mixed |
| 12/11 | im | mixed |
| 12/12 | im | mixed |
| 12/14 | im iv | mixed |
| 12/15 | im | mixed |
| 12/16 | im | mixed |
| 12/18 | im | mixed |
| 12/19 | im iv | mixed |
| 12/20 | im | mixed |
| 12/21 | im | mixed |
| 12/22 | im | mixed |
| 12/23 | im | mixed |

TABLE 10-continued

| Date | Route of administration | Cell types |
|------|------------------------|------------|
| 12/25 | im | neuronal |
| 12/26 | im | neuronal |
| 12/27 | iv | mixed |
| 12/28 | im | neuronal |
| 12/29 | im | neuronal |
| 12/30 | im | neuronal |
| 1/1 | im | mixed |
| 1/2 | im | mixed |
| 1/3 | iv | non neuronal |
| 1/4 | im | non neuronal |

Treatment of Familial Nervous System Disorders hES cells and/or their derivatives, wherein said cells comprise neuronal stem cell progenitors and hematopoietic stem cell progenitors according to the practice of the present invention, are administered in an amount of about 750,000 to about 160 million cells to subjects for the treatment of Familial Nervous System Disorders, including but not limited to Olivo Ponto Cerebral Atrophy and Huntington's Chorea. In another embodiment, about 750,000 to about 80 million cells are administered. The routes of administration are intramuscular and intravenous along with intrathecal, epidural catheter and intravenous infusion. This would most likely continue for the person's lifetime but the first year would be an intensive program as follows—daily intramuscular and intravenous injections for at least three months during which time intrathecal, epidural catheter and intravenous infusion are also administered. The same set of injections are administered after a gap of one and a half months over a period of 21 days. The daily intramuscular and intravenous injections are continued and then reduced to thrice a week, twice a week, once a week, once a fortnight and then monthly depending on the patients condition. The intrathecal injection can be repeated at a 4-6 monthly gap as can the epidural catheter. Intravenous infusions can be given every two weeks, every month or every two months.

EXAMPLE 10

A patient diagnosed with Sporadic Spino Cerebellar Ataxia with inability to turn on the bed, walk, or shift his position whilst sitting, had difficulty in speech, had tremors and inability to pick up his neck.

After the stem cell treatment according to the practice of the present invention, improvements in all of the symptoms were noted and the patient was able to balance himself and walk a few steps. The speech became coherent.

The schedule of injections for this patient is shown in Table 11.

TABLE 11

| Date | Route of administration | Cell types |
|------|------------------------|------------|
| 8/8 | test dose | non-neuronal |
| 8/9 | im | neuronal |
| 8/10 | im × 2 | neuronal |
| 8/11 | im × 2 | neuronal |
| 8/12 | im × 2 | neuronal |
| 8/13 | im × 2 | neuronal |
| 8/16 | im × 2 | neuronal |
| 8/17 | im × 2 | non-neuronal |
| 8/18 | im deep spinal | neuronal |
| 8/19 | im | hES |
| 8/23 | im | neuronal hES |

TABLE 11-continued

| Date | Route of administration | Cell types |
|------|------------------------|------------|
| 8/24 | im × 2 | hES |
| 8/25 | im × 2 | hES |
| 8/26 | im × 2 | neuronal |
| 8/29 | im × 2 | neuronal |
| 8/31 | im × 2 | neuronal |
| 9/5 | im iv | non-neuronal |
| 9/7 | im | neuronal |
| 9/12 | im | neuronal |
| 9/15 | epidural | neuronal |
| 9/16 | im | neuronal |
| 9/19 | iv | neuronal |
| 9/22 | iv | neuronal |
| 9/28 | im | neuronal |
| 9/30 | iv | neuronal |
| 10/3 | im iv | neuronal |
| 10/4 | im iv | non-neuronal neuronal and non-neuronal mixture |
| 10/5 | iv | neuronal |
| 10/13 | im | neuronal |
| 10/14 | intra-articular | neuronal |
| 10/17 | iv | neuronal |
| 11/15 | iv | neuronal |
| 11/18 | im | non-neuronal |
| 11/21 | iv | non-neuronal |
| 11/23 | im | non-neuronal |
| 12/1 | im iv | neuronal and non-neuronal mixture |
| 12/6 | im | neuronal and non-neuronal mixture |
| 12/8 | im | non-neuronal |
| 12/13 | im | non-neuronal neuronal |
| 12/15 | epidural | neuronal |
| 12/16 | im | neuronal |
| 12/21 | im | neuronal |
| 12/22 | im iv | neuronal |
| 12/25 | im iv | non-neuronal |
| 3/5 | spinal | non-neuronal |

EXAMPLE 11

A patient with familial Olivo Ponto Cerebral Atrophy was diagnosed at John Hopkins University. Her father, twin sister, and brother were afflicted by the same disease. She could only talk on expiration, was wheelchair bound with continuous dribbling of urine and had to do manual evacuation of feces. She had tremors all over the body and could not balance herself even while sitting down. There would be severe postural hypotension.

After 2 years of treatment the patient goes to the toilet for her bodily functions, talks well, has no tremors and is able to walk with support. There has been no deterioration since even though her twin sister is bedridden with the same disease. There is no postural hypotension and she has definitely not deteriorated.

Treatment of Skin Disorders hES cells and/or their derivatives, wherein said cells comprise hematopoietic stem cell progenitors according to the practice of the present invention, are administered via subcutaneous or intravenous injection or via local or topical application in an amount of about 750,000 to about 160 million cells for the treatment of Skin disorders, including but not limited to Non-Healing Ulcers, Psoriasis, Pressure Sores, and Sarcoidosis. In the case of skin disorders, hES cells may also be used topically to treat the skin disorder or damage. In another embodiment, about 750,000 to about 80 million cells are administered.

In one embodiment, the hES cells or differentiated skin cells and embryonal extract may be mixed with a biocompatible carrier, such as a gel, ointment or paste, and applied to damaged skin or mucosal tissue to accelerate healing as well as to heal wounds resistant to healing, such as diabetic or decubitus ulcers. Alternatively, the cells may be provided in a suspension or emulsion. In one embodiment, the carrier also contains antimicrobial agents, analgesics, or other pharmaceutical agents.

Alternatively, in a different embodiment, hES cells are grown on a sterile artificial porous substrate such as muslin and applied directly to the wound. After 12-24 hours the muslin is removed and the stem cells continue growing, healing the wound. Applied intralesionally, the hES cells differentiate and eventually replace the damaged cells.

EXAMPLE 12

A 70 year old lady suffered a burn injury on her left ankle which did not heal despite conventional therapy. After application of hES cells on the burn site, her wound started healing and three years later the skin is absolutely alright.

Treatment of Auto Immune Disorders hES cells and/or their derivatives, wherein said cells comprise hematopoietic stem cell progenitors according to the practice of the present invention, are administered via intramuscular injection, intravenous injection, subcutaneous injection, intra-articular injection or intravenous infusion or combinations thereof in an amount of about 750,000 to about 160 million cells for the treatment of Auto-Immune Disorders including but not limited to Systemic Lupus Erythematosus, Ankylosing Spondylitis, Cardiomyopathy, Sarcoidosis, Arthritis, and Ulcerative Colitis. In another embodiment, about 750,000 to about 80 million cells are administered. The administration of the hES cells is highly effective not only in the treatment of autoimmune disorders but also in the restoration of a suppressed immune system. As an alternative to treatment with immunosuppressors or as a method for "priming" patients for organ transplant or other medical intervention, hES cells and their derivatives may be used to allow acceptance of the organ through reduction in host-graft rejection processes.

While administration protocols may be varied to suit the particular patient, a typical protocol for the treatment of autoimmune disorders comprises daily injections for the first 2 months, alternate day injections along with an intravenous infusion during month 3, weekly injections along with a 2 day continuous intravenous infusion every 15 days during months 5-7 and 10-12, and booster injections every 3 months for a year and then every 6 months for a year.

EXAMPLE 13

A patient suffering from psoriasis for the past 26 years was wheelchair bound with hypertension, diabetes mellitus and psoriatic arthritis with huge ulcers on her leg which were non healing and not amenable to skin grafting.

After receiving therapy for 6 months she has no ulcers and no arthritis. Her diabetes and hypertension were under control. She has started walking on her own and has started all activities and is receiving booster shots for the past 1 year. She claims that she has walked for the first time in the past 26 years and is able to do all her household chores on her own.

Stem cell treatment was made locally to the sores and the sores healed. Also after the treatment no further sores were detected. The scaliness and itchiness of the skin and the swelling of the legs also was reduced. The diabetic condition was also cured with controlled blood pressure that led to a reduction in medication.

The schedule of injections for this patient is shown in Table 12.

TABLE 12

| Date | Route of administration | Cell types |
|---|---|---|
| 12/27 | test dose | non-neuronal |
| 1/22 | im | non-neuronal |
| 2/20 | im | neuronal |
| 2/23 | im | neuronal |
| 2/28 | m | neuronal |
| 4/1 | im | neuronal |
| 4/7 | im | neuronal and non-neuronal mixture |
| 4/10 | im | neuronal and non-neuronal mixture |
| 4/21 | m | neuronal and non-neuronal mixture |
| 6/29 | im | non-neuronal |
| 7/6 | m | non-neuronal |
| 7/29 | im | non-neuronal |
| 10/17 | im spray | non-neuronal |
| 11/1 | im spray | neuronal and non-neuronal mixture |
| 11/2 | im spray | neuronal and non-neuronal mixture |
| 11/3 | im spray | neuronal and non-neuronal mixture |
| 11/4 | im × 2 | neuronal |
| 11/5 | iv spray | non-neuronal |
| 11/6 | im spray | non-neuronal |
| 11/7 | im spray | non-neuronal |
| 11/11 | iv spray | neuronal |
| 11/14 | iv spray | neuronal |
| 11/15 | im spray | non-neuronal |
| 11/16 | im | non-neuronal |
| 11/21 | iv | non-neuronal |
| 11/23 | im | non-neuronal |
| 11/29 | im | neuronal and non-neuronal mixture |
| 1/4 | im | non-neuronal |
| 3/28 | im | non-neuronal |

Treatment of Blood Disorders

Yet another embodiment of method according to the practice of the present invention is in the treatment of Blood Disorders such as Thrombocytopenia, Thalassemia, Acute Myeloid Leukaemia by intravenous injection of hES cells and/or their derivatives, wherein said cells comprise hematopoietic stem cell progenitor cells. Cells are administered for 10 days to 14 days and then repeated as a weekly shot for benign conditions. For malignant conditions the injections are given daily for 40 days and then repeated if there is a relapse.

Treatment of Genetic Disorders

Another embodiment of hES cell transplantation methods according to the practice of the present invention is in the treatment of Genetic Disorders including but not limited to Down's Syndrome, Friedereich's Ataxia, Huntington's Chorea, Asperger's Syndrome and Spinomuscular Atrophy The symptoms of genetic disorders are manifested by mental retardation, musculoskeletal dysfunction and organ failure in combination or alone and result in serious incurable debilitation and reduced life expectancy. In the case of patients suffering from a genetic disorder, hES cells are administered to the patient according to the practice of the present invention and, once administered, differentiate to provide the patient with a population of cells expressing the missing or compromised gene product with an ensuing restoration of intracellular homeostasis.

While administration protocols may be varied to suit the particular patient, a typical protocol for the treatment of Genetic Disorders comprises daily intramuscular and intravenous injections for the first month, alternate day injections during month 2, injections twice a week during month 3, once a week injections during months 5, 7, 9, 11, and 12, and booster injections every 3 months for a year. Also intravenous infusions are given every 15 days

EXAMPLE 14

A patient with Down's syndrome showed no response to verbal commands, was not able to go up and down stairs and had low body weight as a result of eating difficulties. The patient was unable to eat, displayed a typical wide stance, and suffered from frequent coughs and colds. The eyes were mongoloid.

Pursuant to the treatment according to the present invention, the patient is able to understand and carry out verbal commands, started speaking, and started walking up and down the stairs. DQ testing has shown the mental age to be 1 year behind her chronological age as against 2 years 6 months behind within a span of less than a year. Socially, she goes to school and plays with other children. She also feeds herself.

The schedule of injections for this patient is shown in Table 13.

TABLE 13

| Date | Route of administration | Cell types |
| --- | --- | --- |
| 7/8 | test dose | non-neuronal |
| 7/16 | im | neuronal |
| 7/25 | im | neuronal |
| 7/26 | im | neuronal |
| 7/27 | im | neuronal |
| 7/30 | im | neuronal |
| 8/3 | im | neuronal |
| 8/10 | im | neuronal |
| 8/12 | im | neuronal |
| 8/16 | im | neuronal |
| 8/18 | im | neuronal |
| 8/22 | im | hES |
| 8/26 | im | neuronal |
| 8/29 | im | neuronal |
| 8/31 | im | neuronal |
| 9/2 | im | neuronal |
| 9/6 | im | neuronal |
| 9/8 | im | non-neuronal |
| 9/13 | im | non-neuronal |
| 9/19 | im | neuronal and non-neuronal mixture |
| 9/22 | im | non-neuronal |
| 9/30 | im | non-neuronal |
| 10/3 | im | neuronal and non-neuronal mixture |
| 10/10 | im | non-neuronal |
| 10/18 | im | non-neuronal |
| 10/27 | im | neuronal |
| 11/7 | im | non-neuronal |
| 11/8 | im | non-neuronal |
| 11/9 | im | non-neuronal |
| 11/10 | im | non-neuronal |
| 11/11 | im | neuronal |
| 11/14 | im | neuronal |
| 11/17 | im | non-neuronal |
| 11/18 | im | non-neuronal |
| 11/21 | im | non-neuronal |
| 11/22 | im | non-neuronal |
| 11/23 | im | non-neuronal |
| 11/25 | im | non-neuronal |
| 11/28 | im | neuronal and non-neuronal mixture |
| 12/4 | im | neuronal and non-neuronal mixture |

TABLE 13-continued

| Date | Route of administration | Cell types |
| --- | --- | --- |
| 12/8 | im | non-neuronal |
| 12/12 | im | non-neuronal |
| 12/15 | im | neuronal |
| 12/19 | im | neuronal |
| 12/27 | iv | neuronal |
| 1/4 | im | non-neuronal |
|  | iv |  |
| 1/11 | im | non-neuronal |
|  |  | neuronal |
| 1/19 | im | neuronal |
| 1/20 | im | non-neuronal |
| 1/23 | im | non-neuronal |
| 1/30 | im | neuronal |
| 2/9 | im | neuronal |
| 2/13 | im | neuronal |
| 2/23 | im | neuronal |
| 2/27 | im | neuronal |
| 3/10 | im | neuronal |
| 3/14 | im | neuronal |
| 3/20 | im | neuronal |
| 5/11 | im | neuronal |
| 5/15 | im | neuronal |
| 5/16 | im | neuronal |
| 5/17 | im | neuronal |
| 5/18 | im | neuronal |
| 5/22 | im | neuronal |
| 5/23 | im | neuronal |
| 7/3 | im | neuronal |
| 7/5 | im | neuronal |
| 7/11 | im | neuronal |
| 7/13 | im | neuronal |
| 7/17 | im | neuronal |
| 7/19 | im | neuronal |
| 7/21 | iv | neuronal |
| 7/24 | im | neuronal |
| 7/28 | im | non-neuronal |
| 7/31 | im | neuronal |
| 8/2 | im | non-neuronal |
| 8/21 | im | non-neuronal |
| 8/23 | im | non-neuronal |
| 8/28 | im | non-neuronal |
| 8/30 | im | non-neuronal |

EXAMPLE 15

A 3 year old girl was diagnosed with Down's syndrome. She was not able to talk, comprehend, or walk up and down the stairs. She did not eat on her own and her single word limited speech was very unclear.

After 8 months of treatment she understands everything, speaks three word sentences, and recognizes colors, shapes and sizes. She is able to go up and down the stairs on her own and has started eating on her own.

The schedule of injections for this patient is shown in Table 14.

TABLE 14

| Date | Route of administration | Cell types |
| --- | --- | --- |
| 1/30 | im | neuronal (test dose) |
| 2/6 | im | neuronal |
| 2/7 | im | neuronal |
| 2/8 | im | neuronal |
| 2/9 | im | neuronal |
| 2/10 | im | non-neuronal |
| 2/13 | im | neuronal |
| 2/15 | im | neuronal |
| 2/16 | im | neuronal |
| 2/17 | im | neuronal |
| 2/20 | im | neuronal |
| 2/22 | im | neuronal |

TABLE 14-continued

| Date | Route of administration | Cell types |
|---|---|---|
| 2/24 | im | non-neuronal |
| 2/27 | im | neuronal |
| 3/1 | im | neuronal |
| 3/3 | im | non-neuronal |
| 3/6 | im | non-neuronal |
| 3/13 | im | neuronal |
| 3/15 | im | neuronal |
| 3/22 | im | neuronal |
| 3/24 | im | neuronal |
| 3/26 | im | neuronal |
| 3/27 | im | non-neuronal |
| 3/29 | im | neuronal |
| 4/3 | im | neuronal |
| 4/5 | im | neuronal |
| 4/7 | im | neuronal |
| 4/10 | im | neuronal |
| 4/12 | im | non-neuronal |
| 4/14 | im | non-neuronal |
| 4/21 | im | neuronal |
| 4/24 | im | neuronal |
| 4/26 | im | neuronal |
| 4/28 | im | neuronal |
| 5/1 | im | neuronal |
| 5/10 | im | neuronal |
| 5/12 | im | neuronal |
| 5/13 | im | non-neuronal |
| 5/22 | im | neuronal |
| 5/24 | im | neuronal |
| 5/29 | im | neuronal |
| 6/5 | im | neuronal |
| 6/7 | im | neuronal |
| 6/10 | im | neuronal |
| 6/14 | im | neuronal |
| 6/16 | im | neuronal |
| 6/19 | im | neuronal |
| 6/21 | im | neuronal |
| 6/23 | iv | non-neuronal |
| 6/27 | im | neuronal |
| 6/29 | im | neuronal |
| 7/3 | im | neuronal |
| 7/5 | im | neuronal |
| 7/12 | im | neuronal |
| 7/14 | im | neuronal |
| 7/17 | im | neuronal |
| 7/19 | im | neuronal |
| 7/21 | im | neuronal |
| 7/27 | im | neuronal |
| 7/28 | im | non-neuronal |
| 8/1 | im | non-neuronal |
| 8/3 | im | non-neuronal |
| 8/5 | im | non-neuronal |
| 8/7 | im | non-neuronal |
| 8/19 | im | non-neuronal |
| 8/24 | im | non-neuronal |
| 8/26 | im | neuronal |
| 8/28 | im | non-neuronal |
| 8/31 | im | non-neuronal |
| 9/2 | im | non-neuronal |
| 9/7 | im | non-neuronal |
| 9/9 | im | non-neuronal |
| 9/11 | im | non-neuronal |
| 9/14 | im | non-neuronal |
| 9/21 | im | non-neuronal |
| 9/23 | im | non-neuronal |
| 9/25 | im | non-neuronal |
| 9/28 | im | non-neuronal |
| 9/29 | im | non-neuronal |
| 10/4 | im | non-neuronal |
| 10/7 | im | non-neuronal |
| 10/10 | im | non-neuronal |
| 10/14 | im | non-neuronal |
| 10/16 | im | non-neuronal |
| 10/18 | im | non-neuronal |
| 10/22 | im | non-neuronal |
| 10/26 | im | non-neuronal |
| 10/28 | im | non-neuronal |
| 11/1 | im | non-neuronal |
| 11/4 | im | non-neuronal |
| 11/7 | im | non-neuronal |
| 11/9 | im | non-neuronal |
| 11/13 | im | non-neuronal |
| 11/16 | im | non-neuronal |
| 11/17 | im | non-neuronal |
| 11/20 | im | non-neuronal |
| 11/23 | im | non-neuronal |
| 11/27 | im | non-neuronal |
| 11/30 | im | non-neuronal |
| 12/3 | im | non-neuronal |
| 12/4 | im × 2 | non-neuronal |
| 12/7 | im | non-neuronal |
| 12/9 | im | non-neuronal |
| 12/11 | im | non-neuronal |
| 12/14 | im × 2 | non-neuronal |
| 12/16 | im | non-neuronal |
| 12/21 | im | non-neuronal |
| 12/24 | im | non-neuronal |
| 12/27 | im | neuronal |
| 1/1 | im | mixed |
| 1/3 | im | non neuronal |
| 1/6 | im | non neuronal |
| 1/9 | im | non neuronal |
| 1/12 | im | non neuronal |
| 1/15 | im | non neuronal |
| 1/18 | im | non neuronal |
| 1/22 | im | mixed |
| 1/25 | im | neuronal |
| 1/28 | im | neuronal |

EXAMPLE 16

A 13 year old boy suffered from a genetic defect with lack of concentration, frequent fits and sight impairment. He had total tunnel vision. He had difficulty sitting in class and seeing the blackboard even though he was sitting in the front row. He had delayed milestones and if he read something he would have to read it thrice to remember what he read. He also had difficulty in locating items in a room.

Since starting hES cells his sight has improved and he sits two rows back in the classroom and can see the black board much better. He is able to remember much more and his response time to verbal commands has improved. He does not have fits as much as before and his medication has been reduced. Reports from the ophthalmologist show that the deadened areas in the periphery have been restored.

The schedule of injections for this patient is shown in Table 15.

TABLE 15

| Date | Route of administration | Cell types |
|---|---|---|
| 6/8 | im | neuronal (test dose) |
| 6/9 | im | neuronal |
| 6/12 | im | neuronal |
| 6/13 | im | neuronal |
| 6/14 | im | non neuronal |
| 6/15 | im | non neuronal |
| 6/16 | im | neuronal |
| 6/20 | im | neuronal |
| 6/21 | im | non neuronal |
| 6/22 | im | neuronal |
| 6/23 | iv | non neuronal |
| 6/27 | im | neuronal |
| 6/28 | im | neuronal |
| 6/29 | im | neuronal |
| 7/3 | im | non neuronal |
| 7/4 | im | neuronal |
| 7/5 | im | neuronal |
| 7/6 | im | neuronal |

TABLE 15-continued

| Date | Route of administration | Cell types |
|---|---|---|
| 7/7 | im | neuronal |
| 7/10 | im | neuronal |
| 7/11 | im | neuronal |
| 7/12 | im | neuronal |
| 7/13 | im | non neuronal |
| 7/14 | im | neuronal |
| 7/17 | im | neuronal |
| 7/18 | im | neuronal |
| 7/20 | im | neuronal |
| 7/21 | iv infusion | neuronal |
| 7/22 | iv infusion | neuronal |
| 7/24 | im | neuronal |
| 7/25 | im | neuronal |
| 7/26 | im | neuronal |
| 7/27 | im | neuronal |
| 7/28 | im | non neuronal |
| 7/31 | im | non neuronal |
| 8/2 | im | non neuronal |
| 8/3 | im | non neuronal |
| 8/4 | im | non neuronal |
| 8/7 | im | non neuronal |
| 8/8 | im | non neuronal |
| 8/9 | im | non neuronal |
| 8/10 | im × 2 | non neuronal |
| 8/11 | iv infusion | non neuronal |
| 8/12 | iv infusion | non neuronal |
| 8/13 | im | non neuronal |
| 8/14 | im | non neuronal |
| 8/17 | im × 2 | non neuronal |
| 8/18 | im | non neuronal |
| 8/21 | im | non neuronal |
| 8/22 | im | non neuronal |
| 8/23 | im | non neuronal |
| 8/24 | im | non neuronal |
| 8/25 | im | non neuronal |
| 8/2/ | im | non neuronal |
| 8/29 | im | non neuronal |
| 8/30 | im | non neuronal |
| 9/2 | iv infusion | non neuronal |
| 9/3 | iv infusion | non neuronal |
| 9/4 | im × 3 | non neuronal |
| 9/5 | im | non neuronal |
| 9/6 | im | non neuronal |
| 9/7 | im | non neuronal |
| 9/8 | im | non neuronal |
| 9/11 | im | non neuronal |
| 9/13 | im | non neuronal |
| 9/14 | im | non neuronal |
| 9/16 | im | non neuronal |
| 9/18 | im | non neuronal |
| 9/19 | im | non neuronal |
| 9/21 | im × 2 | non neuronal |
| 9/22 | iv infusion | non neuronal |
| 9/23 | iv infusion | non neuronal |
| 10/3 | im | non neuronal |
| 10/4 | im | non neuronal |
| 10/5 | im | non neuronal |
| 10/6 | im | non neuronal |
| 10/9 | im | non neuronal |
| 10/10 | im | non neuronal |
| 10/11 | im | non neuronal |
| 10/12 | im | non neuronal |
| 10/13 | retroorbital | neuronal |
| 10/16 | im | non neuronal |
| 10/17 | im | non neuronal |
| 10/18 | im | non neuronal |
| 10/20 | im | non neuronal |
| 10/23 | im | non neuronal |
| 10/24 | im | non neuronal |
| 10/25 | im | non neuronal |
| 10/26 | im | non neuronal |
| 10/27 | iv infusion | non neuronal |
| 10/28 | iv infusion × 3 | non neuronal |
| 10/31 | im × 2 | non neuronal |
| 11/2 | im × 2 | non neuronal |
| 11/3 | im × 2 | non neuronal |
| 11/6 | im × 2 | non neuronal |
| 11/8 | im | non neuronal |
| 11/9 | im | non neuronal |
| 11/10 | im | non neuronal |
| 11/13 | im | non neuronal |
| 11/14 | retroorbital | neuronal |
| 11/15 | im | non neuronal |
| 11/16 | im | non neuronal |
| 11/17 | im | non neuronal |
| 11/20 | im | non neuronal |
| 11/21 | im | non neuronal |
| 11/23 | im | non neuronal |
| 11/24 | im | non neuronal |
| 11/29 | im | non neuronal |
| 11/30 | iv | mixed |
| 12/1 | iv infusion | mixed |
| 12/4 | im | non neuronal |
| 12/5 | iv | mixed |
| 12/6 | im | non neuronal |
| 12/7 | im | non neuronal |
| 12/8 | im | non neuronal |
| 12/11 | im | non neuronal |
| 12/12 | im | non neuronal |
| 12/13 | im | non neuronal |
| 12/14 | im | non neuronal |
| 12/18 | im | non neuronal |
| 12/19 | iv | non neuronal |
| 12/21 | im | non neuronal |
| 12/22 | retroorbital | neuronal |
| 12/29 | im | neuronal |
| 2/2 | im | non neuronal |

EXAMPLE 17

The patient is a 32 year male suffering from Fredrick's ataxia and whose sister died of the disease. He could not stand, had fading speech, difficulty in swallowing, was wheelchair bound, and needed assistance in going to the toilet. He was previously treated in Germany and the U.S. with no results. His heart was dilating and functioning at 15 to 20%.

Since starting hES cells, he has shown improvement. He is able to speak much clearer and has no difficulty in swallowing. His heart has improved with all the dimensions coming back to normal and the functioning capacity up to 58 to 60%. There has been no deterioration.

The schedule of injections for this patient is shown in Table 16.

TABLE 16

| Date | Route of administration | Cell types |
|---|---|---|
| 2/17 | im | non neuronal (test dose) |
| 2/20 | im | neuronal |
| | iv | non neuronal |
| 2/21 | im | neuronal |
| | iv | non neuronal |
| 2/22 | im | neuronal |
| | iv | non neuronal |
| 2/23 | im | neuronal |
| | iv | non neuronal |
| 2/24 | im | neuronal |
| | iv | non neuronal |
| 2/25 | im | neuronal |
| | iv | non neuronal |
| 2/26 | im | neuronal |
| | iv | non neuronal |

TABLE 16-continued

| Date | Route of administration | Cell types |
|---|---|---|
| 2/27 | epidural | neuronal |
| 2/28 | im | neuronal |
|  | iv | non neuronal |
| 3/1 | im | neuronal |
|  | iv | non neuronal |
| 3/2 | im | neuronal |
|  | iv | non neuronal |
| 3/3 | im | neuronal |
|  | iv | non neuronal |
| 3/4 | im | neuronal |
|  | iv | Non neuronal |
| 3/5 | im | neuronal |
|  | iv | non neuronal |
| 3/6 | im | neuronal |
|  |  | non neuronal |
| 3/7 | epidural (catheter) | neuronal |
| 3/8 | epidural (catheter) | neuronal |
| 3/9 | epidural (catheter) | neuronal |
| 3/10 | epidural (catheter) | neuronal |
| 3/13 | im | neuronal |
|  | iv | non neuronal |
| 3/14 | im | non neuronal |
| 3/16 | im | non neuronal |
| 3/17 | im | neuronal |
|  | iv | non neuronal |
| 3/18 | im | neuronal |
|  | iv | non neuronal |
| 3/19 | im | neuronal |
|  | iv | non neuronal |
| 3/20 | im | neuronal |
|  | iv | non neuronal |
| 3/21 | im | non neuronal |
| 3/22 | im | non neuronal |
| 3/24 | im | neuronal |
|  | iv | non neuronal |
| 3/25 | im | non neuronal |
| 3/26 | im | non neuronal |
| 3/27 | im | neuronal |
| 3/28 | im | non neuronal |
| 3/29 | im | non neuronal |
| 3/30 | im | non neuronal |
| 3/31 | im | non neuronal |
| 4/1 | im | non neuronal |
| 4/2 | im | non neuronal |
| 4/3 | im | non neuronal |
| 4/4 | im | neuronal |
|  | iv | non neuronal |
| 4/5 | im | non neuronal |
| 4/6 | im | non neuronal |
| 4/7 | im | non neuronal |
| 4/8 | im | non neuronal |
| 4/9 | im | neuronal |
|  | iv | non neuronal |
| 4/10 | im | neuronal |
|  | iv | non neuronal |
| 4/11 | im | non neuronal |
| 4/15 | im | non neuronal |
| 4/16 | im | non neuronal |
| 4/18 | im | neuronal |
|  | iv | non neuronal |
| 4/19 | im | neuronal |
|  | iv | non neuronal |
| 4/20 | im | neuronal |
|  | iv | non neuronal |
| 4/21 | im | non neuronal |
| 4/22 | im | non neuronal |
| 4/24 | im | non neuronal |
| 4/25 | im | non neuronal |
| 4/26 | iv | neuronal |
|  | im | non neuronal |
| 4/27 | iv | neuronal |
|  | im | non neuronal |
| 4/29 | iv | neuronal |
| 4/30 | iv | neuronal |
|  | im | non neuronal |
| 502 | im | non neuronal |
| 5/3 | iv | neuronal |
| 5/5 | iv | neuronal |
|  | epidural |  |
| 5/7 | iv | neuronal |
|  | im | non neuronal |
| 5/9 | iv | neuronal |
|  | im | non neuronal |
| 5/10 | iv | neuronal |
|  | im | non neuronal |
| 5/12 | iv | neuronal |
|  | im | non neuronal |
| 5/13 | iv | neuronal |
|  | im | non neuronal |
| 5/14 | iv | neuronal |
|  | im | non neuronal |
| 5/16 | epidural (intrathecal) | neuronal |
| 5/18 | iv | neuronal |
|  | im | non neuronal |
| 8/26 | im | non neuronal |
|  | iv |  |
| 8/27 | im | non neuronal |
|  | iv |  |
| 8/28 | iv | non neuronal |
|  | iv infusion |  |
| 8/29 | iv | non neuronal |
|  | iv infusion |  |
| 8/30 | im | non neuronal |
|  | iv |  |
| 8/31 | im | non neuronal |
|  | iv |  |
| 9/4 | im | non neuronal |
|  | iv |  |
| 9/6 | im | non neuronal |
|  | iv |  |
| 9/7 | im | non neuronal |
|  | iv |  |
| 9/9 | im | non neuronal |
|  | iv |  |
| 9/10 | epidural (intrathecal) | neuronal |
| 9/12 | im | non neuronal |
|  | iv |  |
| 9/14 | im | non neuronal |
|  | iv |  |
| 9/15 | epidural (catheter) | neuronal, |
| 9/16 | epidural (catheter) | neuronal, |
| 9/17 | epidural (catheter) | neuronal |
| 9/18 | im | non neuronal |
|  | iv |  |
| 9/19 | im | non neuronal |
|  | iv |  |
| 9/20 | iv | non neuronal |
|  | iv infusion |  |
| 9/21 | iv | non neuronal |
|  | iv infusion |  |

Treatment of Eye Disorders

Another use of hES Cell transplantation according to the practice of the present invention is in the treatment of Eye Disorders including but not limited to Optical Nerve Atrophy, Macular Degeneration, Eye Damage, Corneal Graft Rejection and Retinitis Pigmentosa through direct injection of neuronal progenitors and hES cells according to the practice of the present invention to the retrobulbar portion of the eye, superficial area of the eye and the internal chamber of the eye.

While administration protocols may be varied to suit the particular patient, a typical protocol for the treatment of Eye Disorders comprises 10 days of intramuscular and intravenous injections followed by a retrobulbar or intravitreous injection, 15 days of intramuscular and intravenous injections followed by a retrobulbar injection, 2 intravenous infusions, and a retrobulbar injection after 2 months. A total of 4 retrobulbar injections is given over a period of 8 months to one year before results are seen but in some cases the results are seen earlier. Intravitreous routes can be used. Also the cornea can be repaired via usage of contact lenses on which the stem cells have been grown. Also eye drops comprising stem cells can be used.

EXAMPLE 18

A patient diagnosed for Optical Nerve Atrophy had conditions which included difficulty in reading small letters and not being able to see objects placed far away. Also dark blue and violet colours were not visible. Vision was nil with perception of light and now is 6/24.

Pursuant to the stem cell therapy according to the present invention, i.e., hES cells and their derivatives including neuronal stem cell progenitors administered by retrobulbar injection and hES cells and their derivatives including neuronal stem cell progenitors and hematopoietic stem cell progenitors according to the practice of the present invention is administered via local intravenous injection, or subcutaneous injection or intramuscular injection, intravitreous injection or topical application in an amount of about 750,000 to about 160 million cells, the patient showed significant improvements. He is able to read time and can see billboards as well as watch television from a distance.

The schedule of injections for this patient is shown in Table 17.

TABLE 17

| Date | Route of administration | Cell types |
|---|---|---|
| 2/14 | im | neuronal |
| 2/15 | iv | neuronal non-neuronal |
| 3/20 | iv × 2 im | neuronal |
| 3/21 | iv retrobulbar | neuronal |
| 4/30 | iv | non-neuronal |
| 5/1 | iv im | neuronal |
| 5/2 | retrobulbar | non-neuronal |

Treatment of Liver and Kidney Disorders

Yet another use of hES cell transplantation according to the practice of the present invention is in the treatment of Liver Disorders and Kidney Disorders including but not limited to End Stage Renal Nephrosis and Nephrotic Syndrome through transplantation according to the practice of the present invention. The routes of administration are intravenous, intramuscular and via intravenous infusion.

EXAMPLE 19

A patient diagnosed for nephrotic syndrome exhibited elevated urea, creatine and P protein levels. The corticomedullary differentiation was not maintained and the body was swollen. hES cells and their derivatives including hematopoietic stem cell progenitors, albumin producing stem cell progenitors and bilirubin producing stem cell progenitors according to the practice of the present invention were administered via intravenous injection, or subcutaneous injection, or intramuscular injection, or intravenous infusion in an amount of about 750,000 to about 160 million cells. After the treatment with stem cells, the body was less swollen and the corticomedullary differentiation was restored. The urea, creatine and P protein levels also normalized.

The schedule of injections for this patient is shown in Table 18.

TABLE 18

| Date | Route of administration | Cell types |
|---|---|---|
| 8/10 | test dose | neuronal |
| 8/11 | im | neuronal |
| 8/12 | im | neuronal |
| 8/16 | im | hES |
| 8/22 | im | hES |
| 8/24 | im | hES |
| 8/25 | im | neuronal |
| 8/29 | im | neuronal |
| 9/1 | im | neuronal |
| 9/7 | im | neuronal |
| 9/8 | im | non-neuronal |
| 9/12 | im | neuronal and non-neuronal mixture |
| 9/19 | im | neuronal and non-neuronal mixture |
| 10/3 | im | neuronal and non-neuronal mixture |
| 10/10 | im | neuronal and non-neuronal mixture |
| 10/11 | iv | neuronal and non-neuronal mixture |
| 10/31 | iv | non-neuronal |
| 11/10 | im | non-neuronal |
| 11/21 | im | non-neuronal |
| 12/8 | im | non-neuronal |
| 12/23 | iv | non-neuronal |
| 2/7 | im | non-neuronal |
| 8/24 | im | non-neuronal |
| 8/25 | im | non-neuronal |
| 9/9 | im | non-neuronal |

Treatment of Musculo-Skeletal Disorders

Another use of hES cell transplantation according to the practice of the present invention is in the treatment of Musculo-Skeletal Disorders including but not limited to Arthritis, Duchenne's Muscular Dystrophy, Limb Girdle Dystrophy, Spinal Muscular Atrophy and Becker's Muscular Atrophy.

While administration protocols may be varied to suit the particular patient, a typical protocol for the treatment of Musculo-Skeletal Disorders comprises daily intramuscular or intravenous injections during the first month, injections twice a week during months 3, 5, 6, and 7, weekly injections during months 9-12 and booster injections every 3 months. Intravenous infusions are given every 10 to 15 days and deep spinal muscular injections are given every 15 to 30 days.

EXAMPLE 20

The case history of a patient diagnosed with Duchenne's Muscular Dystrophy showed symptoms such as listlessness, swollen thighs and face, and positive Gower's sign, with high levels of creatine phosphokinase (CPK) at 10,000 units.

After the treatment of the patient with hES cells and their derivatives including neuronal stem cell progenitors and hematopoietic stem cell progenitors alone or in combination via intravenous injection, or subcutaneous injection, or intramuscular injection, or intravenous catheter infusion, or epidural catheter infusion or sub arachnoid block catheter infusion for a predetermined period, CPK levels fell drastically to 1198 units and Gower's sign was negative.

The schedule of injections for this patient is shown in Table 19.

TABLE 19

| Date | Route of administration | Cell types |
|---|---|---|
| 3/18 | test dose | non-neuronal |
| 3/19 | im | neuronal |
| 3/20 | im × 2 | neuronal |
| 3/25 | im × 2 | non-neuronal |
| 3/26 | im × 2 | non-neuronal |
| 3/27 | im × 4 | neuronal × 2 |
|  |  | non-neuronal × 2 |
| 3/28 | im × 4 | neuronal × 2 |
|  |  | non-neuronal × 2 |
| 3/29 | im × 4 | neuronal × 2 |
|  |  | non-neuronal × 2 |
| 3/30 | im × 4 | neuronal × 2 |
|  |  | non-neuronal × 2 |
| 3/31 | im × 4 | neuronal |
|  |  | non-neuronal × 3 |
| 4/1 | im × 4 | neuronal × 2 |
|  |  | non-neuronal × 2 |
| 4/2 | im × 3 | neuronal |
|  |  | non-neuronal × 2 |
| 4/3 | im × 4 | neuronal × 2 |
|  |  | non-neuronal × 2 |
| 4/4 | im × 4 | neuronal × 2 |
|  |  | non-neuronal × 2 |
| 4/5 | im × 4 | neuronal × 2 |
|  |  | non-neuronal × 2 |
| 4/6 | im × 4 | neuronal × 2 |
|  |  | non-neuronal × 2 |
| 4/7 | im × 4 | neuronal × 2 |
|  |  | non-neuronal × 2 |
| 4/8 | im × 4 | neuronal × 2 |
|  |  | non-neuronal × 2 |
| 4/9 | im × 4 | neuronal × 2 |
|  |  | non-neuronal × 2 |
| 4/10 | im × 4 | neuronal × 2 |
|  |  | non-neuronal × 2 |
| 4/11 | im × 4 | neuronal × 2 |
|  |  | non-neuronal × 2 |
| 4/12 | im × 4 | neuronal × 2 |
|  |  | non-neuronal × 2 |
| 4/13 | im × 4 | neuronal × 2 |
|  |  | non-neuronal × 2 |
| 4/14 | im × 4 | neuronal × 2 |
|  |  | non-neuronal × 2 |
| 4/15 | im × 4 | neuronal × 2 |
|  |  | non-neuronal × 2 |
| 4/16 | im × 4 | neuronal × 2 |
|  |  | non-neuronal × 2 |
| 4/17 | im × 5 | neuronal × 3 |
|  |  | non-neuronal × 2 |
| 4/18 | im × 3 | neuronal |
|  |  | non-neuronal × 2 |
| 4/19 | im × 3 | neuronal × 2 |
|  |  | non-neuronal |
| 4/20 | im × 3 | neuronal |
|  |  | non-neuronal × 2 |
| 4/21 | im × 3 | neuronal |
|  |  | non-neuronal × 2 |
| 4/22 | im × 3 | neuronal |
|  |  | non-neuronal × 2 |
| 4/23 | im × 3 | neuronal × 2 |
|  |  | non-neuronal |
| 4/24 | im × 4 | neuronal × 2 |
|  |  | non-neuronal × 2 |
| 4/25 | im × 3 | neuronal |
|  |  | non-neuronal × 2 |
| 4/26 | im × 2 | neuronal |
|  |  | non-neuronal |
| 7/1 | im × 2 | neuronal |
|  |  | non-neuronal |
| 7/2 | im × 4 | neuronal × 2 |
|  |  | non-neuronal × 2 |
| 7/3 | im × 4 | neuronal × 2 |
|  |  | non-neuronal × 2 |
| 7/4 | im × 2 | neuronal |
|  |  | non-neuronal |
| 7/5 | iv infusion × 2 | neuronal |
| 7/6 | iv infusion × 2 | neuronal |
| 7/7 | im × 2 | neuronal |
| 7/8 | im × 2 | neuronal |
| 7/9 | im × 2 | neuronal |
|  |  | non-neuronal |
| 7/10 | im × 2 | neuronal |
|  |  | non-neuronal |
| 7/11 | im × 2 | neuronal |
|  |  | non-neuronal |
| 7/12 | im × 2 | neuronal |
|  |  | non-neuronal |
| 7/13 | im × 2 | neuronal |
|  |  | non-neuronal |
| 7/14 | im × 2 | neuronal |
|  |  | non-neuronal |
| 7/15 | im × 2 | neuronal |
|  |  | non-neuronal |
| 7/16 | im × 3 | neuronal |
| 7/17 | iv infusion | neuronal |
|  | im × 2 | non-neuronal |
| 7/18 | iv infusion | neuronal |
|  | im × 2 | non-neuronal |
| 7/19 | im × 4 | neuronal × 2 |
|  |  | non-neuronal × 2 |
| 7/20 | im × 4 | neuronal × 2 |
|  |  | non-neuronal × 2 |
| 7/21 | im × 4 | neuronal × 2 |
|  |  | non-neuronal × 2 |
| 7/22 | im × 4 | neuronal × 2 |
|  |  | non-neuronal × 2 |
| 7/23 | iv × 2 | neuronal × 2 |
|  | im × 4 | non-neuronal × 4 |
| 7/24 | im × 4 | neuronal × 2 |
|  |  | non-neuronal × 2 |
| 7/25 | iv | neuronal × 2 |
|  | im × 4 | non-neuronal × 4 |
| 7/26 | im × 4 | neuronal × 2 |
|  |  | non-neuronal × 2 |
| 7/27 | iv | neuronal × 2 |
|  | im × 4 | non-neuronal × 4 |
| 7/28 | im × 4 | neuronal |
|  |  | non-neuronal × 3 |
| 7/29 | iv | non-neuronal |
|  | im × 4 |  |
| 7/30 | im × 4 | neuronal × 2 |
|  |  | non-neuronal × 2 |
| 7/31 | iv | neuronal × 2 |
|  | im × 4 | non-neuronal × 3 |
| 8/1 | im × 4 | neuronal × 2 |
|  |  | non-neuronal × 2 |
| 8/2 | im × 4 | non-neuronal |
| 8/3 | iv infusion × 2 | non-neuronal |
| 8/4 | iv infusion × 2 | non-neuronal |
| 8/5 | im × 4 | non-neuronal |
| 8/6 | im × 4 | non-neuronal |
| 8/7 | iv infusion | non-neuronal |
|  | im × 2 |  |
| 8/8 | iv infusion | non-neuronal |
|  | im × 2 |  |
| 8/9 | iv infusion × 2 | non-neuronal |
|  | im × 2 |  |
| 8/10 | im × 4 | non-neuronal |
| 8/11 | im × 4 | non-neuronal |
| 8/12 | iv infusion | neuronal |
|  | im × 2 |  |

EXAMPLE 21

A 14 year old boy diagnosed with a case of DMD was bedridden with no power in both hands and legs and with muscular atrophy. He also had scoliosis.

After 8 months of therapy he has developed muscles in the biceps, triceps and brachio-radials and is able to lift his arms up to the elbow level. He has put on weight and is growing taller without any associated spinal scoliosis. His CPK levels, which indicate the rate of muscle breakdown, have been reduced.

The schedule of injections for this patient is shown in Table 20.

TABLE 20

| Date | Route of administration | Cell types |
|---|---|---|
| 4/13 | im | non neuronal (test dose) |
| 4/14 | im | non neuronal |
| 4/15 | im | neuronal |
| 4/16 | im | neuronal |
| 4/17 | im | neuronal |
|  |  | non neuronal |
| 4/18 | im | non neuronal |
| 4/19 | im | neuronal |
|  |  | non neuronal |
| 4/20 | im | neuronal |
|  |  | non neuronal |
| 4/21 | im | neuronal |
|  |  | non neuronal |
| 4/22 | im | neuronal |
|  |  | non neuronal |
| 4/23 | im | neuronal |
|  |  | non neuronal |
| 4/24 | im | neuronal |
|  |  | non neuronal |
| 4/25 | im | neuronal |
|  |  | non neuronal |
| 4/26 | im | non neuronal |
| 4/27 | im | non neuronal |
| 4/28 | im | neuronal |
|  |  | non neuronal |
| 4/29 | im | neuronal |
|  |  | non neuronal |
| 4/30 | im | neuronal |
|  |  | non neuronal |
| 5/1 | im | non neuronal |
| 5/2 | im | non neuronal |
| 5/3 | im | neuronal |
|  |  | non neuronal |
| 5/4 | im | non neuronal |
| 5/5 | im | neuronal |
|  |  | non neuronal |
| 5/6 | im | non neuronal |
| 5/7 | im | neuronal |
|  |  | non neuronal |
| 5/8 | im | neuronal |
|  |  | non neuronal |
| 5/9 | iv infusion im | neuronal |
| 5/13 | im | neuronal |
|  |  | non neuronal |
| 5/15 | im | non neuronal |
| 5/16 | im | non neuronal |
| 5/17 | im | neuronal |
|  |  | non neuronal |
| 5/18 | im | neuronal |
|  |  | non neuronal |
| 5/19 | im | neuronal |
|  |  | non neuronal |
| 5/20 | im | neuronal |
|  |  | non neuronal |
| 5/21 | im | neuronal |
|  |  | non neuronal |
| 5/22 | im | neuronal |
|  |  | non neuronal |
| 5/23 | im | neuronal |
|  |  | non neuronal |
| 5/24 | im | neuronal |
|  |  | non neuronal |
| 5/26 | im | neuronal |
|  |  | non neuronal |
| 5/27 | im | neuronal |
|  |  | non neuronal |
| 5/28 | im | neuronal |
|  |  | non neuronal |
| 5/29 | im | neuronal |
|  |  | non neuronal |
| 5/30 | im | neuronal |
|  |  | non neuronal |
| 6/1 | im | neuronal |
|  |  | non neuronal |
| 6/2 | im | neuronal |
|  |  | non neuronal |
| 6/3 | im | neuronal |
|  |  | non neuronal |
| 6/4 | im | neuronal |
|  |  | non neuronal |
| 6/5 | im | neuronal |
|  |  | non neuronal |
| 6/6 | im | neuronal |
|  |  | non neuronal |
| 6/7 | im | neuronal |
|  |  | non neuronal |
| 6/8 | im | neuronal |
|  |  | non neuronal |
| 6/9 | im | neuronal |
|  |  | non neuronal |
| 6/10 | im | neuronal |
|  |  | non neuronal |
| 6/11 | im | neuronal |
|  |  | non neuronal |
| 6/12 | im | non neuronal |
| 6/13 | im | neuronal |
|  |  | non neuronal |
| 6/14 | im | neuronal |
|  |  | non neuronal |
| 6/15 | im | neuronal |
|  |  | non neuronal |
| 6/16 | im | neuronal |
|  |  | non neuronal |
| 6/17 | im | neuronal |
|  |  | non neuronal |
| 6/18 | im | neuronal |
|  |  | non neuronal |
| 6/19 | im | neuronal × 2 |
| 6/20 | im | neuronal |
|  |  | non neuronal |
| 6/22 | im | neuronal × 2 |
| 6/23 | iv | non neuronal × 2 |
| 6/24 | iv | non neuronal × 2 |
| 6/25 | iv | non neuronal × 2 |
| 6/27 | im | neuronal |
|  |  | non neuronal |
| 6/28 | im | neuronal |
|  |  | non neuronal |
| 6/29 | im | neuronal |
|  |  | non neuronal |
| 6/30 | im | neuronal |
|  |  | non neuronal |
| 7/1 | im | neuronal |
|  |  | non neuronal |
| 7/2 | im | neuronal |
|  |  | non neuronal |
| 7/3 | im | neuronal |
|  |  | non neuronal |
| 7/4 | im | neuronal |
|  |  | non neuronal |
| 7/5 | im | neuronal × 2 |
| 7/6 | im | neuronal × 2 |
| 7/7 | im | neuronal × 2 |
| 7/8 | im | neuronal |
|  |  | non neuronal |
| 7/9 | im | neuronal |
|  |  | non neuronal |
| 7/10 | im | neuronal |
|  |  | non neuronal |

TABLE 20-continued

| Date | Route of administration | Cell types |
|---|---|---|
| 7/11 | im | neuronal |
|  |  | non neuronal |
| 7/12 | im | neuronal |
|  |  | non neuronal |
| 7/13 | im | neuronal |
|  |  | non neuronal |
| 7/14 | im | neuronal |
|  |  | non neuronal |
| 7/15 | im | neuronal |
|  |  | non neuronal |
| 8/18 | im | non neuronal × 3 |
| 8/19 | im | non neuronal × 2 |
| 8/20 | im | non neuronal × 3 |
| 8/21 | im | non neuronal × 3 |
| 8/22 | im | non neuronal × 3 |
| 8/23 | im | non neuronal × 3 |
| 8/24 | im | non neuronal × 3 |
| 8/25 | im | neuronal |
|  |  | non neuronal × 2 |
| 8/26 | im | neuronal × 3 |
| 8/27 | im | non neuronal × 3 |
| 8/28 | iv | non neuronal 7 |
| 8/29 | iv | non neuronal 7 × 2 |
| 8/30 | im | non neuronal × 2 |
| 8/31 | im | non neuronal × 3 |
| 9/1 | iv infusion | non neuronal |
| 9/2 | iv infusion | non neuronal |
| 9/3 | im | non neuronal × 3 |
| 9/4 | im | non neuronal × 3 |
| 9/5 | im | non neuronal × 3 |
| 9/6 | im | non neuronal × 3 |
| 9/7 | im | non neuronal × 3 |
| 9/8 | im | non neuronal × 3 |
| 9/9 | im | non neuronal × 3 |
| 9/10 | im | non neuronal × 3 |
| 9/11 | im | non neuronal × 3 |
| 9/12 | im | non neuronal × 3 |
| 9/13 | im | non neuronal × 3 |
| 9/14 | im | non neuronal × 3 |
| 9/15 | im | non neuronal × 3 |
| 9/16 | im | non neuronal × 3 |
| 9/17 | im | non neuronal × 3 |
| 9/18 | im | non neuronal × 3 |
| 9/19 | im | non neuronal × 3 |
| 9/20 | im | non neuronal × 3 |
| 9/21 | im | non neuronal × 3 |
| 9/22 | iv infusion | non neuronal |
| 9/23 | iv infusion | non neuronal |
| 9/24 | im | non neuronal × 3 |
| 9/25 | im | non neuronal × 3 |
| 9/26 | im | non neuronal × 3 |
| 9/27 | im | non neuronal × 3 |
| 9/28 | im | non neuronal × 3 |
| 9/29 | im | non neuronal × 3 |
| 9/30 | im | non neuronal × 3 |
| 10/1 | im | non neuronal × 3 |
| 10/2 | im | non neuronal × 3 |
| 10/3 | im | non neuronal × 3 |
| 10/4 | im | non neuronal × 3 |
| 10/5 | im | non neuronal × 3 |
| 10/6 | im | non neuronal × 3 |
| 10/7 | im | non neuronal × 3 |
| 10/8 | im | non neuronal × 3 |
| 10/9 | im | non neuronal × 3 |
| 10/11 | im | non neuronal × 3 |
| 10/12 | im | non neuronal × 3 |
| 10/13 | im | non neuronal × 3 |
| 10/14 | im | non neuronal × 3 |
| 10/15 | im | non neuronal × 3 |
| 10/16 | im | non neuronal × 3 |
| 10/17 | im | non neuronal × 3 |
| 10/18 | im | non neuronal × 3 |
| 10/19 | im | non neuronal × 3 |
| 10/20 | im | non neuronal × 3 |
| 10/21 | im | non neuronal × 3 |
| 10/23 | im | non neuronal × 3 |
| 10/24 | im | non neuronal × 3 |
| 10/25 | im | non neuronal × 3 |
| 10/26 | im | non neuronal × 3 |
| 10/27 | im | non neuronal × 3 |
| 10/28 | im | non neuronal × 3 |
| 10/29 | im | non neuronal × 3 |
| 10/30 | im | non neuronal × 3 |
| 10/31 | im | non neuronal × 5 |
| 11/2 | im | non neuronal × 4 |
| 11/3 | im | non neuronal × 3 |
| 11/4 | im | non neuronal × 3 |
| 11/5 | im | non neuronal × 3 |
| 11/7 | im | non neuronal × 3 |
| 11/8 | im | non neuronal × 2 |
| 11/9 | im | non neuronal |
| 11/10 | im | non neuronal × 3 |
| 11/11 | im | non neuronal × 3 |
| 11/12 | im | non neuronal × 3 |
| 11/13 | im | non neuronal × 3 |
| 11/14 | im | non neuronal × 3 |
| 11/15 | im | non neuronal × 3 |
| 11/30 | im | mixed × 3 |
| 12/1 | im | non neuronal × 3 |
| 12/2 | im | non neuronal × 3 |
| 12/3 | im | non neuronal × 3 |
| 12/4 | im | non neuronal × 3 |
| 12/5 | im | non neuronal × 3 |
| 12/6 | im | non neuronal × 3 |
| 12/7 | im | non neuronal × 3 |
| 12/8 | im | non neuronal × 3 |
| 12/9 | im | non neuronal × 3 |
| 12/10 | im | non neuronal × 3 |
| 12/12 | im | non neuronal × 3 |
| 12/13 | im | non neuronal × 3 |
| 12/14 | im | non neuronal × 3 |
| 12/15 | im | non neuronal × 3 |
| 12/16 | iv infusion | non neuronal |
| 12/17 | iv infusion im | non neuronal × 3 |
| 12/18 | im | non neuronal |
| 12/19 | iv im | non neuronal |
| 12/20 | im | non neuronal × 3 |
| 12/21 | iv im | non neuronal × 3 |
| 12/22 | iv | non neuronal × 3 |
| 12/23 | im | non neuronal × 3 |
| 12/24 | im | non neuronal × 3 |
| 12/25 | im | mixed × 3 |
| 12/26 | iv im | non neuronal × 3 |
| 12/27 | iv | mixed |
| 12/28 | im | non neuronal × 3 |
| 12/29 | im | non neuronal × 3 |
| 12/30 | im | non neuronal |
| 12/31 | im | non neuronal × 3 |
| 1/1 | im | mixed × 3 |
| 1/2 | im | mixed × 3 |
| 1/3 | im | non neuronal × 3 |
| 1/4 | im | non neuronal × 3 |
| 1/5 | iv infusion | non neuronal |
| 1/6 | iv infusion | non neuronal |
| 1/7 | im | non neuronal × 3 |
| 1/8 | im | non neuronal × 3 |
| 1/9 | im | non neuronal × 3 |
| 1/10 | im | non neuronal × 3 |
| 1/11 | im | non neuronal × 3 |
| 1/12 | im | non neuronal × 3 |
| 1/13 | im | non neuronal × 3 |
| 1/14 | im | non neuronal × 3 |
| 1/15 | im | non neuronal × 3 |
| 1/16 | iv infusion | mixed |
| 1/17 | iv infusion | mixed |
| 1/18 | im | non neuronal |
| 1/19 | im | non neuronal |
| 1/20 | im | non neuronal |
| 1/21 | iv infusion | mixed |
| 1/22 | im | mixed |

TABLE 20-continued

| Date | Route of administration | Cell types |
|---|---|---|
| 1/23 | im | mixed |
| 1/24 | im | neuronal |
| 1/25 | im | neuronal |
| 1/26 | im | mixed |
| 1/27 | im | mixed |
| 1/28 | im | neuronal × 3 |
| 1/29 | iv infusion | mixed |
| 1/30 | iv infusion | non neuronal |

EXAMPLE 22

An 8 year old boy wheelchair bound due to DMD was not able to walk or stand. After 6 months of treatment his CPK level was reduced. He has not deteriorated and is able to move his arms. He has started walking with minimal support.

The schedule of injections for this patient is shown in Table 21.

TABLE 21

| Date | Route of administration | Cell types |
|---|---|---|
| 4/29 | im | neuronal |
|  |  | non neuronal |
| 4/30 | im | non neuronal |
| 5/1 | im | neuronal |
|  |  | non neuronal |
| 5/3 | im | neuronal |
| 5/4 | im | neuronal |
|  |  | non neuronal |
| 5/5 | im | neuronal |
|  |  | non neuronal |
| 5/6 | im | neuronal |
|  |  | non neuronal |
| 5/7 | im | non neuronal |
| 5/8 | im | neuronal |
|  |  | non neuronal |
| 5/9 | im | neuronal |
|  |  | non neuronal |
| 5/10 | im | neuronal |
|  |  | non neuronal |
| 5/11 | im | neuronal |
|  |  | non neuronal |
| 5/12 | im | neuronal |
|  |  | non neuronal |
| 5/13 | im | neuronal |
|  |  | non neuronal |
| 5/14 | im | neuronal |
|  |  | non neuronal |
| 5/15 | im | neuronal |
|  |  | non neuronal |
| 5/16 | im | neuronal |
|  |  | non neuronal |
| 5/17 | im | neuronal |
|  |  | non neuronal |
| 5/18 | im | neuronal |
|  |  | non neuronal |
| 5/19 | im | neuronal |
|  |  | non neuronal |
| 5/20 | im | neuronal |
|  |  | non neuronal |
| 5/21 | im | neuronal |
|  |  | non neuronal |
| 5/22 | im | neuronal |
|  |  | non neuronal |
| 5/23 | im | neuronal |
|  |  | non neuronal |
| 5/24 | im | neuronal |
|  |  | non neuronal |
| 5/25 | im | neuronal |
|  |  | non neuronal |

TABLE 21-continued

| Date | Route of administration | Cell types |
|---|---|---|
| 5/26 | im | neuronal |
|  |  | non neuronal |
| 5/27 | im | neuronal |
|  |  | non neuronal |
| 5/28 | im | neuronal |
|  |  | non neuronal |
| 5/29 | im | neuronal |
|  |  | non neuronal |
| 5/30 | im | neuronal |
|  |  | non neuronal |
| 6/1 | im | neuronal |
|  |  | non neuronal |
| 6/2 | im | neuronal |
|  |  | non neuronal |
| 6/3 | im | neuronal |
|  |  | non neuronal |
| 6/4 | im | neuronal |
|  |  | non neuronal |
| 6/5 | im | neuronal |
|  |  | non neuronal |
| 6/6 | im | neuronal |
|  |  | non neuronal |
| 6/7 | im | neuronal |
|  |  | non neuronal |
| 6/8 | im | neuronal |
|  |  | non neuronal |
| 6/9 | im | neuronal |
|  |  | non neuronal |
| 11/15 | im | non neuronal |
| 11/16 | intravenous infusion | neuronal |
| 11/17 | intravenous infusion | neuronal |
| 11/18 | im | non neuronal |
| 11/19 | im | non neuronal |
| 11/20 | im | non neuronal |
| 11/21 | intravenous infusion | mixed |
| 11/22 | intravenous infusion | mixed |
| 11/23 | im | non neuronal |
| 11/25 | im | mixed |
| 11/26 | im | mixed |
| 11/27 | im | mixed |
| 11/29 | im | non neuronal |
| 12/1 | im | non neuronal |
| 12/2 | im | non neuronal |
| 12/3 | im | non neuronal |
| 12/5 | im | non neuronal |
| 12/6 | im | non neuronal |
| 12/7 | im | non neuronal |
| 12/8 | intravenous infusion | mixed |
| 12/9 | intravenous infusion | non neuronal |
| 12/10 | im | non neuronal |
| 12/11 | im | non neuronal |
| 12/12 | im | non neuronal |
| 12/15 | im | non neuronal |
| 12/16 | intravenous infusion | non neuronal |
| 12/17 | intravenous infusion | non neuronal |
| 12/18 | im | non neuronal |
| 12/19 | im iv | non neuronal |
| 12/20 | im | non neuronal |
| 12/21 | im | non neuronal |
| 12/22 | im | non neuronal |
| 12/23 | im | non neuronal |
| 12/24 | im | non neuronal |
| 12/25 | im | neuronal |
| 12/26 | im | neuronal |
| 12/27 | iv | mixed |
| 12/28 | im | neuronal |
| 12/29 | im | neuronal |
| 12/30 | im | neuronal |
| 12/31 | im | neuronal |
| 1/1 | im | neuronal |
| 1/2 | im | mixed |

TABLE 21-continued

| Date | Route of administration | Cell types |
|---|---|---|
| 1/4 | im | non neuronal |
| 1/5 | iv | non neuronal |
| 1/6 | intravenous infusion | non neuronal |
| 1/7 | im | non neuronal |
| 1/8 | im | non neuronal |

EXAMPLE 23

A 10 year old boy diagnosed with DMD who was able to take a few steps with support was brought for therapy. He was not able to turn on his own on the bed or sit on his own. He could lift his arms up to 30° till elbow level. Following a few months of treatment, his CPK level has started falling and he is able to turn on his own and can lift a mug of water above his head to bathe. He has not lost weight.

The schedule of injections for this patient is shown in Table 22.

TABLE 22

| Date | Route of administration | Cell types |
|---|---|---|
| 1/20 | im | non neuronal (test dose) |
| 1/23 | im | non neuronal |
| 1/24 | im | non neuronal |
|  | iv |  |
| 1/25 | im | non neuronal |
| 1/26 | im | neuronal |
|  |  | non neuronal |
| 1/27 | im | non neuronal |
| 2/1 | im | non neuronal |
| 2/2 | im | neuronal |
|  |  | non neuronal |
| 2/3 | im | non neuronal |
| 2/4 | im | neuronal |
|  |  | non neuronal |
| 2/5 | im | neuronal |
| 2/6 | im | non neuronal |
| 2/7 | im | non neuronal |
| 2/8 | im | neuronal |
|  |  | non neuronal |
| 2/10 | im | neuronal |
|  |  | non neuronal |
| 2/11 | im | neuronal |
|  |  | non neuronal |
| 2/12 | im | neuronal |
|  |  | non neuronal |
| 2/14 | im | neuronal |
|  | iv | non neuronal |
| 2/15 | im | neuronal |
|  |  | non neuronal |
| 2/16 | im | neuronal |
|  |  | non neuronal |
| 2/17 | im | neuronal |
|  |  | non neuronal |
| 2/18 | im | neuronal |
|  |  | non neuronal |
| 2/21 | im | neuronal |
|  |  | non neuronal |
| 2/22 | im | neuronal |
|  |  | non neuronal |
| 2/23 | im | neuronal |
|  |  | non neuronal |
| 2/24 | im | non neuronal |
| 2/25 | im | neuronal |
| 2/26 | im | neuronal |
|  |  | non neuronal |
| 2/27 | im | neuronal |
|  |  | non neuronal |
| 2/28 | im | neuronal |
|  |  | non neuronal |
| 3/28 | im | neuronal |
|  |  | non neuronal |
| 3/29 | im | neuronal |
| 3/30 | im | neuronal |
|  |  | non neuronal |
| 4/4 | im | neuronal |
| 4/5 | im | neuronal |
|  |  | non neuronal |
| 4/6 | im | neuronal |
|  |  | non neuronal |
| 4/7 | im | neuronal |
|  |  | non neuronal |
| 4/8 | im | neuronal |
|  |  | non neuronal |
| 4/9 | im | neuronal |
|  |  | non neuronal |
| 5/16 | im | neuronal |
|  |  | non neuronal |
| 5/17 | im | neuronal |
|  |  | non neuronal |
| 5/18 | im | neuronal |
|  |  | non neuronal |
| 5/19 | iv infusion | non neuronal |
| 5/20 | iv infusion | non neuronal |
| 5/21 | im | neuronal |
|  |  | non neuronal |
| 5/22 | im | neuronal |
|  |  | non neuronal |
| 5/23 | im | neuronal |
|  |  | non neuronal |
| 7/27 | iv infusion | neuronal |
| 7/28 | iv infusion | neuronal |
|  | im | non neuronal |
| 7/29 | im | neuronal |
|  |  | non neuronal |
| 7/30 | im | neuronal |
|  |  | non neuronal |
| 7/31 | im | non neuronal |
| 8/1 | im | non neuronal |
| 8/24 | im | neuronal |
|  |  | non neuronal |
| 8/25 | im | neuronal |
|  |  | non neuronal |
| 8/26 | iv infusion m | non neuronal |
| 8/27 | iv infusion | non neuronal |
|  | im |  |
| 8/28 | iv | neuronal |
|  |  | non neuronal |
| 8/29 | iv infusion | non neuronal |
|  | im |  |
| 8/30 | im | non neuronal |
| 8/31 | im | non neuronal |
| 9/1 | im | non neuronal |
| 9/2 | iv infusion | non neuronal |
|  | im |  |
| 9/3 | iv infusion | non neuronal |
|  | im |  |
| 9/4 | im | non neuronal |
| 9/5 | im | non neuronal |
| 11/17 | iv | mixed |
|  | im | non neuronal |
| 11/18 | iv infusion | neuronal |
|  | im | non neuronal |
| 11/19 | iv infusion | neuronal |
|  | im | non neuronal |
| 11/20 | im | non neuronal |
| 11/22 | iv infusion | neuronal |
| 11/23 | iv | mixed |
|  | im | non neuronal |
| 11/24 | iv | mixed |
|  | im | non neuronal |
| 11/25 | im | mixed |
|  | iv |  |
| 11/26 | im | mixed |
|  | iv |  |
| 11/27 | iv | non neuronal |
|  | im |  |

TABLE 22-continued

| Date | Route of administration | Cell types |
|---|---|---|
| 11/28 | iv | mixed |
| 11/29 | iv | mixed |
| 11/30 | im | mixed |
| 12/1 | iv<br>im | non neuronal |
| 12/2 | iv<br>im | non neuronal |
| 12/3 | iv<br>im | non neuronal |
| 12/4 | iv | mixed |
| 12/5 | im<br>iv | non neuronal |
| 1/2 | im | mixed |
| 1/3 | im | non neuronal |
| 1/4 | im | non neuronal |
| 1/5 | iv infusion<br>im | non neuronal |
| 1/6 | iv infusion<br>im | mixed<br>non neuronal |
| 1/7 | iv infusion | mixed |
| 1/8 | iv infusion<br>im | mixed<br>non neuronal |
| 1/9 | im | non neuronal |

Treatment of Cardiac Diseases and Disorders

Another use of hES cell transplantation according to the practice of the present invention is in the treatment of Cardiac Diseases and Disorders including but not limited to Restrictive Cardiomyopathy, Heart Failure, Sinus Bradycardia and Coronary Artery Disease. Some portion of the differentiated cells are incorporated into the patient's cardiac tissue, reproducing and repairing the damaged muscle.

While administration protocols may be varied to suit the particular patient, a typical protocol for the treatment of Cardiac Diseases and Disorders comprises intramuscular and intravenous injections every other day for 2 weeks and then every 3 days for the next 2 weeks, and intramuscular injections once a month along with intravenous infusions during months 3, 6, 10, and 12. Intracardiac injections around the damaged area may be given during bypass surgery.

EXAMPLE 23

A patient diagnosed with Sinus Corda Syndrome with Sinus Bradycardia was advised to have a pace-maker implanted. The patient was treated according to the practice of the present invention wherein the hES cells and their derivatives including hematopoietic stem cell progenitors via intravenous injection, or subcutaneous injection, or intramuscular injection or intracardiac injection or during angiography were administered in an amount of about 750,000 to about 160 million cells. The patient showed signs of improvement after undergoing the treatment with hES cells and the need for a pace-maker was eliminated.

The schedule of injections for this patient is shown in Table 22.

TABLE 22

| Date | Route of administration | Cell types |
|---|---|---|
| 7/6 | test dose | non-neuronal |
| 7/19 | im × 2 | neuronal |
| 7/21 | im × 2 | neuronal |
| 7/26 | im × 2 | neuronal |
| 8/4 | im × 2 | neuronal |
| 8/10 | im × 4 | neuronal |
| 8/26 | im × 2 | neuronal |

TABLE 22-continued

| Date | Route of administration | Cell types |
|---|---|---|
| 9/1 | im × 2 | neuronal |
| 9/8 | iv | neuronal |
| 9/15 | im | neuronal and non-neuronal mixture |
| 9/22 | iv<br>im | neuronal<br>non-neuronal |
| 9/28 | caudal | neuronal |
| 10/13 | iv × 2 | neuronal and non-neuronal mixture |
| 10/27 | im × 2 | neuronal and non-neuronal mixture<br>neuronal |
| 11/8 | im × 2 | non-neuronal |
| 3/23 | intra-articular in knee joint | neuronal |
| 4/14 | intra-articular in knee joint | neuronal |
| 5/18 | intra-articular in knee joint | neuronal |
| 6/14 | caudal | neuronal |

Treatment of Cancerous Cells and Oncogenic Tissues

Alternatively, hES cells may be administered according to the practice of the present invention to supplement conventional chemotherapy treatment of cancer patients. In conventional chemotherapy, cytotoxic agents are administered to destroy cancer cells. However, cytotoxic agents do not distinguish between normal cells and cancer cells, and may destroy the patient's non-cancer cells, including the cells of the patient's immune system. As a consequence, while undergoing chemotherapy, and for some period after the chemotherapy stops, cancer patients are susceptible to infection due to their compromised immune system. By administering hematopoietic stem cells, neuronal stem cells and hES cells to patients undergoing chemotherapy some portion of the injected cells will differentiate into a new immune system, replacing white blood cells, red blood cells, platelets and other cells destroyed by chemotherapy. Also, regeneration of aplastic bone marrow as a result of radiotherapy and chemotherapy, through regulation of the mechanics of mitosis, and restoration of normal cellular communication pathways boosts the immune system and halts further deregulated mitosis. The hES cells and/or their derivatives may be administered via intravenous or intramuscular injection or direct administration into the growth. These cells also act on the aberrant hedgehog pathway and control it so as to allow the stopping of the excessive multiplication.

EXAMPLE 24

A patient reporting with grade III adeno-carcinoma underwent chemotherapy treatment and surgery without success. Because of the onset of multiple hepatic metastases with nodular appearance and celiac and retropancreatic nodes, the patient needed supportive care.

hES cells and their derivatives according to the practice of the present invention were administered in an amount of about 750,000 to about 160 million cells to the patient which resulted in remarkable improvements including restoration of a uniformly heterogeneous liver that was formerly nodular and an increased ecogenic area in the lymph nodes.

The schedule of injections for this patient is shown in Table 23.

TABLE 23

| Date | Route of administration | Cell types |
|---|---|---|
| 3/23 | test dose | non-neuronal |
| 3/24 | im | non-neuronal |
| 3/25 | im | non-neuronal |
| 3/26 | im | non-neuronal |
| 3/27 | im | non-neuronal |
| 3/28 | iv | non-neuronal |
| 3/29 | iv | non-neuronal |
| 3/30 | iv | non-neuronal |
| 3/31 | iv | neuronal |
| 4/1 | iv | non-neuronal |
| 4/2 | im | non-neuronal |
| 4/3 | iv | non-neuronal |
| 4/4 | iv | non-neuronal |
| 4/5 | iv | neuronal |
|  | im × 2 | non-neuronal |
| 4/6 | iv | non-neuronal |
|  | im | neuronal |
| 4/7 | iv | non-neuronal |
| 4/8 | iv | non-neuronal |
| 4/9 | iv | non-neuronal |
| 4/10 | iv | non-neuronal |
| 4/11 | iv | non-neuronal |
|  | im | neuronal |
| 4/12 | iv | non-neuronal |
|  | im | neuronal |
| 4/13 | iv | neuronal |
|  | im | non-neuronal |
| 4/14 | iv | neuronal |
| 4/15 | iv | non-neuronal |
|  | im | neuronal |
| 4/16 | iv | non-neuronal |
|  | im | neuronal |
| 4/17 | iv | non-neuronal |
| 4/19 | iv | non-neuronal |
|  | im | neuronal |
| 4/20 | iv | non-neuronal |
|  | im | neuronal |
| 4/21 | iv | non-neuronal |
|  | im | neuronal |
| 4/23 | iv infusion | neuronal |
| 4/24 | iv | non-neuronal |
| 4/25 | im | non-neuronal |
| 4/26 | iv | non-neuronal |
| 4/27 | im | non-neuronal |
| 5/2 | iv | non-neuronal |
| 5/3 | iv | non-neuronal |
| 5/6 | im | neuronal |
|  | iv | non-neuronal |
| 5/7 | im | neuronal |
|  |  | non-neuronal |
| 5/8 | iv | non-neuronal |
| 5/12 | iv | non-neuronal |
| 5/16 | im | neuronal |
|  | iv | non-neuronal |
| 5/18 | iv infusion | non-neuronal |
| 5/19 | iv | non-neuronal |
| 5/20 | im | neuronal |
|  | iv | non-neuronal |
| 5/22 | iv infusion | non-neuronal |
|  | iv × 2 |  |
| 5/23 | iv infusion | non-neuronal |
|  | iv × 2 |  |

Treatment of Aphthous Ulcers/Lichen Planus

Yet another use of hES cells and/or their derivatives is in the treatment of any ulcer in the mucosal areas of the body, such as anaphthous ulcer of the mouth. The cells are administered intravenously, intramuscularly and locally. Daily injections are given intramuscularly or intravenously for the first 4 months and intravenous infusion every 15-30 days. Local application directly or via mixing with a gel is also done.

EXAMPLE 25

A 65 year old lady came with a tongue full of necrotic tissue and aphthous ulcers which were painful. She had difficulty in eating and swallowing and in speaking. On receiving hES cells she is better; finding it easier to swallow and speak and opening her mouth better. She also shows recovery with the ulcers and the necrotic tissue.

Treatment of Osteoarthritis, Arthritis, Ankylosing Joints

Yet another use of hES cells and/or their derivatives is in the treatment of Osteoarthritis, Arthritis and Ankylosing Joints. Daily intramuscular injections are given for priming× 10 days. Intra-articular injection of 750,000 to 80 million hES cells mixed with salumedrol is given and repeated 1½ to 3 months later.

Treatment of Brachial Plexus Injury

Yet another use of hES cells and/or their derivatives is in the treatment of Brachial Plexus Injuries wherein the affected arm is paralyzed. The cells are administered intramuscularly, intravenously and into the brachial plexus and repeated every 1½ months for a year or until the arm is better. Intravenous infusions are also used.

EXAMPLE 26

The patient is a 26 year old male who suffered from a Brachial Plexus Injury (Lt.) hand and had lost the function of it for the last 7-8 years. With stem cell treatment his left hand has become much better with more motor power up to the elbow and wrists. He is able to move his wrist and the hand is not as flaccid as before. He is also able to move his arm upwards.

Treatment of Reproductive Disorders

Another use of hES cell transplantation according to the practice of the present invention is the treatment of Reproductive Disorders, through the restoration of fertility of patients suffering from testicular atrophy, ovarian failure and azoospermia.

EXAMPLE 27

Treatment of an azoospermatic patient with hES cells and their derivatives including hematopoietic stem cell progenitors via local intramuscular injection according to the practice of the present invention resulted in the production of spermatozoa. Also, intravenous and intramuscular injections were used as well as direct injections into the testes and also subcutaneous injection near the epididymis were used.

The schedule of injections for this patient is shown in Table 24.

TABLE 24

| Date | Route of administration | Cell types |
|---|---|---|
| 2/1 | test dose | non-neuronal |
| 8/4 | im | non-neuronal |
| 2/5 | im | non-neuronal |
| 8/7 | im | non-neuronal |
| 2/2 | im | neuronal and non-neuronal mixture |
| 7/27 | im | neuronal |
| 3/6 | im | non-neuronal |
| 9/1 | im | neuronal |
| 9/2 | im | neuronal |
| 9/6 | im | neuronal |
| 9/7 | im | neuronal |
| 9/12 | im | neuronal |
| 9/13 | im | neuronal and non-neuronal mixture |
| 1/17 | iv | non-neuronal |

TABLE 24-continued

| Date | Route of administration | Cell types |
|---|---|---|
| 3/27 | im | non-neuronal |
| 4/26 | im | neuronal |
| 5/8 | im | non-neuronal |
| 5/25 | im | non-neuronal |
| 8/11 | im | non-neuronal |
| 8/17 | im | non-neuronal |
| 9/7 | im | non-neuronal |

Tissue Regeneration hES cells may be administered according to the practice of the present invention for the induction of tissue regeneration, including but not limited to muscle regeneration, the treatment of liver cirrhosis, and in the formation of new blood vessels (neo-vascularisation) which is effective in the treatment of degenerative diseases and in treating non healing ulcers.

Treatment of Diabetes

Another embodiment for the invention is the use of hES cells and/or their derivatives, wherein said cells comprise insulin producing progenitor cells, in the treatment of Diabetes. Diabetic patients are at four times higher risk of suffering a heart attack or stroke and also have an increased risk of multi organ degeneration and failure, including the kidneys, eyes, nervous system and general immunity. By treatment of diabetes through the transplantation of insulin producing hES cells, and restoration of insulin production in the body, there is a reduction in the need for insulin and a reduction in the debilitating side effects.

While administration protocols may be varied to suit the particular patient, a typical protocol for the treatment of Diabetes comprises intramuscular and intravenous injections twice a week during the first month and injections once a week during months 3, 6, 11, and 12. Intravenous infusions may also be given during month 6.

EXAMPLE 28

The patient is a 70 year old man with diabetes and who had suffered hyperketoacidosis and was on 52 units of insulin and an oral hypoglycemic. Within 6 months of therapy he was off all medications and insulin and is now currently able to maintain his blood sugar on a normal diet for the past 1½ years. He receives booster shots.

The schedule of injections for this patient is shown in Table 25.

TABLE 25

| Date | Route of administration | Cell types |
|---|---|---|
| 9/5 | test dose | non-neuronal |
| 9/6 | im | neuronal |
| 9/7 | im | neuronal |
| 9/8 | im | non-neuronal |
| 9/9 | im | non-neuronal |
| 9/12 | iv | neuronal |
| 9/13 | im | non-neuronal |
| 9/19 | im | neuronal and non-neuronal mixture |
| 9/22 | iv | non-neuronal |
| 9/26 | im | neuronal and non-neuronal mixture |
| 9/29 | im | neuronal and non-neuronal mixture |
| 10/3 | im | neuronal and non-neuronal mixture |
| 10/5 | im | non-neuronal |
| 10/10 | im | non-neuronal |
| 10/13 | iv | non-neuronal |
| 10/17 | im | neuronal and non-neuronal mixture |
| 10/20 | iv | non-neuronal |

TABLE 25-continued

| Date | Route of administration | Cell types |
|---|---|---|
| 10/24 | iv | neuronal and non-neuronal mixture |
| 10/31 | iv | neuronal and non-neuronal mixture |
| 11/3 | iv | neuronal and non-neuronal mixture |
| 11/7 | im | non-neuronal |
| 11/10 | im | non-neuronal |
| 11/14 | iv | neuronal |
| 11/17 | im | non-neuronal |
| 11/21 | im | non-neuronal |
| 12/12 | iv | non-neuronal |
| 12/19 | iv | neuronal |
| 12/26 | iv | non-neuronal |
| 1/4 | im | non-neuronal |
| 8/18 | im | non-neuronal |
| 8/21 | im | non-neuronal |
| 8/22 | im | non-neuronal |
| 8/24 | im | non-neuronal |
| 8/26 | im | non-neuronal |

EXAMPLE 29

A 54 year old man presented with uncontrolled diabetes mellitus for the past three years and was taking insulin 42 units along with an oral hypoglycemic. His fasting blood sugar was 200 mg/dl and his post prandial sugar was 280 mg/dl with all the medications.

After taking hES cells for three weeks he has stopped taking insulin and is on a reduced dose of hypoglycemic drugs. He is feeling much better and is more alert.

The schedule of injections for this patient is shown in Table 26.

TABLE 26

| Date | Route of administration | Cell types |
|---|---|---|
| 1/18 | im | neuronal (test dose) |
| 1/19 | im | non neuronal |
| 1/20 | im | non neuronal |
| 1/21 | im | mixed |
| 1/22 | im | mixed |
| 1/23 | im | mixed |
| 1/24 | im | neuronal |
| 1/25 | im | neuronal |
| 1/26 | im | non neuronal |
| 1/27 | im | non neuronal |
| 1/28 | im | neuronal |
| 1/29 | im | neuronal |
| 1/30 | im | neuronal |
| 1/31 | im | mixed |

EXAMPLE 30

A 45 year old man had angina and was diabetic. He was on insulin and an oral hypoglycemic and had undergone angioplasty.

Three months later after receiving hES cell treatment he has stopped insulin and is on a reduced dose of oral hypoglycemic. His records of blood sugar and medication are showing well controlled blood sugar levels.

The schedule of injections for this patient is shown in Table 27.

TABLE 27

| Date | Route of administration | Cell types |
|---|---|---|
| 8/21 | im | non neuronal (test dose) |
| 8/22 | im | non neuronal |
| 8/23 | im | non neuronal |
| 8/24 | im | non neuronal |
| 8/25 | im | non neuronal |
| 8/28 | im | non neuronal |
| 8/30 | im | non neuronal |
| 9/1 | im | non neuronal |
| 9/4 | im | non neuronal |
| 9/6 | iv | non neuronal |
| 9/8 | im | non neuronal |
| 9/11 | im | non neuronal |
| 9/13 | im | non neuronal |
| 9/18 | im | non neuronal |
| 9/20 | im | non neuronal |
| 9/25 | im | non neuronal |
| 9/28 | im | non neuronal |
| 9/29 | im | non neuronal |
| 9/30 | im | non neuronal |
| 10/9 | im | non neuronal |
| 10/11 | im | non neuronal |
| 10/18 | im | non neuronal |
| 10/23 | im | non neuronal |
| 10/25 | im | non neuronal |
| 10/31 | im | non neuronal |
| 11/2 | im | non neuronal |
| 11/08 | im | non neuronal |
| 11/11 | iv infusion | mixed |
| 11/12 | iv infusion | mixed |
| 11/13 | im | non neuronal |
| 11/15 | im | non neuronal |
| 11/17 | im | non neuronal |
| 11/18 | iv infusion | neuronal |
| 11/19 | iv infusion | neuronal |
| 11/20 | im | non neuronal |
| 11/22 | im | non neuronal |
| 11/25 | iv infusion | neuronal |
| 11/26 | iv infusion | neuronal |
| 11/27 | im | non neuronal |
| 11/29 | iv | neuronal |
|  | im | non neuronal |
| 11/30 | iv infusion | neuronal |
| 12/1 | iv infusion | neuronal |
| 12/10 | iv infusion | mixed |
| 12/11 | im | non neuronal |
| 12/13 | im | non neuronal |
| 12/16 | iv infusion | neuronal |
| 12/17 | iv infusion | neuronal |
| 12/18 | im | non neuronal |
| 12/20 | im | neuronal |
| 12/21 | im | neuronal |
| 12/22 | iv | neuronal |
| 1/5 | im | non neuronal |
| 1/6 | im | non neuronal |
|  | iv |  |
| 1/8 | im | non neuronal |

Treatment of Interstitial Lung Disease

EXAMPLE 31

A middle aged lady came to the clinic suffering from ILD (interstitial lung disease). She was in a terminal stage with $SPO_2$ 69% at rest. As of now with hES cell treatment her disease has stopped progressing. The patient is feeling much better overall and even her breathing has improved. The treatment is continuing. There are breath sounds that can be heard on auscultation and her overall pulmonary function tests show some improvement.

The schedule of injections for this patient is shown in Table 28.

TABLE 28

| Date | Route of administration | Cell types |
|---|---|---|
| 10/16 | im | non neuronal (test dose) |
| 10/17 | im | non neuronal |
| 10/18 | im | non neuronal |
| 10/19 | iv | neuronal |
|  | epidural | non neuronal |
|  | nebulisation |  |
| 10/20 | iv | neuronal |
|  | nebulisation |  |
| 10/21 | iv | neuronal |
|  | nebulisation |  |
| 10/22 | im | neuronal |
|  | iv | non neuronal |
|  | nebulisation |  |
| 10/23 | iv | neuronal |
|  | nebulisation |  |
| 10/24 | im | non neuronal |
|  | nebulisation |  |
| 10/25 | im | mixed |
|  | iv |  |
|  | nebulisation |  |
| 10/26 | iv | mixed |
|  | nebulisation |  |
| 10/27 | iv | mixed |
|  | nebulisation |  |
| 10/28 | iv | neuronal |
|  | nebulisation |  |
| 10/29 | iv | neuronal |
|  | nebulisation |  |
| 10/30 | iv | mixed |
|  | nebulisation |  |
| 10/31 | iv | mixed |
|  | nebulisation |  |
| 11/2 | iv | mixed |
|  | nebulisation |  |
| 11/3 | iv | mixed |
|  | nebulisation |  |
| 11/4 | iv | mixed |
|  | nebulisation |  |
| 11/5 | iv | mixed |
|  | nebulisation |  |
| 11/6 | iv | mixed |
|  | nebulisation |  |
| 11/7 | iv | mixed |
|  | nebulisation |  |
| 11/8 | iv | non neuronal |
|  | nebulisation |  |
| 11/9 | iv | mixed |
|  | nebulisation |  |
| 11/10 | iv | non neuronal |
|  | nebulisation |  |
| 11/11 | iv | mixed |
|  | nebulisation |  |
| 11/12 | iv | mixed |
|  | nebulisation |  |
| 11/13 | iv | mixed |
|  | nebulisation |  |
| 11/14 | iv | mixed |
|  | nebulisation |  |
| 11/15 | iv | neuronal |
|  | nebulisation |  |
| 11/16 | im | neuronal |
|  | iv | non neuronal |
|  | nebulisation |  |
| 11/17 | im | non neuronal |
|  | iv |  |
|  | nebulisation |  |
| 11/18 | im | non neuronal |
|  | iv |  |
|  | nebulisation |  |
| 11/19 | im | non neuronal |
|  | iv |  |
|  | nebulisation |  |

TABLE 28-continued

| Date | Route of administration | Cell types |
|---|---|---|
| 11/20 | IM | non neuronal |
| | IV | |
| | Nebulisation | |
| 11/21 | im | non neuronal |
| | iv | |
| | nebulisation | |
| 11/22 | im | non neuronal |
| | iv | |
| | nebulisation | |
| 11/23 | iv | neuronal |
| | nebulisation | |
| 11/24 | iv | non neuronal |
| | nebulisation | |
| 11/25 | iv | non neuronal |
| | nebulisation | |
| 11/26 | iv | non neuronal |
| | nebulisation | |
| 11/27 | iv | non neuronal |
| | nebulisation | |
| 11/28 | im | non neuronal |
| | iv | |
| | nebulisation | |
| 11/29 | im | non neuronal |
| | iv | |
| | nebulisation | |
| 11/30 | im | non neuronal |
| | iv | |
| | nebulisation | |
| 12/1 | iv | non neuronal |
| | nebulisation | |
| 12/2 | iv | non neuronal |
| | nebulisation | |
| 12/3 | iv | non neuronal |
| | nebulisation | |
| 12/4 | iv | non neuronal |
| | nebulisation | |
| 12/5 | iv | non neuronal |
| | nebulisation | |
| 12/6 | iv | non neuronal |
| | nebulisation | |
| 12/7 | iv | non neuronal |
| | nebulisation | |
| 12/8 | iv | non neuronal |
| | nebulisation | |
| 12/9 | iv | neuronal |
| | nebulisation | |
| 12/10 | iv | neuronal |
| | nebulisation | |
| 12/11 | iv | non neuronal |
| | nebulisation | |
| 12/12 | iv | non neuronal |
| | nebulisation | |
| 12/13 | iv | non neuronal |
| | nebulisation | |
| 12/14 | iv | non neuronal |
| | nebulisation | |
| 12/15 | iv | non neuronal |
| | nebulisation | |
| 12/16 | iv | non neuronal |
| | nebulisation | |
| 12/17 | iv | non neuronal |
| | nebulisation | |
| 12/18 | iv | non neuronal |
| | Nebulisation | |
| 12/19 | IV | non neuronal |
| | nebulisation | |
| 12/20 | iv | non neuronal |
| | nebulisation | |
| 12/21 | iv | non neuronal |
| | nebulisation | |
| 12/22 | iv | neuronal |
| | nebulisation | non neuronal |
| 12/23 | im | neuronal |
| | iv | non neuronal |
| | nebulisation | |
| 12/24 | im | neuronal |
| | iv | non neuronal |
| | nebulisation | |
| 12/25 | im | mixed |
| | iv | |
| 12/26 | iv | mixed |
| | nebulisation | |
| 12/27 | iv | mixed |
| | nebulisation | |
| 12/28 | iv | mixed |
| | nebulisation | |
| 12/29 | im | neuronal |
| | iv | mixed |
| 12/30 | im | neuronal |
| | iv | |
| | nebulisation | |
| 12/31 | im | neuronal |
| | iv | mixed |
| | nebulisation | |
| 1/1 | im | mixed |
| | iv | |
| | nebulisation | |
| 1/2 | im | mixed |
| | iv | |
| | nebulisation | |
| 1/3 | im | non neuronal |
| | iv | |
| | nebulisation | |
| 1/4 | im | non neuronal |
| | iv | |
| | nebulisation | |
| 1/5 | im | neuronal |
| | iv | non neuronal |
| | nebulisation | |
| 1/6 | im | mixed |
| | iv | non neuronal |
| | nebulisation | |
| 1/7 | im | mixed |
| | iv | non neuronal |
| | nebulisation | |
| 1/8 | im | mixed |
| | iv | non neuronal |
| | nebulisation | |
| 1/9 | im | mixed |
| | iv | non neuronal |
| | nebulisation | |
| 1/10 | im | mixed |
| | iv | non neuronal |
| | nebulisation | |
| 1/11 | im | mixed |
| | iv | non neuronal |
| | nebulisation | |
| 1/12 | im | mixed |
| | iv | non neuronal |
| | nebulisation | |
| 1/13 | iv | mixed |
| 1/14 | im | mixed |
| | iv | non neuronal |
| | nebulisation | |
| 1/15 | im | neuronal |
| | iv | non neuronal |
| | nebulisation | |
| 1/16 | im | mixed |
| | iv | non neuronal |
| | nebulisation | |
| 1/17 | im | mixed |
| | iv | non neuronal |
| | Nebulisation | |
| 1/18 | IM | mixed |
| | IV | non neuronal |
| | nebulisation | |
| 1/19 | im | mixed |
| | iv | non neuronal |
| | nebulisation | |
| 1/20 | im | non neuronal |
| | iv | |
| | nebulisation | |
| 1/21 | im | mixed |
| | iv | |
| | nebulisation | |

TABLE 28-continued

| Date | Route of administration | Cell types |
|---|---|---|
| 1/22 | im | mixed |
|  | iv |  |
|  | nebulisation |  |
| 1/23 | im | neuronal |
|  | iv | mixed |
|  | nebulisation |  |
| 1/24 | im | neuronal |
|  | iv | mixed |
|  | nebulisation |  |
| 1/25 | im | neuronal |
|  | iv | mixed |
|  | nebulisation |  |
| 1/26 | im | neuronal |
|  | iv | mixed |
|  | nebulisation |  |
| 1/27 | im | neuronal |
|  | iv | mixed |
|  | nebulisation |  |
| 1/28 | im | neuronal |
|  | iv | mixed |
|  | nebulisation |  |
| 1/29 | im | neuronal |
|  | iv | mixed |
|  | nebulisation |  |
| 1/30 | im | non neuronal |
|  | iv |  |
|  | nebulisation |  |
| 1/31 | im | non neuronal |
|  | iv |  |
|  | nebulisation |  |

New Drug Development

Still another use for hES cells is for developing and testing new drugs. For example, hES cells may be cultured according to the practice of the present invention and used as a substrate for testing the targets, mode of action, uptake, metabolism, excretion, toxicity and safety of new chemical entities, drug candidates and new pharmaceuticals during pharmaceutical research and development. In one embodiment, the present invention relates to methods for testing the effect of a compound on hES cells and/or their derivatives, comprising culturing hES cells and/or their derivatives obtained by the methods of the present invention in the presence of the compound and determining the effect of the compound on the cells.

EXAMPLE 32

The effects of the antibiotics tetracycline and ceftriaxone on cultured hES cells was analyzed along with the patient's serum. These drugs were introduced separately as well as together in different concentrations and the effects studied on the stem cells. Finally the dose of the medication and the efficacy of the drugs were determined.

Drug Delivery

Another use for hES cells and/or their derivatives is to carry drugs to the site of an injury or disease for localized delivery. hES cells and/or their derivatives may be incubated in the presence of a drug so that the cells take up the drug. The loaded cells can then be delivered locally to the treatment site where the drug will diffuse out of the cells and treatment of the injury or disease will ensue. In another embodiment, the loaded cells can be delivered to a site other than the damaged or diseased area if the damaged or diseased area is unsuitable for direct application of the drug (e.g., the area is too damaged for direct injection of the drug). This method of drug delivery allows for the use of drugs that would be toxic if administered systematically to a subject. The method also allows higher concentrations of the drug to be administered to the site than may be possible by other routes of administration. In a further embodiment, hES cells and/or their derivatives can be loaded with one or more drugs that will enhance the treatment produced by the transplantation of the cells themselves. Non-limiting examples include loading cells with antihypertensive agents for treatment of cardiac disease, loading cells with chemotherapeutic agents for treatment of cancer patients, and loading cells with neurotrophic factors for treatment of SCI. In one embodiment, the present invention relates to methods for delivering a drug to a subject comprising culturing hES cells and/or their derivatives obtained by the methods of the present invention in the presence of the drug, wherein the cells take up the drug, and administering the cells to a site in the subject, wherein the drug is delivered.

In one aspect of the invention, the culture methodologies of the present invention allow the exposure of the hES cells and/or their derivatives to drugs and other active agents in vitro prior to transplantation, as compared to administering the drugs or active agents directly to patients. Exposure of the cells in vitro advantageously provides the positive effects of the drugs (e.g., the neurotrophic effects of valproic acid) while avoiding the toxicity of systemic administration of the drug.

Spinal Cord Injury Treatment: Case Studies

Clinical treatments using hES cells and their derivatives for SCI have shown remarkable results. Given the nature of the practice of the present invention, and that the patients were incurable volunteers, and that their condition was ASIA A chronic SCI, and therefore beyond the stage at which natural neural regeneration processes are possible, double-blind or placebo controlled trials have not been carried out, in respect of the Doctors oath. The results of the protocol are demonstrated through the detailed examples provided as case studies below.

Case Study 1

The practice of the present invention resulted in the reversal of the symptoms of SCI in a subject suffering from SCI by transplantation of hES cells according to the protocol described herein.

ReRo 1.3.4./000/220905/α, a 29 year old subject with a C6-C7 fracture and dislocation was declared untreatable by different medical practices. The subject had no sensation from the inter mammary area downwards, and was unable to sit on his own, had no bladder or bowel control, was not able to move his arms and fingers and had no power or tone in his legs. The subject had developed non-healing bilateral bedsores during a period of three years. Administration of hES cells and their derivatives according to the practices of the present invention was initiated under these conditions as follows.

A pharmaceutical composition containing approximately about 750,000 to about 80 million hES cells and their derivatives including hematopoietic stem cell progenitors and neuronal stem cell progenitors was diluted in sterile normal saline to a final volume of 0.25 to 1.0 ml, karyotyped, tested for contamination, viability and count using standard protocols and then administered by subcutaneous injection in the forearm. The subject was observed for anaphylactic shock, pain or inflammation at the site of the injection, generalised itching, flushing or fever after five minutes, ten minutes, fifteen minutes, thirty minutes, one hour and twenty four hours.

Treatment of the subject was by administration of a subcutaneous priming injection of a pharmaceutical composition containing 750,000 to 80 million hES cells and their derivatives, wherein said cells comprise hematopoietic stem cell progenitors and neuronal stem cell progenitors, resuspended in a volume of 0.25 ml to 1.0 ml of sterile normal saline. A further priming injection carrying the same number of hematopoietic stem cells and neuronal stem cells resuspended in 0.25 ml to 1.0 ml of sterile normal saline was administered by intramuscular injection. A final priming injection of 750,000 to 80 million neuronal stem cell progenitors resuspended in a volume of 0.25 ml to 1.0 ml of sterile normal saline was administered by intravenous injection.

Direct treatment of the SCI according to the practice of the present invention was performed by resuspension of a pharmaceutical composition comprising 750,000 to 80 million hES cells and their derivatives, wherein said cells comprise neuronal stem cell progenitors, resuspended in a volume of 2 ml of sterile normal saline and further diluted to 15 ml to 40 ml of sterile normal saline and administered by epidural injection at the site, below the site, and above the site of the lesion seven days after the first priming injection. Treatment by administration of epidural injection was repeated after one and a half months of priming, four months after priming, and six months after priming.

In addition to the epidural administration, the subject was treated by intrathecal injection of a pharmaceutical composition comprising 750,000 to 11 million hES cells and their derivatives, wherein said cells comprise hematopoietic stem cell progenitors and neuronal stem cell progenitors resuspended in 2 ml of sterile normal saline two and five months after the start of the treatment.

In addition, the subject was treated with an epidural injection of a pharmaceutical composition comprising 750,000 to 80 million hES cells and their derivatives, wherein said cells comprise neuronal stem cell progenitors, resuspended in 2 ml of sterile normal saline and further diluted to a final volume of 4 ml, twice daily for three consecutive days.

The schedule of injections for this patient is shown in Table 29.

TABLE 29

| Date | Route of administration | Cell types |
| --- | --- | --- |
| 8/24 | test dose | non-neuronal |
| 8/25 | im × 3 | hES |
| 8/27 | im × 2 | neuronal |
| 8/28 | spray for bed sore | neuronal |
| 8/29 | im × 4 | neuronal |
| 9/6 | im × 2 | neuronal |
| 9/8 | epidural | neuronal |
| 9/9 | iv | neuronal |
| 9/10 | im | non-neuronal |
| 9/14 | im | neuronal and non-neuronal mixture |
| 10/4 | im | non-neuronal |
|  | intrathecal |  |
| 10/7 | im | non-neuronal |
|  | deep spinal |  |
| 10/15 | im | neuronal |
| 10/21 | im | non-neuronal |
| 10/26 | iv | neuronal |
| 11/7 | im | non-neuronal |
| 3/1 | im | neuronal |
|  | deep spinal × 3 |  |
| 3/2 | im × 2 | neuronal |
| 3/3 | im × 2 | neuronal |
| 3/5 | im | neuronal |
| 3/6 | im × 2 | neuronal |
| 3/7 | im × 2 | neuronal |
| 3/8 | im | neuronal |
|  | epidural × 2 |  |
| 3/9 | epidural catheter | neuronal |
| 3/10 | epidural catheter | neuronal |
| 3/11 | epidural catheter | neuronal |
| 3/12 | deep spinal | neuronal |
| 3/13 | deep spinal | neuronal |
| 3/14 | im | neuronal |
| 3/15 | im | neuronal |
| 3/16 | im | neuronal |

TABLE 29-continued

| Date | Route of administration | Cell types |
| --- | --- | --- |
| 3/17 | im | neuronal |
| 3/18 | im | neuronal |
| 3/19 | im | neuronal |
| 3/20 | im | neuronal |
| 3/21 | im | neuronal |
| 3/22 | im | neuronal |
| 3/23 | im | neuronal |
| 3/24 | im | neuronal |
| 3/25 | im | neuronal |
| 3/26 | im | neuronal |
| 3/27 | im | neuronal |
| 3/28 | im | neuronal |
| 3/29 | im | neuronal |
| 3/30 | im | neuronal |
| 3/31 | im | neuronal |
| 5/1 | im | neuronal |
| 5/2 | im | neuronal |
| 5/3 | epidural catheter | neuronal |
| 5/4 | epidural catheter | neuronal |
| 5/5 | epidural catheter | neuronal |
| 5/6 | im | neuronal |
| 5/8 | im | non-neuronal |
| 5/12 | im | neuronal |

The neurological well-being of the subject was evaluated at regular intervals after the start of treatment, and a marked improvement of the mental state and general hygiene of the subject was observed after two weeks as shown in TABLE 30.

TABLE 30

| Time Period | Mental State | Hygiene | Behavior | Cranial Nerves |
| --- | --- | --- | --- | --- |
| 0 day | Depressed | Poor | Polite | Normal |
| 3 days | Depressed | Poor | Polite | Normal |
| 15 days | Hopeful | Average | Polite | Normal |
| 2 months | Happy | Average | Polite | Normal |
| 3 months | Hopeful | Average | Polite | Normal |
| 10 months | Very Happy and looks forward to life | Average | Polite | Normal |

Signs and symptoms typical of damage to the autonomous nervous system as a result of a C6-C7 fracture were evaluated during the course of the treatment. A marked and progressive improvement in all parameters tested, including the ability to sense deep pressure, sense of touch, sensation, balance, ability to sense pain, ability to sense change in temperature, involuntary movements, presence of cold sweats, giddiness, blood pressure, breathing difficulty, abnormal posture whilst lying down and ability to sit unaided, was observed as shown in TABLE 31.

TABLE 31

| Time Period | Deep Pressure | Touch | Sensation | Balance | Pain | Temp. |
|---|---|---|---|---|---|---|
| 0 days | Inter-mammary | Lower border of clavicle | Lower border of clavicle | Not sitting | Upper border of clavicle | Upper border of clavicle |
| 3 days | Umbilicus | Arm Inter-mammary | Arm Inter-mammary forearm | Not sitting | Inter-mammary | Inter-mammary |
| 15 days | Below umbilicus | Xiphi-sternum | Xiphi-sternum and inner arm | Sitting | Xiphi-sternum and inner arm | Xiphi-sternum and inner arm |
| 2 months | Ischial spine | Ischial spine | Xiphi-sternum and inner arm | Sitting very well | Ischial spine | Ischial spine |
| 3 months | Upper border of thigh | Ischial spine | Xiphi-sternum and inner arm | Sitting | Ischial spine | Ischial spine |
| 10 months | Upper border of thigh | Perineal | Umbilicus | Sitting well | Perineal | Perineal |
| 05.06 | Perineal | Half way Down thighs | Umbilicus | Sitting well | Perineal | Perineal |

| Time Period | Cold Sweats | Giddiness | BP | Respiration | Abnormal Posture While lying Down |
|---|---|---|---|---|---|
| 0 days | ++++ | ++++ | Fluctuating | Diaphragmatic breathing | Unable to sit |
| 3 days | +++ | +++ | Fluctuating | Diaphragmatic breathing | Unable to sit |
| 15 days | ++ | + | Stable | normal | Sitting stable |
| 2 months | nil | + on sitting | Stable | normal | Sitting very Well |
| 3 months | nil | + on sitting | Stable | normal | Sitting very Well |
| 10 months | nil | + on standing | Stable | normal | Standing with calipers and walking frame |
| 05.06 | nil | nil | Stable | normal | Standing with calipers and walking frame and takes a step forward |

Bladder and bowel dysfunction is commonly associated with neurological damage as a result of SCI. This damage results in impaired bladder control, bladder stream and sensation of fullness in the bladder, bowel control, time for evacuation of the bowel and sensation in the bowel. During the course of the treatment, marked and progressive improvements in all parameters tested were observed as a result of the treatment as shown in TABLE 32.

Changes in the motor function of the upper body, as evidence for neural regeneration at the site of the C6-C7 lesion were evaluated during the course of the treatment. Marked and progressive improvements in shoulder movement, wrist and finger movement, power in the fingers, tendon reflexes, strength of limb movement, muscular atrophy and hand grasp were observed as shown in TABLE 33.

TABLE 32

| Time period | Involuntary Movements | Bladder Control | Bladder Stream | Sensation (bladder) | Bowel Control | Time Of Evacuation | Sensation (bowel) |
|---|---|---|---|---|---|---|---|
| 0 day | Nil | Nil | Nil | Nil | Nil | 3 hours | Nil |
| 3 days | Nil | Nil | Nil | Nil | Nil | 3 hours | Nil |
| 15 days | Nil | Nil | Nil | Nil | Nil | 2.5 hours | Nil |
| 2 months | Nil | Nil | Nil | Nil | Nil | 2 hours | + |
| 3 months | Nil | Nil | Nil | Started | + | 0.5 hours | ++ |

TABLE 33

| Time Period | Shoulder | | Wrist Fingers | | Reflex of Tendons | | Power | | | | Atrophy | | | | Hand |
| --- | --- | --- | --- | --- | --- | --- | --- | --- | --- | --- | --- | --- | --- | --- | --- |
| | L | R | L | R | L | R | S | FA | W | F | S | FA | W | F | Grasp |
| 0 day | Shrugging + | | Wrist drop Wasted finger No movement | | Biceps Brisk Bilateral | | 4 | 2 | 3 | 0 | 0 | 3+ | 4+ | 4+ | Nil B/L |
| 3 days | Shrugging + | | Wrist drop Wasted finger No movement | | Biceps Brisk Bilateral | | 4 | 2 | 3 | 0 | 0 | 3+ | 4+ | 4+ | Nil B/L |
| 15 days | Shrugging + | | Wrist drop Better Can grasp Can move wrist | | Brisk | | 4 | 3 | 4 | 3 | 0 | 3 | 4 | 4+ | Present Can hold Glass |
| 2 months | + | | Wrist drop Better Can grasp Can move wrist | | Equivocal | | 4 | 4 | 4 | 4 | 0 | 2+ | 3+ | 3+ | Can put food in mouth |
| 3 months | + | | Movement much better | | Equivocal | | 4 | 4 | 4 | 4 | 0 | 2+ | 3+ | 3+ | |

S = Shoulder;
FA = Forearm;
W = Wrist;
F = Fingers;
L = Left;
R = Right
Power: 0 is poor, 4 is good
Atrophy: 0 is good, 4 is poor Changes in the motor function of the lower body, as evidence for neural regeneration at the site of the C6-C7 lesion, were evaluated during the course of the treatment, including hip movement, knee movement, toe movement, tendon reflexes, strength of the limb, muscular atrophy and plantar response. Although there was no improvement in any of the parameters tested during the course of the study, after three months of treatment, the subject was able to stand with the aid of a walking frame as shown in TABLE 34.

TABLE 34

| Time Period | Hip | | Knee | | Toe | | Reflex | | Power | | Atrophy | | Plantar | |
| --- | --- | --- | --- | --- | --- | --- | --- | --- | --- | --- | --- | --- | --- | --- |
| | L | R | L | R | L | R | L | R | L | R | L | R | L | R |
| 0 day | 0 | 0 | 0 | 0 | 0 | 0 | 0 | 0 | 0 | 0 | 4+ | 4+ | equivocal | equivocal |
| 3 days | 0 | 0 | 0 | 0 | 0 | 0 | 0 | 0 | 0 | 0 | 4+ | 4+ | equivocal | equivocal |
| 15 days | 0 | 0 | 0 | 0 | 0 | 0 | 0 | 0 | 0 | 0 | 4+ | 4+ | equivocal | equivocal |
| 2 months | 0 | 0 | 0 | 0 | 0 | 0 | 0 | 0 | 0 | 0 | 4+ | 4+ | equivocal | equivocal |
| 3 months | STOOD UP WITH WALKER FOR 10 MINUTES | | | | | | | | | | | | equivocal | |

Case Study 2

ReRo 1.3.4./001/051004/α001, a twenty two year old subject suffered with post traumatic paraplegia SCI as a result of a D6-D7 fracture after a fall from a second floor roof top. The subject went into a coma for two days after the fall and regained consciousness, but developed bilateral paralysis with total sensory and motor loss of the lower half of the body from the inter mammary region to the feet, and was unable to lift his feet or legs and was unable to sit unaided or get up into a sitting position. The subject was permanently bed ridden, had lost bladder and bowel control and was totally dependent upon the support of his family although his upper limbs were unaffected.

Administration of a pharmaceutical composition comprising hES cells and their derivatives according to the practice of the present invention was initiated after five months of the injury. In five months time, the subject regained bladder and bowel control, and ability to sit without support, and slide up and down by lifting the hip. Sensory perception restored to the perineal level. The subject can lift himself into a walking frame unaided, and can stand with ease in the frame without the need for knee support. The treatment resulted in the ability of the subject to walk using the walking frame with the support of a knee brace and return to work, i.e., he has regained a regular life style.

The schedule of injections for this patient is shown in Table 35.

TABLE 35

| Date | Route of administration | Cell types |
| --- | --- | --- |
| 10/5 | test dose | neuronal |
| 8/17 | im × 3 | neuronal |
| 8/18 | im | neuronal |
| 8/19 | im | neuronal |
| 9/5 | im | non-neuronal |
| 9/6 | im × 2 | neuronal |
| 9/7 | im | neuronal |
| 9/8 | im | neuronal |
| 9/10 | im | non-neuronal |
| 9/13 | im | neuronal and non-neuronal mixture |
| 9/14 | im | neuronal and non-neuronal mixture |
| 9/15 | im | non-neuronal |
| 11/6 | epidural catheter | neuronal |
| 11/7 | epidural catheter × 3 | neuronal |
| 11/8 | epidural catheter × 3 | neuronal |
| 11/9 | epidural catheter × 3 | neuronal |
| 11/10 | epidural catheter × 3 | neuronal |
| 11/11 | iv | neuronal |
| 11/12 | im | neuronal |
| 11/13 | iv | neuronal |
| 11/14 | iv | neuronal |
| 11/15 | iv | neuronal |
| 11/16 | im | non-neuronal |
| 11/18 | im | non-neuronal |
| 1/12 | im | neuronal |
| 2/14 | im | non-neuronal |
| 2/15 | im | neuronal |
| 2/16 | im | non-neuronal |
| 2/17 | im | non-neuronal |
| 2/18 | im | neuronal |
| 3/26 | im | neuronal |
| 3/27 | epidural catheter × 3 | neuronal |
| 3/28 | epidural catheter × 4 | neuronal |
| 3/29 | epidural catheter × 2 | neuronal |
| 3/30 | epidural catheter × 2 | neuronal |
| 3/31 | iv | neuronal |
| 5/21 | im | neuronal |
| 5/24 | intrathecal | neuronal |
| 5/26 | im | neuronal |
| 7/14 | im | neuronal |
| 7/15 | im | neuronal |
| 7/16 | im | neuronal |
| 7/17 | im | neuronal |
| 7/18 | intrathecal | neuronal |
| 7/19 | im | neuronal |
| 7/21 | im | neuronal |
| 7/22 | im | neuronal |
| 7/24 | caudal | neuronal |

Case Study 3

ReRo 1.3.4./002/040205/α, a forty-year-old subject suffered from quadriplegic SCI as a result of a C5-C6 injury and stiffness and pain in the neck. The subject underwent surgery after six months and was quadriplegic since then. The subject suffered from a feeling of sinking and dizziness if made to sit with support, and had sensation from the upper border of the scapula upwards, with total loss of power in all four limbs and loss of bowel and bladder function immediately after surgery.

Administration of a pharmaceutical composition comprising hES cells and their derivatives according to the practice of the present invention was initiated nine months after surgery. As a result of the hES cell treatment, the subject is able to sit comfortably without the need for support, and is able to move and bend to the side whilst sitting in a chair with his legs hanging down comfortably. The subject regained a marked improvement of his control of his upper body. The subject received substantial improvement in his general psychological well being through the increased mobility and independence and activities. He is able to stand with support with strength in lower limbs, control of toe movement, and no wrist drop. Treatment is ongoing according to the improvements of the subject's condition.

Case Study 4

ReRo 1.3.4./003/260902/β, a thirty seven year old subject who suffered spinal injury with brain damage seventeen years ago after a road traffic accident and was confined to a wheelchair. Subject also suffered with right-sided hemiplegia, inability to talk, facial paralysis, a total loss of memory and no bladder control.

The subject was administered pharmaceutical composition comprising hES cells and their derivatives according to the practice of the present invention for one year and two months which resulted in the ability to walk with the aid of a walking frame, speaking of a few words, straightened neck, removal of facial paralysis and improving of memory.

Case Study 5

ReRo 1.3.4./004/030505/α, a fifty six year old subject who suffered from post-traumatic fracture at C5-C8 with retrovulsion of the fractured vertebrae causing cord contusion and associated anterior epidural hemorrhage and was paraplegic. The subject was unable to move both lower limbs and suffered acute pain in his back.

The administration of a pharmaceutical composition comprising hES cells and their derivatives according to the practice of the present invention was carried out for a period of one year which resulted in regaining of some strength in both legs, sensory perception such as vibration in the legs, and ability to stand with the aid of a walker without back pain. The subject can walk with the aid of a walking frame, regained bladder control and sensation, and overcame bouts of cold sweats and giddiness.

The schedule of injections for this patient is shown in Table 36.

TABLE 36

| Date | Route of administration | Cell types |
| --- | --- | --- |
| 5/25 | test dose | non-neuronal |
| 5/27 | im | mixed - neuronal > hematopoietic |
| 6/3 | im | mixed - neuronal > hematopoietic |
| 6/6 | im | mixed - neuronal > hematopoietic |
| 6/20 | im | mixed - neuronal > hematopoietic |
| 6/22 | im | mixed - neuronal > hematopoietic |
| 6/24 | im | mixed - neuronal > hematopoietic |
| 6/27 | im | mixed - neuronal > hematopoietic |
| 6/29 | iv | mixed - neuronal > hematopoietic |
| 6/30 | im iv | mixed - neuronal > hematopoietic |
| 7/1 | iv | mixed - neuronal > hematopoietic |
| 7/4 | im | mixed - neuronal > hematopoietic |
| 7/5 | iv | mixed - neuronal > hematopoietic |
| 7/6 | im | mixed - neuronal > hematopoietic |
| 7/7 | iv | mixed - neuronal > hematopoietic |
| 7/11 | im | non-neuronal |
| 7/12 | im | hES |
| 7/18 | iv | neuronal |
| 7/19 | im | neuronal |
| 7/20 | im | neuronal |
| 7/21 | im × 2 | neuronal |
| 7/25 | im × 2 | neuronal |
| 7/26 | im | neuronal |
| 7/27 | im × 2 | neuronal |
| 7/28 | im | neuronal |
| 7/29 | im × 2 | neuronal |
| 7/30 | im × 2 | neuronal |
| 8/1 | im × 2 | neuronal |
| 8/2 | im × 2 | neuronal |
| 8/16 | im × 2 | neuronal |
| 8/17 | im | neuronal |
| 8/25 | im × 2 | hES |
| 8/30 | im × 2 | neuronal |

TABLE 36-continued

| Date | Route of administration | Cell types |
|---|---|---|
| 9/1 | im × 2 | neuronal |
| 9/2 | im × 2 | neuronal |
| 9/6 | intrathecal | mixed - neuronal > hematopoietic |
| 9/7 | im | neuronal |
| 9/13 | im | neuronal and non-neuronal mixture |
| 9/14 | im | neuronal and non-neuronal mixture |
| 9/15 | im | neuronal and non-neuronal mixture |
| 9/19 | im × 2 | neuronal |
| | | neuronal and non-neuronal mixture |
| 10/4 | im | neuronal |
| 10/5 | im | neuronal |
| | intrathecal | |
| 10/11 | deep spinal | neuronal |
| 10/13 | epidural | neuronal |
| 10/17 | side of the spine | neuronal |
| 11/5 | intrathecal | neuronal |
| 11/7 | im | non-neuronal |
| 11/8 | im | non-neuronal |
| 11/9 | deep spinal | neuronal |
| 11/17 | im × 2 | non-neuronal |
| | patient in hospital until January | |
| 1/12 | im | non-neuronal |
| 1/25 | im | neuronal |
| 2/8 | im | neuronal |
| 3/2 | im × 3 | neuronal (2) |
| | | non-neuronal |
| 3/8 | im | non-neuronal |
| 3/9 | im | non-neuronal |
| 3/10 | im | non-neuronal |
| 3/13 | epidural catheter × 4 | neuronal |
| 3/14 | epidural catheter × 4 | neuronal |
| 3/15 | epidural catheter × 4 | neuronal |
| 3/16 | epidural catheter × 2 | neuronal |
| 3/20 | im | neuronal |
| 3/22 | im | neuronal |
| 3/28 | im | non-neuronal |
| 3/29 | im | non-neuronal |
| 4/3 | im | non-neuronal |
| 4/4 | im | non-neuronal |
| 4/7 | im × 2 | neuronal |
| 4/14 | im | neuronal |
| 4-20 | epidural catheter × 5 | neuronal |
| 4/21 | epidural catheter × 3 | neuronal |
| 4/24 | im | neuronal |
| 5/19 | im × 2 | neuronal |
| | | non-neuronal |
| 5/25 | caudal | neuronal |
| 6/5 | iv infusion × 2 | neuronal |
| 6/6 | iv infusion × 2 | neuronal |
| 6/9 | intrathecal | neuronal |
| 6/10 | iv infusion | non-neuronal |
| 6/11 | iv infusion | non-neuronal |
| 6/12 | iv | non-neuronal |
| 6/13 | im | non-neuronal |
| 6/21 | im | neuronal |
| 7/4 | im | neuronal |
| 7/10 | intrathecal | neuronal |
| 7/11 | iv infusion × 2 | neuronal |
| 7/12 | iv infusion × 2 | neuronal |
| 7/13 | caudal | neuronal |
| 7/14 | iv | non-neuronal |

Case Study 6

ReRo 1.3.4./005/130705/β, a twenty five year old subject who was diagnosed with Potts Spine disorder at the D6 level with lower limb paraplegia, underwent surgery three times with an anterior decompression of the spinal cord. The subject was wheelchair bound, could not sit without support, with flaccid paralysis of the legs, had no bowel control and evacuated whilst lying and had no bladder sensation.

The subject was administered a pharmaceutical composition comprising hES cells and their derivatives according to the practice of the present invention, eleven years and six months after the injury. The treatment protocol followed during the first year resulted in strengthening the back, ability to sit without support, and sensation of heaviness in the legs. The subject also regained backache during menstruation and menstrual pain. Sensations in the thighs, legs and recovery of bladder sensation and control were observed. The subject is able to walk with the aid of a walking frame with good restoration of movement in both the legs. Treatment is ongoing.

The schedule of injections for this patient is shown in Table 37.

TABLE 37

| Date | Route of administration | Cell types |
|---|---|---|
| 7/13 | test dose | non-neuronal |
| 7/27 | im | neuronal |
| 7/28 | im | non-neuronal |
| 7/29 | im | neuronal |
| 8/3 | im × 2 | neuronal |
| 8/4 | im × 2 | non-neuronal |
| 8/5 | im | neuronal |
| 8/9 | im | neuronal |
| 8/12 | im × 2 | neuronal |
| 8/16 | im | neuronal |
| 8/23 | im × 2 | hES |
| | | neuronal |
| 8/30 | im × 2 | neuronal |
| 9/1 | im × 4 | neuronal |
| 9/2 | im × 2 | neuronal |
| 9/8 | iv | neuronal |
| 9/12 | im | neuronal |
| 9/14 | im | neuronal and non-neuronal mixture |
| 9/22 | iv | neuronal |
| 9/27 | im | neuronal and non-neuronal mixture |
| 9/29 | im | neuronal and non-neuronal mixture |
| 9/30 | im | neuronal |
| 10/4 | im | neuronal and non-neuronal mixture |
| 10/6 | epidural × 2 vials | neuronal |
| 10/10 | im | neuronal |
| 10/19 | im | non-neuronal |
| 10/21 | im | neuronal |
| 10/24 | epidural | neuronal |
| 11/7 | epidural | neuronal |
| 11/14 | iv | neuronal |
| 11/15 | im | non-neuronal |
| 11/18 | im | non-neuronal |
| 12/1 | intrathecal | neuronal and non-neuronal mixture |
| 12/7 | deep spinal | non-neuronal |
| 12/23 | im | neuronal |
| 12/26 | im | non-neuronal |
| 1/5 | im | neuronal |
| 1/11 | im | neuronal |
| 1/17 | im | neuronal |
| 1/24 | iv | neuronal |
| 1/26 | im | neuronal |
| 2/1 | im | neuronal |
| 2/3 | im | neuronal |
| 2/9 | im | non-neuronal |
| 2/15 | im | non-neuronal |
| 2/22 | im | neuronal |
| 3/1 | im | non-neuronal |
| 3/9 | im | non-neuronal |
| 3/21 | im | neuronal |
| 3/28 | im | neuronal |
| 4/13 | epidural catheter | neuronal |
| 4/26 | im | neuronal |
| 5/2 | im | non-neuronal |
| 5/4 | epidural catheter | neuronal |
| 5/5 | epidural catheter | neuronal |
| 5/6 | epidural catheter | neuronal |
| 5/7 | im | neuronal |
| 5/21 | im | neuronal |
| 6/5 | im | neuronal |
| 6/12 | im | neuronal |
| 6/26 | iv × 2 | non-neuronal |
| 7/8 | im | neuronal |

Case Study 7

ReRo 1.3.4./006/220805/α, a thirty year old subject suffering from a C6-C7 paraplegic SCI was unable to move lower limbs and had no bowel control or bowel sensation. The subject had fine and deep pressure sensation only from the inter mammary region upwards. Thus, the subject had difficulty in sitting. The hands of the subject had very little strength, with very weak finger movement and the subject had difficulty in breathing.

The subject was treated according to the practice of the present invention by administration of a pharmaceutical composition comprising hES cells and their derivatives about three months after the injury. The subject regained ability to sit without support, suffers no giddiness, can sense pressure in the groin, has sensation in the medial side of the elbow and feels pain in the legs if the patient attempted to move. The subject breathes easily, has sensation in bladder and bowel, has sensation in legs and can now stand for a few minutes with support. The subject also has increased strength and movement in fingers. Treatment is ongoing.

The schedule of injections for this patient is shown in Table 38.

TABLE 38

| Date | Route of administration | Cell types |
|---|---|---|
| 2/22 | test dose | non-neuronal |
| 2/23 | im | neuronal |
| 2/24 | im | neuronal |
| 2/27 | im | non-neuronal |
| 2/28 | im | non-neuronal |
| 3/2 | im | neuronal |
| 3/3 | im | neuronal |
| 3/8 | epidural catheter | neuronal |
| 3/9 | epidural catheter × 2 | neuronal |
| 3/10 | epidural catheter × 2 | neuronal |
| 3/11 | iv | neuronal |
| 3/20 | im | neuronal |
| 3/22 | im | neuronal |
| 3/23 | im × 2 | neuronal |
| 3/24 | im | non-neuronal |
| 3/27 | im | non-neuronal |
| 4/5 | intrathecal | neuronal |
| 4/12 | im | neuronal |
| 5/1 | im epidural catheter × 4 | neuronal |
| 5/2 | im epidural catheter | neuronal |
| 5/10 | epidural catheter × 4 | neuronal |
| 5/11 | epidural catheter × 4 | neuronal |
| 5/12 | epidural catheter × 4 | neuronal |

Case Study 8

ReRo 1.3.4./007/221005/β, a twenty six year old subject, paraplegic as a result of SCI at D6, was unable to move both lower limbs, although able to sit without support. The subject had no bladder or bowel control, and had sensation only from the inter mammary area upwards.

The subject was administered a pharmaceutical composition comprising hES cells and their derivatives according to the practice of the present invention about ten months after the injury. The subject regained sensation in the lateral side of the body and up to the unbilious region bilaterally from the axillary area to the hipbone. The subject can walk with the aid of a walking frame and a caliper with motor power in the legs.

The schedule of injections for this patient is shown in Table 39.

TABLE 39

| Date | Route of administration | Cell types |
|---|---|---|
| 9/26 | test dose im | neuronal |
| 9/27 | im | neuronal and non-neuronal mixture |
| 9/28 | im | neuronal and non-neuronal mixture |
| 9/29 | im | neuronal |
| 9/30 | im | neuronal and non-neuronal mixture |
| 10/1 | im | neuronal and non-neuronal mixture |
| 10/3 | im | neuronal and non-neuronal mixture |
| 10/4 | im intrathecal | non-neuronal |
| 10/5 | m | neuronal |
| 10/6 | epidural | neuronal |
| 10/8 | m | non-neuronal |
| 10/10 | im | neuronal |
| 10/12 | im deep spinal | neuronal |
| 10/15 | iv | neuronal |
| 10/19 | im | non-neuronal |
| 10/24 | im | neuronal and non-neuronal mixture |
| 10/25 | epidural | neuronal |
| 12/8 | deep spinal | non-neuronal |
| 12/10 | intrathecal | non-neuronal |
| 12/11 | im | non-neuronal |
| 12/12 | deep spinal | non-neuronal |
| 12/13 | im | neuronal |
| 12/14 | epidural | neuronal |
| 12/15 | im | neuronal |
| 2/13 | im | neuronal |
| 2/15 | epidural | neuronal |
| 2/16 | iv | neuronal |
| 2/17 | im | neuronal |
| 5/24 | im iv | neuronal |
| 5/25 | im iv | non-neuronal neuronal |
| 5/26 | im iv × 2 | neuronal non-neuronal, neuronal |
| 5/27 | im × 2 iv × 2 | non-neuronal neuronal |
| 5/28 | im | neuronal, non-neuronal |
| 5/29 | im | neuronal, non-neuronal |
| 5/30 | epidural infusion | neuronal |
| 5/31 | im | neuronal |

Case Study 9

ReRo 1.3.4./008/151005/β, a twenty seven year old subject suffered with traumatic quadriplegia and had great difficulty talking and breathing, with rigid neck. The legs of the subject were paralysed and the subject had no finger movement and no sensation in the rest of the body.

The treatment via administration of a pharmaceutical composition comprising hES cells and their derivatives according to the practice of the present invention was started about two years after the injury. The subject experienced an improvement in neck movement, ease in speech, and improvement in control of voice tone. The subject found breathing to be less cumbersome and motor function returned with some finger movement. The legs became less spastic and the subject was able to sit unaided. Toe movements also resumed and the subject can move the shoulders.

The schedule of injections for this patient is shown in Table 40.

TABLE 40

| Date | Route of administration | Cell types |
|---|---|---|
| 5/26 | test dose | non-neuronal |
| 5/27 | im | neuronal |

TABLE 40-continued

| Date | Route of administration | Cell types |
|---|---|---|
| 5/28 | im | neuronal |
| 5/29 | im | neuronal |
| 5/30 | im | neuronal |
| 5/31 | im | neuronal |
| 6/1 | im | neuronal |
| 6/8 | im × 2 | neuronal |
|  |  | non-neuronal |
| 6/9 | im | neuronal |
| 6/10 | im × 2 | neuronal |
|  |  | non-neuronal |
| 6/11 | im × 2 | neuronal |
|  |  | non-neuronal |
| 6/12 | im × 2 | neuronal |
|  |  | non-neuronal |
| 6/13 | im × 2 | neuronal |
|  |  | non-neuronal |
| 6/14 | intrathecal | neuronal |
| 6/15 | im × 2 | neuronal |
|  |  | non-neuronal |
| 6/16 | im × 2 | neuronal |
|  |  | non-neuronal |
| 6/17 | im × 2 | neuronal |
|  |  | non-neuronal |
| 6/18 | im | non-neuronal |
| 6/19 | im × 2 | neuronal |
|  |  | non-neuronal |
| 6/20 | im × 2 | neuronal |
| 6/21 | im × 2 | neuronal |
|  |  | non-neuronal |
| 6/22 | im × 2 | neuronal |
| 6/23 | iv × 2 | non-neuronal |
| 6/24 | iv × 2 | non-neuronal |
| 6/25 | iv × 2 | non-neuronal |
| 6/26 | epidural catheter × 2 | neuronal |
| 6/27 | epidural catheter × 2 | neuronal |
| 6/28 | epidural catheter × 3 | neuronal |
| 7/21 | im | neuronal |
|  | iv | non-neuronal |
| 7/22 | im × 2 | neuronal |
|  |  | non-neuronal |
| 7/23 | im × 2 | neuronal |
| 8/22 | intrathecal | neuronal |

Case Study 10

ReRo 1.3.4./009/300106/α, a twenty five year old subject had a road accident and lost the ability to sit without support, the spine was prone to buckling, the subject lost bladder and bowel control and the subject suffered a total loss of power in the legs.

The subject was treated by administration of a pharmaceutical composition comprising hES cells and their derivatives according to the practice of the present invention about two years after the injury. The subject showed rapid improvement and can sit without support. The subject suffers no giddiness, has movement in both feet, regained sensation in the finger tips and can experience chill flowing through the spine.

Case Study 11

ReRo 1.3.4./010/020206/β, a twenty six year old subject with a SCI at D12-L1 as a result of a road traffic accident was unable to stand with the knees being contracted. The subject was able to sit without support and had normal sensations in the limbs. The subject had no bladder or bowel control and had increased spasticity.

The subject was treated about twelve years after the injury by administration of a pharmaceutical composition comprising hES cells and their derivatives according to the practice of the present invention. The subject experienced remarkable recovery in leg motor function with decreased spasticity, exhibited a fully extendable right leg and a return of strength to the left leg. The subject regained the ability to stand and walk with the aid of calipers and a walking frame. Bladder and bowel sensations also returned in the subject.

The schedule of injections for this patient is shown in Table 41.

TABLE 41

| Date | Route of administration | Cell types |
|---|---|---|
| 3/27 | test dose | non-neuronal |
| 3/29 | im | non-neuronal |
|  | iv | neuronal |
| 3/30 | im | neuronal |
| 3/31 | im | neuronal |
| 4/1 | im | neuronal |
| 4/2 | im | non-neuronal |
| 4/3 | im | neuronal |
| 4/4 | im | neuronal |
| 4/5 | caudal | neuronal |
| 4/7 | epidural | neuronal |
| 4/8 | im | neuronal |
| 4/10 | im | neuronal |
| 4/13 | im | neuronal |
| 4/14 | im | neuronal |
| 4/14 | im | neuronal |
| 4/16 | im | neuronal |
| 4/18 | iv | non-neuronal |
| 4/22 | im | neuronal |
| 4/23 | im | neuronal |
| 4/24 | epidural catheter | neuronal |
| 4/25 | epidural catheter | neuronal |
| 4/26 | iv | neuronal |
| 4/27 | im | neuronal |
| 4/28 | im | neuronal |
| 4/29 | im | neuronal |
| 4/30 | im | neuronal |
| 5/1 | im | neuronal |
| 5/2 | im | non-neuronal |
| 5/3 | im | neuronal |
| 5/4 | im | neuronal |
| 5/5 | im | neuronal |
| 5/7 | im | neuronal |
| 5/8 | im | non-neuronal |
| 5/9 | im | non-neuronal |
| 5/10 | im | neuronal |
| 5/11 | caudal | neuronal |
| 5/12 | im | neuronal |
| 5/13 | im | neuronal |
| 5/14 | im | neuronal |
| 5/16 | im | non-neuronal |
| 5/17 | im | neuronal |
| 5/20 | epidural | neuronal |
| 5/21 | im | neuronal |
| 5/22 | im | neuronal |
| 5/23 | im | neuronal |
| 5/24 | im | neuronal |

Case Study 12

The patient was a 26 year old male with paraplegia after an injury between D6-D8. He suffered a traumatic road accident in September 2004. He was totally bedridden with no feeling below the chest, no bladder or bowel control, and no sensation or motor power from chest downwards. He had a very deep bed sore in the lower back in which his sacrum could be seen.

The patient started hES cells on Apr. 27, 2006. Because of the bedsore he could not undergo any O/T procedures and was given daily dosages of cells intravenously and intramuscularly, and eventually had hES cells applied directly to his bedsore. He was also given intravenous infusions.

On his 11$^{th}$ day of treatment he could stand with full calipers (waist to ankle) and a walker and took 2 steps. As time continued his muscle power increased and after 4 months he could take up to 100 steps and could stand for up to 20 mins. He is able to feel his legs and move them too. He is also able to feel bladder and bowel fullness and is able to walk now with just a knee brace and the walker for support. His bed sore has healed and he has resumed his studies.

The schedule of injections for this patient is shown in Table 42.

TABLE 42

| Date | Route of administration | Cell types |
|---|---|---|
| 4/28 | im | neuronal (test dose) |
|  | iv |  |
| 4/29 | iv | neuronal |
|  | im | non neuronal |
| 4/30 | iv | neuronal |
|  | im | non neuronal |
| 5/1 | iv | neuronal |
|  | im | non neuronal |
| 5/2 | iv | neuronal |
|  | im | non neuronal |
| 5/3 | iv infusion | neuronal |
|  | im | non neuronal |
| 5/4 | iv infusion | neuronal |
|  | im | non neuronal |
| 5/5 | iv | neuronal |
|  | im | non neuronal |
| 5/6 | iv | neuronal |
|  | im | non neuronal |
| 5/8 | iv infusion | neuronal |
|  | im |  |
| 5/9 | iv infusion | neuronal |
|  | im | non neuronal |
| 5/10 | iv infusion | neuronal |
|  | im | non neuronal |
| 5/11 | iv | neuronal |
|  | im |  |
| 5/12 | iv | neuronal |
|  | im | non neuronal |
| 5/13 | iv | neuronal |
|  | im |  |
| 5/14 | iv | neuronal |
|  | im | non neuronal |
| 5/15 | iv infusion | non neuronal |
|  | im |  |
| 5/16 | iv infusion | non neuronal |
|  | im |  |
| 5/17 | iv | neuronal |
|  | im | non neuronal |
| 5/18 | iv | neuronal |
|  | im | non neuronal |
| 5/19 | iv | neuronal |
|  | im | non neuronal |
| 5/20 | iv | neuronal |
|  | im | non neuronal |
| 5/21 | iv | neuronal |
|  | im | non neuronal |
| 5/22 | iv infusion | non neuronal |
|  | im |  |
| 5/23 | iv infusion | non neuronal |
|  | im |  |
| 5/24 | iv | neuronal |
|  | im | non neuronal |
| 5/25 | iv | neuronal |
|  | im | non neuronal |
| 5/26 | iv | neuronal |
|  | im | non neuronal |
| 5/27 | iv | neuronal |
|  | im | non neuronal |
| 5/28 | iv | neuronal |
|  | im | non neuronal |
| 5/29 | iv infusion | neuronal |
|  | im | non neuronal |
| 5/30 | iv infusion | neuronal |
|  | im | non neuronal |
| 5/31 | iv | neuronal |
|  | im | non neuronal |
| 6/1 | iv | neuronal |
|  | im | non neuronal |
| 6/2 | iv | neuronal |
|  | im | non neuronal |
| 6/3 | iv | neuronal |
|  | im | non neuronal |
| 6/4 | iv | neuronal |
|  | im | non neuronal |
| 6/5 | iv infusion | neuronal |
|  | im | non neuronal |
| 6/6 | iv infusion | neuronal |
|  | im | non neuronal |
| 6/7 | iv | neuronal |
|  | im | non neuronal |
| 6/8 | im | neuronal |
|  | iv | non neuronal |
| 6/9 | im | neuronal |
|  | iv | non neuronal |
| 6/10 | im | neuronal |
|  | iv | non neuronal |
| 6/11 | im | neuronal |
|  | iv | non neuronal |
| 6/12 | iv infusion | neuronal |
| 6/13 | iv infusion | non neuronal |
|  | im |  |
| 6/14 | iv | neuronal |
|  | im | non neuronal |
| 6/15 | iv | neuronal |
|  | im | non neuronal |
| 6/16 | iv | neuronal |
|  | im | non neuronal |
| 6/17 | iv | neuronal |
|  | im | non neuronal |
| 6/18 | iv | neuronal |
|  | im | non neuronal |
| 6/20 | iv | neuronal |
|  | iv infusion |  |
|  | im |  |
| 6/21 | iv | neuronal |
|  |  | non neuronal |
| 6/22 | iv | non neuronal (2) |
|  | im |  |
| 6/23 | iv | non neuronal (2) |
| 6/24 | iv | non neuronal (2) |
| 6/25 | iv | non neuronal (2) |
| 6/26 | iv | non neuronal |
|  | iv infusion |  |
| 6/27 | iv | non neuronal |
|  | iv infusion |  |
|  | im |  |
| 6/28 | iv | neuronal |
|  | im |  |
| 6/29 | iv | neuronal |
|  | im | non neuronal × 2 |
| 6/30 | iv | neuronal |
|  | im | non neuronal × 2 |
| 7/1 | iv | neuronal |
|  | im | non neuronal × 2 |
| 7/2 | iv | neuronal |
|  | im | non neuronal × 2 |
| 7/3 | iv | neuronal |
|  | iv infusion | non neuronal × 2 |
|  | im |  |
| 7/4 | iv | neuronal |
|  | iv infusion | non neuronal |
|  | im |  |
| 7/5 | iv | neuronal × 2 |
|  | im |  |
| 7/6 | iv | neuronal × 2 |
|  | im |  |
| 7/7 | iv | neuronal |
|  | im |  |
| 7/8 | iv | neuronal |
|  | im | non neuronal × 2 |
| 7/9 | iv | neuronal |
|  | im | non neuronal |
| 7/11 | iv | neuronal |
|  | iv infusion | non neuronal |
|  | im |  |
| 7/12 | iv | neuronal |
|  | iv infusion |  |
| 7/17 | im | neuronal |
|  | dressing | non neuronal |
| 7/18 | iv infusion | non neuronal |
|  | dressing |  |

TABLE 42-continued

| Date | Route of administration | Cell types |
|---|---|---|
| 7/19 | iv infusion | non neuronal |
| | im | |
| 7/20 | iv | neuronal |
| | im | non neuronal |
| | dressing | |
| 7/21 | iv | neuronal |
| | im | non neuronal |
| | dressing | |
| 7/22 | iv | neuronal |
| | im | non neuronal |
| | dressing | |
| 7/23 | iv | neuronal |
| | im | non neuronal |
| 7/24 | iv | neuronal |
| | im | non neuronal |
| 7/25 | im | neuronal |
| | dressing | non neuronal × 2 |
| 7/26 | m | neuronal |
| | dressing | non neuronal × 2 |
| 7/27 | im | neuronal |
| | | non neuronal |
| 7/28 | im | non neuronal |
| | dressing | |
| 7/29 | im | neuronal |
| | dressing | non neuronal |
| 7/30 | im | neuronal |
| | | non neuronal |
| 7/31 | im | non neuronal |
| | dressing | |
| 8/1 | im | non neuronal × 2 |
| | dressing | |
| 8/2 | im | non neuronal × 2 |
| | dressing | |
| 8/3 | im | non neuronal × 2 |
| 8/4 | im | non neuronal × 2 |
| 8/5 | im | non neuronal × 2 |
| | dressing | |
| 8/6 | im | non neuronal × 2 |
| 8/7 | im | non neuronal × 2 |
| | dressing | |
| 8/8 | im | non neuronal × 2 |
| 8/9 | im | non neuronal × 2 |
| | dressing | |
| 8/10 | im | non neuronal × 2 |
| 8/11 | im | non neuronal × 2 |
| 8/12 | im | non neuronal × 2 |
| | dressing | |
| 8/13 | im | non neuronal × 2 |
| 8/14 | im | non neuronal × 2 |
| | dressing | |
| 8/15 | im | non neuronal × 2 |
| | dressing | |
| 8/16 | im | non neuronal × 2 |
| 8/17 | im | non neuronal × 2 |
| 8/18 | iv infusion | neuronal × 3 |
| | im | |
| 8/19 | im | neuronal × 3 |
| | dressing | |
| 12/5 | im | non neuronal |
| 12/6 | iv infusion | non neuronal |
| 12/7 | iv infusion | non neuronal |
| | im | |
| | dressing | |
| 12/8 | epidural (intrathecal) | neuronal |
| 12/9 | im | non neuronal × 2 |
| | dressing | |
| 12/10 | im | non neuronal × 2 |
| | dressing | |
| 12/11 | im | non neuronal × 2 |
| | dressing | |
| 12/12 | epidural (catheter) | neuronal × 2 |
| 12/13 | epidural (catheter) | neuronal × 2 |
| 12/14 | epidural (catheter) | neuronal × 2 |
| 12/15 | iv infusion | neuronal, non neuronal |
| | im | |
| 12/16 | iv infusion | neuronal, non neuronal |

Case Study 13

The patient is a 22 year old male who suffered a horse riding accident in June, 2006 and is a paraplegic at T-12, L-1. He had no power below the waist, no bowel or bladder control, and no sensation below waist.

The patient started treatment in September 2006 admitted for 6 weeks. He responded to hES cells and within a week he was able to stand and walk a few steps with full calipers (waist to ankle) and walker. He has progressed and is on the knee brace with which he can stand for up to 30 mins with a walker. He now has full sensation and bowel and bladder control. He also has good balance with the stick and also the crutches. He is able to go up and down the stairs with the caliper and the crutches.

The schedule of injections for this patient is shown in Table 43.

TABLE 43

| Date | Route of administration | Cell types |
|---|---|---|
| 10/4 | im | non neuronal (test dose) |
| 10/5 | im | non neuronal |
| 10/6 | im | non neuronal |
| 10/7 | im | non neuronal |
| 10/8 | im | non neuronal |
| 10/9 | iv infusion | neuronal |
| 10/10 | iv infusion | neuronal |
| 10/11 | im | non neuronal |
| 10/12 | im | non neuronal |
| 10/13 | im | non neuronal |
| 10/14 | im | non neuronal |
| 10/15 | im | non neuronal |
| 10/16 | caudal | neuronal |
| 10/17 | im | non neuronal |
| 10/18 | im | non neuronal |
| 10/19 | iv infusion | non neuronal |
| | im | |
| 10/20 | iv infusion im | non neuronal |
| 10/21 | im | non neuronal |
| 10/22 | im | non neuronal |
| 10/23 | lumbar | neuronal |
| 10/27 | im | non neuronal |
| 10/25 | im | non neuronal |
| 10/26 | im | non neuronal |
| 10/27 | im | non neuronal |
| 10/28 | im | non neuronal |
| 10/29 | im | non neuronal |
| 10/30 | epidural catheter | neuronal |
| 10/31 | epidural catheter | neuronal |
| 11/1 | epidural catheter | neuronal |
| 11/2 | im | non neuronal |
| 11/3 | im | non neuronal |
| 11/4 | im | non neuronal |
| 11/5 | im | non neuronal |
| 11/6 | im | non neuronal |
| 11/7 | im | non neuronal |
| 11/8 | im | non neuronal |
| 11/9 | caudal | neuronal |
| 11/10 | im | non neuronal |
| 11/11 | im | non neuronal |
| 11/12 | im | non neuronal |
| 11/13 | iv infusion | mixed |
| | im | non neuronal |
| 11/14 | im | non neuronal |
| | iv infusion | |
| 11/15 | im | non neuronal |
| 12/31 | iv | mixed |
| 1/10 | im | non neuronal |
| 1/11 | iv infusion | mixed |
| 1/12 | iv infusion | mixed |
| 1/13 | im | non neuronal |
| 1/14 | im | non neuronal |
| 1/15 | caudal | neuronal |
| 1/16 | im | non neuronal |
| 1/17 | im | non neuronal |
| 1/18 | im | non neuronal |

TABLE 43-continued

| Date | Route of administration | Cell types |
|---|---|---|
| 1/19 | lumbar | neuronal |
| 1/20 | im | non neuronal |
|  |  | mixed |
| 1/21 | im | mixed |
| 1/22 | im | mixed |
| 1/23 | epidural catheter | neuronal |
| 1/24 | im | neuronal |
|  | iv |  |
| 1/25 | im | neuronal |
| 1/26 | infusion | mixed |
|  | im | neuronal |
| 1/27 | infusion | mixed |
|  | im | neuronal |

Case Study 14

The patient is a 26 year old female traumatic paraplegic at T-12, L-1 who suffered a road traffic accident in September 2004. She had no feeling below the chest and she had no bowel or bladder control. There was no motor power in either leg and she was wheel chair bound.

The patient started hES cells in March 2006. She was able to stand and walk a few steps with full calipers (waist to ankle) and walker after 9 days and continued to progress. Her current status is that she can walk continuously with caliper and walker and also stand using the knee brace. Bowel and bladder sensations have been restored with control and without the usage of any catheterization or suppository. Sensation has improved to the ankle levels.

The schedule of injections for this patient is shown in Table 44.

TABLE 44

| Date | Route of administration | Cell types |
|---|---|---|
| 3/27 | im | non neuronal (test dose) |
| 3/29 | iv | neuronal |
|  | im | non neuronal |
| 3/30 | im | neuronal |
| 3/31 | im | neuronal |
| 4/1 | im | neuronal |
| 4/3 | im | neuronal |
| 4/4 | im | neuronal |
| 4/5 | Epidural (caudal) | neuronal × 2 |
| 4/7 | Epidural (intrathecal) | neuronal × 2 |
| 4/9 | im | neuronal |
| 4/10 | im | neuronal |
| 4/12 | im | neuronal |
| 4/13 | im | neuronal |
| 4/14 | im | neuronal |
| 4/15 | im | neuronal |
| 4/16 | im | neuronal |
| 4/17 | im | neuronal |
| 4/18 | iv | non neuronal |
| 4/20 | im | neuronal |
| 4/21 | im | neuronal |
| 4/22 | im | neuronal |
| 4/24 | Epidural (catheter) | neuronal × 4 |
| 4/25 | Epidural (catheter) | neuronal × 4 |
| 4/26 | iv (catheter) | neuronal × 4 |
| 4/27 | im | neuronal |
| 4/28 | im | neuronal |
| 4/29 | im | neuronal |
| 4/30 | im | neuronal |
| 5/1 | im | neuronal |
| 5/2 | im | non neuronal |
| 5/3 | im | neuronal |
| 5/4 | im | neuronal |
| 5/5 | im | neuronal |
| 5/7 | im | neuronal |
| 5/8 | im | non neuronal |
| 5/10 | im | neuronal |

TABLE 44-continued

| Date | Route of administration | Cell types |
|---|---|---|
| 5/11 | EPI (caudal) | neuronal |
| 5/13 | IM | neuronal |
| 5/14 | IM | neuronal |
| 5/16 | IM | non neuronal |
| 5/17 | IM | neuronal |
| 5/18 | EPI (catheter) | neuronal × 2 |
| 5/19 | EPI (catheter) | neuronal × 2 |
| 5/20 | EPI (catheter) | neuronal × 2 |
| 5/21 | im | neuronal |
| 5/22 | im | neuronal |
| 5/23 | im | neuronal |
| 5/24 | im | neuronal |
| 5/25 | im | neuronal |
| 10/25 | im | non neuronal |
|  |  | mixed |
| 10/26 | im | non neuronal |
|  | iv infusion | mixed |
| 10/27 | im | non neuronal |
| 10/28 | im | non neuronal |
| 10/29 | im | non neuronal |
| 10/30 | caudal | neuronal |
| 10/31 | im | non neuronal |
| 11/1 | im | non neuronal × 2 |
| 11/2 | im | non neuronal × 2 |
| 11/3 | lumbar | neuronal |
| 11/4 | infusion | neuronal |
| 11/5 | im | non neuronal × 2 |
| 11/6 | im | non neuronal × 2 |
| 11/7 | im | non neuronal × 2 |
| 11/8 | epidural catheter | neuronal |
| 11/9 | epidural catheter | neuronal |
| 11/10 | epidural catheter | neuronal |
| 11/11 | im | non neuronal × 2 |
| 11/12 | im | non neuronal |
|  | infusion | mixed |
| 11/13 | caudal | neuronal |
|  | infusion | mixed |
| 11/14 | im | neuronal |

Human Embryonic Stem Cell Culture Methodology

The hES cells used as the starting material for the cell lines developed under the present invention are derived from a 2 to 7 day old embryo prior to its implantation into the uterus, e.g., a 2 to 4 day old embryo, e.g., a 3 day old embryo.

For embryo isolation, the ova are collected with consent from human donors who are undergoing a regular IVF cycle. The ova are fertilized by the sperm and cultured by conventional methods to obtain the embryos. Extra embryos are incubated for variable periods for development of the cell line.

The embryo is suspended in a small amount of minimal essential medium (e.g., RPMI, e.g., RPMI 1640 with 2.2 g/L sodium bicarbonate) and the hES cells are isolated from the embryo by mechanical means (e.g., shaking). Additional medium is added to the isolated cells along with a progestin and a βhCG agonist. In one embodiment, progesterone (16-64 µl of 250 mg/ml) and βhCG (16-64 µl of 5000 iu/ml) are added. The isolated cells are cultured for 12-48 hours, e.g., 24 hours, at a temperature of between 34-38° C., in an environment of 3.5-6% carbon dioxide.

In one embodiment, the hES cells are cultured under anaerobic or substantially anaerobic conditions in order to expand the cells while preventing differentiation. "Substantially anaerobic" is defined as less than about 10% $O_2$, e.g., less than 8%, 6%, 4%, 2%, or 1% $O_2$. Low oxygen conditions may be created using multi-gas ($CO_2$, $O_2$, $N_2$) cell incubators in which the oxygen level may be set between 0% and 20% by replacing the ambient air with nitrogen gas. Examples of multi-gas incubators include the Fisher 11-730 series, the Napco 7000 series, the Sanyo MCO series, the Jouan IG750, and the Heraeus Heracell 150. In another embodiment, the cells are cultured in a $CO_2$ incubator and the level of oxygen is controlled by the shape and position of the flask in which the cells are contained. For example, when a cell culture flask is maintained in a vertical position, much of the culture medium in the flask is substantially anaerobic. In contrast, when the cell culture flask is maintained in a horizontal position, the culture medium is substantially aerobic. The level of oxygen in the culture medium can be varied between substantially anaerobic and substantially aerobic by altering the shape and/or position of the cell culture flask within the incubator or the amount of medium in the flask (e.g., the amount of head space).

During the expansion stage, flasks may be maintained in a vertical position rather than horizontal. In one embodiment, incubation is carried out in a culture vessel where the volume is almost completely occupied by the medium and the vessel is kept in a vertical position. As a consequence, a substantial proportion of the cells do not adhere to the walls of the culture flask, and the culture medium is substantially anaerobic.

Under such growth conditions, cell-doubling or replication cycles are at their maximum, and cellular differentiation processes are substantially inhibited. Cell replication cycles during expansion proceed for 12-48 hours, e.g., 24 hours.

For passaging or re-culture of the hES cells, the cell suspension is centrifuged, the cell pellet is resuspended in a small amount of fresh culture medium comprising progesterone and βhCG, the cells are aliquoted and additional fresh medium without progesterone and βhCG is added. In one embodiment, the ratio of the aliquot of incubated stem cells to the fresh cell medium is about 1:3.5 to about 1:35 volume/volume. The cells are re-incubated at 34-38° C. in a water jacketed incubator supplemented with an atmosphere of 3.5-6% carbon dioxide under substantially anaerobic conditions for 12 to 48 hours, e.g., 24 hours. At this point the cells may be passaged for continued expansion or stored for future use.

hES cells cultured under such conditions remain in a largely undifferentiated form as determined by alkaline phosphatase activity and the absence of any markers characteristic of cellular specialization or differentiation. However, it may be noted that no cell population is obtained which is completely differentiated or completely undifferentiated. The cell population is a mix of differentiated and undifferentiated cell lines, with a ratio ranging from about 4:1 to about 10:1 undifferentiated to differentiated cells.

For storage of the expanded hES cells, e.g., in a deep freezer or in liquid nitrogen, a cryopreservation agent, including but not limited to 0.2-2% (w/v) dimethyl sulphoxide (DMSO), may be added to the culture medium. The level of DMSO used is less than typically used for cryopreservation (e.g., 2-84 μl/0.5 ml tube) to avoid inducing differentiation or damage to the cells. The ratio of the amount of cryopreservation agent to that of culture medium containing stem cells may vary from about 1:500 to about 16:1000. Other cryopreservation agents include without limitation glycerol, propanediol, butanediol, ethanol, glucose, D-glucose, sucrose, trehalose, mannitol, paparavine, formamide, probuchol, curcumin, polyvinylpyrrolidone, polyethylene glycol, chondroitin sulfate, glycosaminoglycan dimethyl sulfoxide, glutamine, and sodium pyruvate. The freezing temperature for the cell suspension may be varied from about −15 to about −80° C., e.g., about −15 to about −40° C. In contrast to other techniques for the storage of human embryonic stem cells and their derivatives, there is no need for flash freezing or storage in "straws". After storage, the cells may be prepared for continued expansion or for differentiation by collecting the cells by centrifugation and resuspending the cell pellet in fresh medium.

Partial differentiation of the expanded hES cells (e.g., after expansion of freshly isolated hES cells or storage of previously expanded cells) is carried out by sedimenting the cell suspension in a centrifuge (e.g., at between 700-1400 rpm for 5-12 minutes), removing and discarding the supernatant, and resuspending the cells in a small amount of fresh medium (e.g., RPMI) containing a progestin and a βhCG agonist. The cells are then aliquoted and additional culture medium (e.g., a minimal essential medium such as RPMI or DMEM, e.g., 1× glutamic acid free DMEM or DMEM with 4.5 g/L glucose and 3.7 g/L sodium bicarbonate) without progestin or βhCG is added. The cells are cultured under substantially aerobic conditions (e.g., in a flask in a horizontal position) for 12 to 48 hours, e.g., 24 hours. "Substantially aerobic" is defined as at least about 15% $O_2$, e.g., at least about 18% or 20% $O_2$. Under substantially aerobic conditions the hES cells will begin to differentiate. The differentiation pathway for the hES cells is dependent on the culture medium used during the differentiation stage. To produce neuronal progenitor cells, the hES cells are cultured in DMEM or its equivalent. To produce progenitor cells other than neuronal progenitors, the hES cells are cultured in RPMI or its equivalent. After the 12-48 hour replication cycle, the cells may be collected and resuspended in fresh medium to continue differentiation. In general, the differentiation stage should not last more than 48-72 hours as further differentiation beyond this time produces cells that are not suitable for transplantation using the methods of the present invention.

Once the cells are partially differentiated, the cells can either be stored for future use by adding a cryopreservative and storing the cells at −15 to about −80° C. as described above or preparing the cells for usage in the methods of the invention. To prepare the cells for usage, the cells are aliquoted, fresh medium is added (e.g., DMEM or RPMI as appropriate) and the cells are cultured for 12-48 hours, e.g., 24 hours, under substantially anaerobic conditions to prevent further differentiation. The cells are then aliquoted into fresh medium for continued expansion or collected by centrifugation and resuspended in a biocompatible solution (e.g., saline) in preparation for transplantation. At this point the cells may be transplanted into patients or stored at +4° C. to −80° C. for future transplantation. Storage may be in any suitable container including but not limited to test tubes, vials, syringes, etc. that may facilitate transportation or clinical use. In one embodiment, the resuspended cells in biocompatible solution are stored in a ready-to-use form (e.g., in a prefilled syringe). When needed, aliquots of cells are thawed naturally without the need for water baths or incubators.

Under the described storage conditions in a biocompatible solution, cell viability of >40% is observed after re-thawing even after six months of storage, with no detectable genotypic (genetic instability) or phenotypic alterations such as aneuploidy or heteroploidy.

At each stage of expansion, differentiation, and storage, an aliquot of the cells is tested for viability via trypan blue exclusion and microscopic examination. An aliquot of the cell culture is also tested for microbiological contamination. A further aliquot of the cell suspension is also placed on a haemocytometer and examined microscopically in order to determine the cell density. A further aliquot is also taken for testing alkaline phosphatase activity as a marker for the state of differentiation of the cell culture.

During storage, the cells may be tested once a month for their karyotype, to test for genetic instability arising as a result of the culture methodology.

EXAMPLES

EXAMPLE 1

For embryo isolation, ova were collected with consent from a human donor who underwent a regular IVF cycle, which produced 8 follicles. The ova were fertilized by the sperm and cultured by conventional methods to obtain the embryos. Three of the embryos were transplanted into the donor. The extra embryos were incubated for variable periods for development of an hES cell line.

The embryo, either intact or in broken condition, was suspended in culture media. Further, 84 μl of progesterone (250 mg/ml) and 84 μl of βhCG (5000 iu/ml) were added. The media with the embryonic cells were tested for any contamination, and any infected embryo was discarded. The cells of the embryos in this form were used for expansion and storage.

After one day of incubation, 1 ml of the embryonic cell containing media were introduced in a 40 ml cell culture medium (DMEM or RPMI) in a 50 ml container along with progesterone and βhCG. The culture medium along with the stem cells was incubated in a horizontal position at ambient temperature in an environment containing carbon dioxide. Table 45 shows some of the experimental conditions followed for this method.

was found to be filled up to the 37 ml mark after the 48 hr incubation. Aliquots of 0.5 ml were taken for storage at this stage. After 72 hrs of incubation in DMEM, long strands of cells cross linked like nerve tissue were observed. The RPMI media incubation produced a few small sized cells and a few cells accumulating around a central cell. Aliquots of 0.5 ml were taken for storage at this stage.

An aliquot of the embryonic cells grown in culture containing media were introduced into more cell medium (RPMI or DMEM) with other test components, in a sterile container (Tarsons steriflask). The stem cells were incubated at ambient temperature in an environment of carbon dioxide in horizontal position for various time periods ranging from 18 hrs to 5 days. After 24 hrs of incubation, aliquots of about 0.5 ml were again introduced into more culture media and reincubated. Aliquots were taken for preparing ready to use compositions as well as for storage after different incubation stages. Table 46 depicts some experimental conditions followed for expansion of hES cells.

EXAMPLE 2

The embryo, either intact or in broken condition, was suspended in culture media. Further, 84 μl of progesterone and 84 μl of βhCG were added. The media with the embryonic cells were tested for any contamination, and any infected embryo was discarded. The cells of the embryos in this form were used for expansion and storage.

TABLE 45

| S. No. | (a) Embryo stage in days | (b) Embryo state | (c) Cell Media | (d) Amount of (c) | (e) Addition to Media | (f) Incubation time | (g) aliquot of (f) | (h) Cell Media | (i) Amount of (h) | (j) Container volume | (k) Incubation temp degree C. | (l) % CO2 in environment |
|---|---|---|---|---|---|---|---|---|---|---|---|---|
| 1 | 2 | Intact | IVF media | 2.5 ml | FF | 24 hrs | — | — | — | — | 36 | 4 |
| 2 | 2 | Intact | IVF media | 2.5 ml | A | 24 hrs | — | — | — | — | 36.5 | 4.5 |
| 3 | 3 | Broken | RPMI | 2.5 ml | A | 24 hrs | 0.5 ml | RPMI | 45 ml | 50 ml | 37 | 5 |
| 4 | 3 | Broken | RPMI | 2.5 ml | A & B | 24 hrs | 1.0 ml | RPMI | 46 ml | 50 ml | 38 | 5 |
| 5 | 3 | Broken | DMEM | 2.5 ml | B | 24 hrs | 0.5 ml | DMEM | 35 ml | 50 ml | 37 | 5 |

TABLE 46

| S. No. | (a) Amount of ESC culture | (b) Cell Media | (c) Amount of (b) | (d) Addition to Media | (e) Container volume | (f) Incubation temperature | (g) % CO2 in environment | (h) Incubation time | (i) Aliquot of (h) | (j) Culture medium | (k) Container volume | (l) Storage temp |
|---|---|---|---|---|---|---|---|---|---|---|---|---|
| 1 | 0.5 ml | RPMI | 35 ml | A | 50 ml | 36.5 | 5 | 24 | 0.5 ml | RPMI | 0.5 ml | −72 |
| 2 | 1.0 ml | RPMI | 38 ml | B | 50 ml | 37 | 5 | 24 | .25 ml | RPMI | 0.5 ml | −20 |
| 3 | 1.5 ml | DMEM | 45 ml | AB | 50 ml | 37 | 5 | 48 | 1.0 ml | DMEM | 1.5 ml | −20 |
| 4 | 2.0 ml | RPMI | 46 ml | A | 50 ml | 37.2 | 5 | 48 | 1.5 ml | RPMI | 1.5 ml | −18 |
| 5 | 2.5 ml | DMEM | 45 ml | A | 50 ml | 36.8 | 5 | 24 | 0.5 ml | DMEM | 1.5 ml | −72 |

FF = follicular fluid aspirated along with the ovum during the IVF cycle, 16-84 μl;
A = progesterone;
B = βhCG After 24 hrs of incubation, equal numbers of nucleated (partly differentiated) cells and blank (undifferentiated) cells were observed. Aliquots of about 0.5 ml were taken for storage at this stage. After 48 hrs of incubation, oblong shape cells with few strands were observed with DMEM media. However, when RPMI media was used, many nucleated cells with varied shapes were observed. The volume of the container After one day of incubation, 1 ml of the embryonic cell containing media was introduced in a 46 ml cell culture medium (DMEM or RPMI) in a 50 ml container along with progesterone and βhCG. The stem cells were incubated in a vertical position at ambient temperature in an environment of carbon dioxide. Table 47 shows some of the working example variables used for this experiment.

TABLE 47

| S. No. | (A) Embryo stage in days | (B) Embryo state | (C) Cell Media | (D) Amount of (c) | (E) Addition to Media | (F) Incubation time | (G) aliquot of (f) | (H) Cell Media | (I) Amount of (h) | (J) Container volume | (K) Incubation temp | (L) % CO2 in environment |
|---|---|---|---|---|---|---|---|---|---|---|---|---|
| 1 | 2 | Intact | IVF media | 2.5 ml | FF | 24 hrs | — | — | — | — | 36 | 4 |
| 2 | 2 | Intact | IVF media | 2.5 ml | A | 24 hrs | — | — | — | — | 36.5 | 4.5 |
| 3 | 3 | Broken | RPMI | 2.5 ml | A | 24 hrs | 0.5 ml | RPMI | 45 ml | 50 ml | 37 | 5 |
| 4 | 3 | Broken | RPMI | 2.5 ml | B | 24 hrs | 1.0 ml | RPMI | 46 ml | 50 ml | 38 | 5 |
| 5 | 3 | Broken | DMEM | 2.5 ml | A& B | 24 hrs | 0.5 ml | DMEM | 35 ml | 50 ml | 37 | 5 |

TABLE 48

| S. No. | (a) Amount of ESC culture | (b) Cell Media | (c) Amount of (b)) | (d) Addition to Media | (e) Container volume | (f) Incubation temperature | (g) % CO2 in environment | (h) Incubation time hrs | (i) Aliquot of (h) | (j) Culture medium | (k) Container volume | (l) Storage temp |
|---|---|---|---|---|---|---|---|---|---|---|---|---|
| 1 | 0.5 ml | RPMI | 35 ml | A | 50 ml | 36.5 | 5 | 24 | 0.5 ml | RPMI | 0.5 ml | −40 |
| 2 | 1.0 ml | RPMI | 38 ml | A | 50 ml | 37 | 5 | 24 | .25 ml | RPMI | 0.5 ml | −20 |
| 3 | 1.5 ml | DMEM | 45 ml | B | 50 ml | 37 | 5 | 48 | 1.0 ml | DMEM | 1.5 ml | −18 |
| 4 | 2.0 ml | RPMI | 46 ml | A | 50 ml | 37.2 | 5 | 48 | 1.5 ml | RPMI | 1.5 ml | −20 |
| 5 | 2.5 ml | DMEM | 45 ml | AB | 50 ml | 36.8 | 5 | 24 | 0.5 ml | DMEM | 1.5 ml | −72 |

After 24 hrs of incubation, nucleated cells (partly differentiated) and blank cells (undifferentiated) were observed in a ratio of about 1:4. After 48 hrs of incubation, nucleated cells and blank cells in the ratio 1:2 were observed. Aliquots of 0.5 ml were taken for storage at the 24 hr and 48 hr stage.

0.5 ml of the embryonic cells grown in culture containing media were introduced in 46 ml cell medium (RPMI or DMEM) with other test components, in a 50 ml sterile container (Tarsons steriflask). The stem cells were incubated in a horizontal position at ambient temperature in an environment containing carbon dioxide. After 24 hrs of incubation, aliquots of 0.5 ml were again introduced into 46 ml of culture media and reincubated. Table 48 depicts some experimental conditions followed for expansion of hES cells.

Aliquots were taken for preparing ready to use compositions as well as for storage after the 24 hr incubation stage.

EXAMPLE 3

Storage

For storage, hES cells were taken in a 0.5 ml storage tube and a cryopreservation agent such as 0.2% DMSO in a quantity of 16 µl was added and after gentle shaking were stored at −20° C. The cells were thawed naturally for making ready to use compositions or for further expansion. The viability of the thawed cells was tested and 64% to 84% of the cells were found to be viable. The stored cells were tested for contamination as well as viability after regular intervals. Table 49 shows the actual parameters followed for storage in five different experiments as well as the viability of the cells after thawing.

TABLE 49

| S. No. | Amount of Cell suspension | DMSO quantity | DMSO % | Media used | Viability of thawed cells |
|---|---|---|---|---|---|
| 1 | 0.5 ml | 16 µl | 0.2 | NaCl | 74% |
| 2 | 0.5 ml | 32 µl | 1.4 | NaCl | 66% |
| 3 | 0.5 ml | 64 µl | 0.4 | NaCl | 70% |
| 4 | 0.5 ml | 48 µl | 0.2 | NaCl | 78% |
| 5 | 0.5 ml | 16 µl | 0.2 | NaCl | 88% |

EXAMPLE 4

Various tests were carried out for checking any contamination or infection or abnormality in the embryonic cells at various intervals of the expansion and storage stages and to identify the hES derivatives that were present in each culture. The different tests include those for HIV, HbSAg (for hepatitis), conventional PCR for Kochs test (for tuberculosis), chromosomal analysis by CG method of giemsa banding, Bilirubin by the Jendrasiik and Grof method and Albumin using BCG Dye binding method (for liver progenitor cells), insulin via CLIA method (for pancreatic progenitor cells), neurofilament by immunohistochemical method (for neuronal progenitor cells), CD34 testing by immunohistochemical method (for hematopoietic progenitor cells), Alkaline Phosphatase via PNPP method (for undifferentiated cells), Histopathology tests (for cell identification by morphology), etc. The culture condition was tested by the manual culture plate method and manual sensitivity and identification with versatrek/AP1 was carried out for fungal infection. All the tests were carried out and the cell count and viability of the cells were checked at each stage. Table 50 provides the results of some of the tests.

EXAMPLE 5

Preparation of hES Cells for Transplantation 15 ml of stem cell suspension was taken and centrifuged at 1000 r.p.m. for 7 minutes. The supernatant was discarded. 2 to 15 ml of saline was added to the pellet and the stem cells thus suspended. The suspension was checked for microbial contamination. A viability test was also done.

EXAMPLE 6

Storage of hES Cells in Ready-To-Use Form

Containers (syringe, test tube, flask, vial) filled with the transplantable hES cell suspension were labeled and stored at −20° C. The cold chain was maintained up to the transplantation stage. The suspension was thawed naturally immediately before transplantation.

TABLE 50

| Batch Code | Bilirubin | HIV | HbSAg | Alk Phos | PCR | Albumin | S insulin | Neurofil | Histo | Cell Count (in millions) | Viability % | Culture State |
|---|---|---|---|---|---|---|---|---|---|---|---|---|
| B77 | — | −ve | −ve | — | −ve | — | — | — | — | 3.86 | 72 | Sterile |
| B78 | — | −ve | −ve | — | −ve | — | — | — | — | 3.18 | 70 | Sterile |
| B79 | — | −ve | −ve | — | −ve | — | — | — | — | 3.92 | 70 | Sterile |
| B80 | — | −ve | −ve | — | −ve | — | — | — | — | 3.96 | 68 | Sterile |
| L56 | — | −ve | −ve | — | −ve | — | — | — | — | 3.12 | 72 | Sterile |
| L57 | — | −ve | −ve | — | −ve | — | — | — | — | 3.84 | 72 | Sterile |
| B81 | — | −ve | −ve | — | −ve | — | — | — | — | 3.16 | 70 | Sterile |
| B82 | — | −ve | −ve | — | −ve | — | — | — | — | 3.72 | 68 | Sterile |
| B83 | — | −ve | −ve | — | −ve | — | — | — | — | 3.68 | 74 | Sterile |
| B84 | — | −ve | −ve | — | −ve | — | — | — | — | 3.72 | 72 | Sterile |
| B85 | — | −ve | −ve | — | −ve | — | — | — | — | 3.86 | 76 | Sterile |
| B86 | — | −ve | −ve | — | −ve | — | — | — | — | 3.92 | 78 | Sterile |
| L58 | — | −ve | −ve | — | −ve | — | — | — | — | 3.86 | 82 | Sterile |
| L59 | 1.27 | −ve | −ve | 97 | −ve | 1.9 | 13.2 | — | — | 3.12 | 70 | Sterile |
| B87 | — | −ve | −ve | — | −ve | — | — | — | — | 3.16 | 72 | Sterile |
| B88 | — | −ve | −ve | — | −ve | — | — | — | — | 3.84 | 70 | Sterile |
| L1/V1 | — | −ve | −ve | — | −ve | — | — | — | — | 3.68 | 78 | Sterile |
| L1/V2 | — | −ve | −ve | — | −ve | — | — | — | — | 3.72 | 74 | Sterile |
| B89 | — | −ve | −ve | — | −ve | — | — | — | — | 3.68 | 72 | Sterile |
| B90 | 0.05 | −ve | −ve | 14 | −ve | 0.15 | — | — | — | 3.76 | 70 | Sterile |
| B91 | — | −ve | −ve | — | −ve | — | — | — | — | 3.64 | 68 | Sterile |
| B92 | — | −ve | −ve | — | −ve | — | — | — | — | 3.72 | 72 | Sterile |
| B93 | — | −ve | −ve | — | −ve | — | — | — | — | 3.74 | 70 | Sterile |
| B94 | — | −ve | −ve | — | −ve | — | — | — | — | 3.92 | 72 | Sterile |
| B95 | — | −ve | −ve | — | −ve | — | — | — | — | 3.86 | 70 | Sterile |

−ve = negative test result
— = not done

Cell Lines

Subcultures were repeated more than 100 times to establish hES cells of the present invention. Further, the subcultures were tested for any contamination/infection at each stage of further expansion or storage. The hES cell lines were found to be stable and without any abnormality for over five years of sub culturing cycles.

The present invention is not to be limited in scope by the specific embodiments and examples, which are intended as illustrations of a number of aspects of the invention and any embodiments which are functionally equivalent are within the scope of this invention. Those skilled in the art will know, or be able to ascertain using no more than routine experimentation, many equivalents to the specific embodiments of the invention described herein. These and all other equivalents are intended to be encompassed by the following claims. All patents, patent applications and publications cited herein are fully incorporated by reference.

What is claimed is:

1. A method of expanding hES cells free of animal products, feeder cells, growth factors, leukaemia inhibitory factor, supplementary mineral combinations, amino acid supplements, vitamin supplements, fibroblast growth factor, membrane associated steel factor, soluble steel factor, and conditioned media, comprising:
   (a) introducing hES cells in a cell culture medium consisting of minimal essential medium, a progestin, and a β-human chorionic gonadotropin (βhCG) agonist; and
   (b) incubating the cells at a temperature of about 34° C. to about 38° C. in an environment of about 3.5% to about 6% carbon dioxide for about 12 hours to about 48 hours.

2. The method of claim 1, wherein said cell culture medium is RPMI.

3. The method of claim 1, further comprising:
   (c) taking an aliquot of incubated cells of (b) wherein said aliquot contains at least one cell,
   (d) resuspending the cells in cell culture medium along with progesterone and βhCG to the aliquot,
   (e) diluting the cells in cell culture medium without progestin and βhCG agonist, and
   (f) incubating the cells at a temperature of about 34° C. to about 38° C. in an environment of about 3.5% to about 6% carbon dioxide tor about 12 hours to about 48 hours.

4. The method of claim 1, wherein said incubation is carried out in a water jacketed cell culture incubator.

5. The method of claim 1, wherein said cells in culture medium are incubated in a biocompatible container under substantially anaerobic conditions.

6. The method of claim 5, wherein said cells do not differentiate on proliferation.

7. The method of claim 1, further comprising testing the expanded cells for any contamination.

8. The method of claim 1, wherein said culture process is carried out in biocompatible containers.

9. The method of claim 1, wherein the ratio of the cells to the cell medium is about 1:3.5 to about 1:35.

10. The method of claim 1, wherein said incubation is carried out in a substantially anaerobic environment.

11. The method of claim 1, wherein said incubation is carried out in a biocompatible container where the volume is almost completely occupied by the medium and the container is kept in a vertical position.

* * * * *